(12) United States Patent
Rose et al.

(10) Patent No.: US 8,546,456 B2
(45) Date of Patent: Oct. 1, 2013

(54) FRACTURE FIXATION SYSTEMS

(75) Inventors: John Rose, Collierville, TN (US); Charles C. Martin, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 156 days.

(21) Appl. No.: 13/055,922

(22) PCT Filed: Jul. 24, 2009

(86) PCT No.: PCT/US2009/051715
§ 371 (c)(1),
(2), (4) Date: Apr. 26, 2011

(87) PCT Pub. No.: WO2010/011943
PCT Pub. Date: Jan. 28, 2010

(65) Prior Publication Data
US 2012/0029102 A1    Feb. 2, 2012

Related U.S. Application Data

(60) Provisional application No. 61/083,837, filed on Jul. 25, 2008, provisional application No. 61/084,237, filed on Jul. 28, 2008, provisional application No. 61/142,756, filed on Jan. 6, 2009.

(30) Foreign Application Priority Data
Jul. 25, 2008  (GB) ..................................... 0813659

(51) Int. Cl.
*A61L 24/04* (2006.01)
(52) U.S. Cl.
USPC ............. 521/88; 521/170; 521/137; 521/134; 521/82

(58) Field of Classification Search
USPC .............................. 521/88, 170, 137, 134, 82
See application file for complete search history.

(56) References Cited

U.S. PATENT DOCUMENTS

| 4,313,434 A | 2/1982 | Segal |
| 4,722,948 A | 2/1988 | Sanderson |

(Continued)

FOREIGN PATENT DOCUMENTS

| EP | 987042 A2 | 3/2000 |
| EP | 1132051 A2 | 9/2001 |

(Continued)

OTHER PUBLICATIONS

Xu et al., "Synergistic reinforcement of in situ hardening calcium phosphate composite scaffold for bone tissue engineering," Biomaterials. 25:1029-1037 (2004).

(Continued)

*Primary Examiner* — James J Seidleck
*Assistant Examiner* — Peter A Salamon
(74) *Attorney, Agent, or Firm* — Ropes & Gray LLP

(57) ABSTRACT

Systems for bone fracture repair are disclosed. One system includes a biocompatible putty that may be packed about a bone fracture to provide full loadbearing capabilities within days. The disclosed putties create an osteoconductive scaffold for bone regeneration and degrade over time to harmless resorbable byproducts. Fixation devices for contacting an endosteal wall of an intramedullary (IM) canal of a fractured bone are also disclosed. One such fixation device includes a woven elongated structure fabricated from resorbable polymer filaments. The woven elongated structure has resilient properties that allow the woven structure to be radially compressed and delivered to the IM canal using an insertion tube. When the insertion tube is removed, the woven structure expands towards its relaxed cross-sectional width to engage the endosteal wall. The woven elongated structure is impregnated with a resorbable polymer resin that cures in situ, or in the IM canal.

23 Claims, 25 Drawing Sheets

(56) References Cited

U.S. PATENT DOCUMENTS

| | | | |
|---|---|---|---|
| 4,969,888 A | 11/1990 | Scholten et al. | |
| 5,108,404 A | 4/1992 | Scholten et al. | |
| 5,303,718 A | 4/1994 | Krajicek | |
| 5,320,529 A | 6/1994 | Pompa | |
| 5,336,699 A | 8/1994 | Cooke et al. | |
| 5,423,850 A | 6/1995 | Berger | |
| 5,480,400 A | 1/1996 | Berger | |
| 5,522,893 A * | 6/1996 | Chow et al. | 423/305 |
| 5,549,552 A | 8/1996 | Peters et al. | |
| 5,556,429 A | 9/1996 | Felt | |
| 5,607,985 A | 3/1997 | Masuhara et al. | |
| 5,626,861 A * | 5/1997 | Laurencin et al. | 424/426 |
| 5,632,771 A | 5/1997 | Boatman et al. | |
| 5,658,963 A | 8/1997 | Qian et al. | |
| 5,676,146 A | 10/1997 | Scarborough | |
| 5,681,344 A | 10/1997 | Kelly | |
| 5,728,395 A | 3/1998 | Ohtsuka et al. | |
| 5,800,439 A | 9/1998 | Clyburn | |
| 5,928,239 A | 7/1999 | Mirza | |
| 5,935,127 A | 8/1999 | Border | |
| 5,972,015 A | 10/1999 | Scribner et al. | |
| 5,980,253 A | 11/1999 | Oxman et al. | |
| 6,010,507 A | 1/2000 | Rudloff | |
| 6,022,374 A | 2/2000 | Imran | |
| 6,033,223 A | 3/2000 | Narusawa et al. | |
| 6,114,408 A | 9/2000 | Dickens | |
| 6,117,161 A | 9/2000 | Li et al. | |
| 6,127,597 A | 10/2000 | Beyar et al. | |
| 6,147,137 A | 11/2000 | Jia | |
| 6,206,959 B1 | 3/2001 | Dickens | |
| 6,217,581 B1 | 4/2001 | Tolson | |
| 6,228,072 B1 | 5/2001 | Omaleki et al. | |
| 6,235,043 B1 | 5/2001 | Reiley et al. | |
| 6,245,103 B1 | 6/2001 | Stinson | |
| 6,280,456 B1 | 8/2001 | Scribner et al. | |
| 6,306,177 B1 | 10/2001 | Felt et al. | |
| 6,332,894 B1 | 12/2001 | Stalcup et al. | |
| 6,336,930 B1 | 1/2002 | Stalcup et al. | |
| 6,425,923 B1 | 7/2002 | Stalcup et al. | |
| 6,443,988 B2 | 9/2002 | Felt et al. | |
| 6,447,514 B1 | 9/2002 | Stalcup et al. | |
| 6,582,446 B1 | 6/2003 | Marchosky | |
| 6,613,812 B2 | 9/2003 | Bui et al. | |
| 6,620,185 B1 | 9/2003 | Harvie et al. | |
| 6,623,505 B2 | 9/2003 | Scribner et al. | |
| 6,632,235 B2 | 10/2003 | Weikel et al. | |
| 6,706,069 B2 | 3/2004 | Berger | |
| 6,716,216 B1 | 4/2004 | Boucher et al. | |
| 6,740,093 B2 | 5/2004 | Hochschuler et al. | |
| 6,827,743 B2 | 12/2004 | Eisermann et al. | |
| 6,837,712 B2 | 1/2005 | Qian | |
| 6,852,095 B1 | 2/2005 | Ray | |
| 6,875,212 B2 | 4/2005 | Shaolian et al. | |
| 6,899,713 B2 | 5/2005 | Shaolian et al. | |
| 6,911,017 B2 | 6/2005 | Lee et al. | |
| 6,932,843 B2 | 8/2005 | Smith et al. | |
| 6,964,667 B2 | 11/2005 | Shaolian et al. | |
| 6,997,948 B2 | 2/2006 | Stinson | |
| 7,025,771 B2 | 4/2006 | Kuslich et al. | |
| 7,153,307 B2 | 12/2006 | Scribner et al. | |
| 7,156,861 B2 | 1/2007 | Scribner et al. | |
| 7,166,121 B2 | 1/2007 | Reiley et al. | |
| 7,226,481 B2 | 6/2007 | Kuslich | |
| 7,258,692 B2 | 8/2007 | Thelen et al. | |
| 7,275,933 B2 | 10/2007 | Jia et al. | |
| 7,279,005 B2 | 10/2007 | Stinson | |
| 7,303,798 B2 | 12/2007 | Bavaro et al. | |
| 7,306,610 B2 | 12/2007 | Chern Lin et al. | |
| 7,455,674 B2 * | 11/2008 | Rose | 606/76 |
| 7,465,318 B2 | 12/2008 | Sennett et al. | |
| 7,473,279 B2 | 1/2009 | Baege et al. | |
| 7,481,842 B2 | 1/2009 | Noetzli et al. | |
| 7,485,119 B2 | 2/2009 | Thelen et al. | |
| 7,488,326 B2 | 2/2009 | Elliott | |
| 7,520,880 B2 | 4/2009 | Claypool et al. | |
| 7,524,891 B2 * | 4/2009 | Rose et al. | 523/124 |
| 7,541,049 B1 | 6/2009 | Tormala et al. | |
| 7,559,943 B2 | 7/2009 | Mujwid | |
| 7,563,264 B2 | 7/2009 | Landry et al. | |
| 7,569,060 B2 | 8/2009 | Faoro | |
| 7,578,824 B2 | 8/2009 | Justin et al. | |
| 7,579,322 B2 | 8/2009 | Akella et al. | |
| 7,582,118 B2 | 9/2009 | Brown et al. | |
| 7,588,601 B2 | 9/2009 | Le Couedic et al. | |
| 7,591,836 B2 | 9/2009 | Dick et al. | |
| 7,604,640 B2 | 10/2009 | Kana | |
| 7,604,656 B2 | 10/2009 | Shluzas | |
| 7,611,527 B2 | 11/2009 | Freid et al. | |
| 7,611,538 B2 | 11/2009 | Belliard et al. | |
| 7,618,454 B2 | 11/2009 | Bentley et al. | |
| 7,621,920 B2 | 11/2009 | Claypool et al. | |
| 7,622,562 B2 | 11/2009 | Thorne et al. | |
| 7,632,291 B2 | 12/2009 | Stephens et al. | |
| 7,641,661 B2 | 1/2010 | Steffensmeier et al. | |
| 7,641,663 B2 | 1/2010 | Hodorek | |
| 7,645,301 B2 | 1/2010 | Hudgins et al. | |
| 7,651,496 B2 | 1/2010 | Keegan et al. | |
| 7,658,741 B2 | 2/2010 | Claypool et al. | |
| 7,686,203 B2 | 3/2010 | Rauguth et al. | |
| 7,686,811 B2 | 3/2010 | Byrd et al. | |
| RE41,286 E | 4/2010 | Atkinson et al. | |
| 7,691,132 B2 | 4/2010 | Landry et al. | |
| 7,695,477 B2 | 4/2010 | Creger et al. | |
| 7,699,852 B2 | 4/2010 | Frankel et al. | |
| 7,699,853 B2 | 4/2010 | Durand-Allen et al. | |
| 7,704,255 B2 | 4/2010 | Michelson | |
| 7,704,281 B2 | 4/2010 | Pasquet et al. | |
| 7,708,742 B2 | 5/2010 | Scribner et al. | |
| 7,713,274 B2 | 5/2010 | Shluzas et al. | |
| 7,718,616 B2 | 5/2010 | Thorne | |
| 7,727,239 B2 | 6/2010 | Justin et al. | |
| 7,731,718 B2 | 6/2010 | Schwammberger et al. | |
| 7,731,736 B2 | 6/2010 | Guenther et al. | |
| 7,731,737 B2 | 6/2010 | DiPoto | |
| 7,736,365 B2 | 6/2010 | Phillips et al. | |
| 7,744,600 B2 | 6/2010 | Rangaiah et al. | |
| 7,744,630 B2 | 6/2010 | Lancial | |
| 7,749,272 B2 | 7/2010 | Robie et al. | |
| 7,763,049 B2 | 7/2010 | Roychowdhury | |
| 7,766,969 B2 | 8/2010 | Justin et al. | |
| 7,771,476 B2 | 8/2010 | Justis et al. | |
| 7,771,483 B2 | 8/2010 | Justin et al. | |
| 7,780,671 B2 | 8/2010 | Berger et al. | |
| 7,789,901 B2 | 9/2010 | Froehlich | |
| 7,790,216 B2 | 9/2010 | Popoola et al. | |
| 7,794,504 B2 | 9/2010 | Case | |
| 7,799,057 B2 | 9/2010 | Hudgins et al. | |
| 7,799,079 B2 | 9/2010 | Hestad et al. | |
| 7,799,086 B2 | 9/2010 | Justin et al. | |
| 7,806,898 B2 | 10/2010 | Justin et al. | |
| 7,806,900 B2 | 10/2010 | Rabiner | |
| 7,806,932 B2 | 10/2010 | Webb et al. | |
| 7,811,284 B2 | 10/2010 | Rabiner et al. | |
| 7,811,288 B2 | 10/2010 | Jones et al. | |
| 7,811,290 B2 | 10/2010 | Rabiner | |
| 7,815,650 B2 | 10/2010 | Shluzas et al. | |
| 7,819,876 B2 | 10/2010 | Claypool et al. | |
| 7,819,905 B2 | 10/2010 | Newcomb et al. | |
| 7,824,409 B2 | 11/2010 | Howie et al. | |
| 7,828,805 B2 | 11/2010 | Hoag et al. | |
| 7,833,226 B2 | 11/2010 | Grabowski et al. | |
| 7,833,249 B2 | 11/2010 | Shaolian et al. | |
| 7,833,271 B2 | 11/2010 | Mitchell et al. | |
| 7,842,040 B2 | 11/2010 | Rabiner et al. | |
| 7,842,072 B2 | 11/2010 | Dawson | |
| 7,846,189 B2 | 12/2010 | Winquist et al. | |
| 7,847,072 B2 | 12/2010 | Thorne | |
| 7,854,767 B2 | 12/2010 | May et al. | |
| 7,857,834 B2 | 12/2010 | Boschert | |
| 7,867,236 B2 | 1/2011 | Hodorek et al. | |
| 7,867,280 B2 | 1/2011 | Goble et al. | |
| 7,875,035 B2 | 1/2011 | Boucher et al. | |
| 1,004,038 A1 | 2/2011 | Alini at al. | |
| 7,879,041 B2 | 2/2011 | Rabiner et al. | |

| | | |
|---|---|---|
| 7,879,073 B2 | 2/2011 | Pasquet et al. |
| 7,879,075 B2 | 2/2011 | Shluzas |
| 7,892,267 B2 | 2/2011 | Lancial et al. |
| 7,892,288 B2 | 2/2011 | Blaylock et al. |
| 7,892,369 B2 | 2/2011 | Bhambri |
| 7,896,919 B2 | 3/2011 | Belliard et al. |
| 7,914,558 B2 | 3/2011 | Landry et al. |
| 7,918,382 B2 | 4/2011 | Charlebois et al. |
| 7,922,753 B2 | 4/2011 | Eidenschink et al. |
| 7,922,772 B2 | 4/2011 | Goble et al. |
| 7,931,650 B2 | 4/2011 | Winquist et al. |
| 7,935,135 B2 | 5/2011 | Mujwid |
| 7,938,857 B2 | 5/2011 | Garcia-Bengochea et al. |
| 7,947,045 B2 | 5/2011 | Hestad et al. |
| 7,947,064 B2 | 5/2011 | Bergeron et al. |
| 7,963,969 B2 | 6/2011 | Sanford |
| 7,963,979 B2 | 6/2011 | Phillips et al. |
| 7,985,242 B2 | 7/2011 | Forton et al. |
| 7,985,247 B2 | 7/2011 | Shluzas et al. |
| 7,985,781 B2 | 7/2011 | Muratoglu et al. |
| 7,988,700 B2 | 8/2011 | Shluzas et al. |
| 7,993,341 B2 | 8/2011 | Grimm et al. |
| 8,002,810 B2 | 8/2011 | Osman |
| 8,007,519 B2 | 8/2011 | Hudgins et al. |
| 8,007,523 B2 | 8/2011 | Wagner et al. |
| 8,007,535 B2 | 8/2011 | Hudgins et al. |
| 8,012,157 B2 | 9/2011 | Chang et al. |
| 8,025,677 B2 | 9/2011 | Freid et al. |
| 8,029,566 B2 | 10/2011 | Lozier et al. |
| 8,034,084 B2 | 10/2011 | Landry et al. |
| 8,066,711 B2 | 11/2011 | Rabiner et al. |
| 2002/0032444 A1 | 3/2002 | Mische |
| 2002/0082600 A1 | 6/2002 | Shaolian et al. |
| 2003/0134099 A1 | 7/2003 | Barrows |
| 2003/0180376 A1* | 9/2003 | Dalal et al. .................. 424/602 |
| 2004/0098015 A1 | 5/2004 | Weikel et al. |
| 2004/0199246 A1 | 10/2004 | Chu et al. |
| 2004/0220672 A1 | 11/2004 | Shadduck |
| 2005/0010297 A1 | 1/2005 | Watson et al. |
| 2005/0065434 A1 | 3/2005 | Bavaro et al. |
| 2005/0149022 A1 | 7/2005 | Shaolian et al. |
| 2005/0238683 A1* | 10/2005 | Adhikari et al. ............. 424/423 |
| 2005/0255317 A1 | 11/2005 | Bavaro et al. |
| 2006/0106459 A1 | 5/2006 | Truckai et al. |
| 2006/0116682 A1 | 6/2006 | Longo |
| 2006/0155296 A1 | 7/2006 | Richter |
| 2006/0173464 A1 | 8/2006 | Ellman et al. |
| 2006/0217736 A1 | 9/2006 | Kaneko et al. |
| 2007/0021769 A1 | 1/2007 | Scribner et al. |
| 2007/0027230 A1 | 2/2007 | Beyar et al. |
| 2007/0043373 A1 | 2/2007 | Sala et al. |
| 2007/0055267 A1 | 3/2007 | Osorio et al. |
| 2007/0087031 A1 | 4/2007 | Ashman et al. |
| 2007/0093847 A1 | 4/2007 | Scribner et al. |
| 2007/0123877 A1 | 5/2007 | Goldin et al. |
| 2007/0225705 A1 | 9/2007 | Osorio et al. |
| 2007/0233105 A1 | 10/2007 | Nelson et al. |
| 2007/0255287 A1 | 11/2007 | Rabiner |
| 2008/0039854 A1 | 2/2008 | Rabiner |
| 2008/0045896 A1 | 2/2008 | Yribarren et al. |
| 2008/0058932 A1 | 3/2008 | Trieu et al. |
| 2008/0114364 A1 | 5/2008 | Goldin et al. |
| 2008/0125784 A1 | 5/2008 | Rabiner et al. |
| 2008/0154368 A1 | 6/2008 | Justis et al. |
| 2008/0215151 A1 | 9/2008 | Kohm et al. |
| 2008/0269745 A1 | 10/2008 | Justin |
| 2008/0269747 A1 | 10/2008 | Justin |
| 2008/0269748 A1 | 10/2008 | Justin et al. |
| 2008/0269749 A1 | 10/2008 | Shalaby et al. |
| 2008/0269750 A1 | 10/2008 | Justin |
| 2008/0269776 A1 | 10/2008 | Justin et al. |
| 2008/0318188 A1 | 12/2008 | Stansbury et al. |
| 2009/0005469 A1 | 1/2009 | Craig et al. |
| 2009/0048620 A1 | 2/2009 | Weiss et al. |
| 2009/0048629 A1 | 2/2009 | Rabiner |
| 2009/0054900 A1 | 2/2009 | Rabiner et al. |
| 2009/0112196 A1 | 4/2009 | Rabiner et al. |
| 2009/0177204 A1 | 7/2009 | Colleran et al. |
| 2009/0299401 A1 | 12/2009 | Tilson |
| 2010/0087709 A1 | 4/2010 | Bertolero et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0311858 A1 | 12/2010 | Holmes et al. |
| 2010/0331850 A1 | 12/2010 | Rabiner |
| 2011/0004213 A1 | 1/2011 | Rabiner et al. |
| 2011/0009871 A1 | 1/2011 | Rabiner |
| 2011/0046746 A1 | 2/2011 | Rabiner et al. |
| 2011/0054480 A1 | 3/2011 | Rabiner et al. |
| 2011/0098713 A1 | 4/2011 | Rabiner et al. |
| 2011/0118740 A1 | 5/2011 | Rabiner et al. |
| 2011/0144688 A1 | 6/2011 | Reiss et al. |
| 2011/0166306 A1 | 7/2011 | Stansbury et al. |
| 2011/0198019 A1 | 8/2011 | Tilson et al. |

FOREIGN PATENT DOCUMENTS

| | | |
|---|---|---|
| EP | 1132053 A1 | 9/2001 |
| EP | 1132061 A2 | 9/2001 |
| EP | 1212991 A2 | 6/2002 |
| EP | 1272131 A2 | 1/2003 |
| EP | 1303236 A2 | 4/2003 |
| EP | 1 829 564 A1 | 9/2007 |
| EP | 1829564 A1 * | 9/2007 |
| EP | 1973513 A2 | 10/2008 |
| WO | WO-9514501 A1 | 6/1995 |
| WO | WO-95-20362 A1 | 8/1995 |
| WO | WO-03020110 A2 | 3/2003 |
| WO | WO-2004058045 A2 | 7/2004 |
| WO | WO-2005-112804 A1 | 12/2005 |
| WO | WO-2007127255 A2 | 11/2007 |
| WO | WO-2007127260 A2 | 11/2007 |
| WO | WO-2008063265 A1 | 5/2008 |
| WO | WO-2008096363 A2 | 8/2008 |
| WO | WO-2008116170 A2 | 9/2008 |
| WO | WO-2010050965 A1 | 5/2010 |

OTHER PUBLICATIONS

Peppas et al., "New Challenges in Biomaterials", Science, 263:1715-1719 (1994).

VanLanduyt et al., "How much do resin-based dental materials release? A meta-analytical approach," Dental Materials, 27:723-747 (2011).

Michelsen et al., "Quantification of organic eluates from polymerized resin-based dental restorative materials by use of GC/MS," Journal of Chromatography B, 850:83-91 (2007).

* cited by examiner

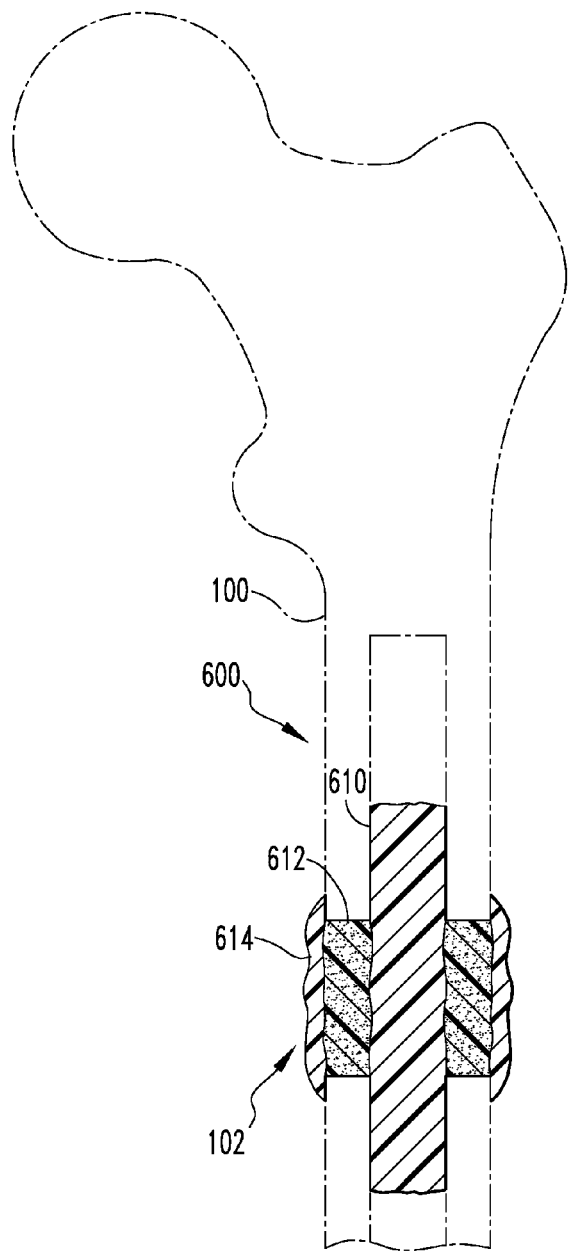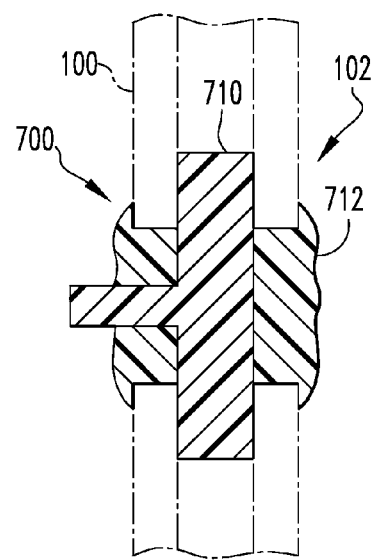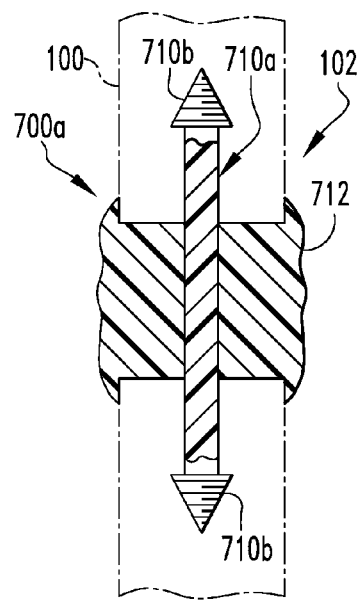
FIG. 9
FIG. 10
FIG. 10A

FRACTURE FIXATION SYSTEMS

CROSS-REFERENCE TO RELATED APPLICATIONS

This application is a national stage filing under 35 U.S.C. 371 of International Application No. PCT/US2009/051715, filed on Jul. 24, 2009, which claims the benefit of the filing date under 35 U.S.C. 119(e) priority to U.S. Provisional Application Ser. No. 61/142,756, filed on Jan. 6, 2009, U.S. Provisional Application Ser. No. 61/084,237, filed on Jul. 28, 2008, U.S. Provisional Application Ser. No. 61/083,837, filed on Jul. 25, 2008, and G.B. Provisional Application Serial No. 0813659.0, filed on Jul. 25, 2008, the entire contents of which is incorporated herein by reference. International Application No. PCT/US2009/051715 was published under PCT Article 21(2) in English.

BACKGROUND

1. Technical Field

This disclosure relates generally to orthopedic implants and, more particularly, to orthopedic implants adapted for fracture repair and methods for repairing fractures.

2. Description of the Related Art

A variety of systems and devices are conventionally used to treat bone fractures in humans or animals. Bone fractures typically heal naturally as a result of normal growth or regeneration processes. Treatment of bone fractures generally includes placing bone fragments into an anatomically correct position and orientation, referred to as "reduction," and maintaining the fragments in place until healing naturally occurs, referred to as "fixation." Accordingly, a primary objective in the treatment of bone fractures is the fixation or stabilization of the reduced, fractured bone for the duration of the healing process.

Conventional systems and devices for treatment of fractures include external fixation means, such as traction, splints, or casts, and internal fixation means, such as plates, nails, pegs, screws, and other fixtures. Internal fixation devices are installed on or in the fractured bone across the fracture site. For example, plates, screws, pegs apply compression forces across a fracture site, thereby aiding in stabilizing a bone fracture across the fracture site. Intramedullary nails are installed longitudinally into the intramedullary (IM) canal of a fractured bone across the fracture site and provide torsional stabilization as well as load sharing along the central axis of the bone.

One common problem with internal fixation devices is that the installation of such devices is generally dependent on the presence of sufficient amounts of high quality bone tissue in the vicinity of the fracture. When bone tissue is lost, due to disease, a pathological condition or for other reasons, it may be difficult to install internal fixation devices to stabilize the bone sufficiently for healing. For example, persons with thin or fragile bones, such as osteoporosis patients, avascular necrosis patients and patients with metastatic bones, may be particularly prone to difficulties with fixation and healing of fractures. Unfortunately, these are the very patients that are most prone to bone fractures. While external fixation devices and methods are available, external fixation devices can be cumbersome, uncomfortable, limit or prevent ambulation and therefore generally fail to satisfy the needs of such patients.

Current fixation devices, both internal and external, also fail to meet the needs of injured soldiers and other trauma victims. Specifically, approximately thirty percent of all battlefield trauma cases involve bone fractures, typically due to high energy events, such as blasts or gunshots. For example, the combination of comminuted open fractures with large bone loss and significant soft tissue loss are common battlefield traumas. Such cases, often referred to as "segmental defects," are very difficult to treat and typically require multiple surgeries and long healing/rehabilitation times that can last as long as two years. Amputations in these cases are common.

Current treatment techniques include the use of internal and external fixation with titanium plates, screws, and rods or IM nails, and the Ilizarov distraction method for bone-lengthening. However, current techniques suffer from significant deficiencies, some of which arise from the mechanical property mismatch between titanium and bone. This mismatch leads to complications including further fractures, delayed healing, and a high prevalence of infection. Furthermore, currently available techniques do not provide the most effective treatment in repairing large segmental defects, which are generally defined as a defect or missing bone segment that exceeds 2 cm in length or width. Because many currently available fixation devices are not fully load-bearing, the soldier or patient may be effectively incapacitated during the recovery period.

Therefore, in light of the above problems, more effective fixation methods and devices are urgently needed for the treatment of both common bone fractures as well as bone fractures considered to be large segmental defects.

SUMMARY OF THE DISCLOSURE

Various systems for bone fracture repair are disclosed which are applicable to typical bone fractures without significant bone loss and bone fractures classified as having large or significant segmental defects.

One disclosed system may comprise fracture putty in the form of a dynamic putty-like material that, when packed in/around a compound bone fracture, may provide full load-bearing capabilities within days. The disclosed putties may create an osteoconductive scaffold for bone regeneration. The disclosed putties may also degrade over time to harmless resorbable by-products as normal bone regenerates. The disclosed putties may be curable in situ.

The disclosed putties may be made from resorbable polymers which can harden or cure in situ, for example polyurethane, polypropylene fumarate, polycapralactone, etc.

The disclosed putties may include a first or primary filler in the form of biocompatible and osteoconductive particles that can form a scaffold structure that bridges healthy bone segments. The first or primary filler, preferably in the form of particles, may also provide porosity, bone ingrowth surfaces and enhanced permeability or pore connectivity. One suitable particulate filler material is hydroxyapatite (HA) although other suitable filler materials will be apparent to those skilled in the art such as calcium phosphates, orthophosphates, monocalcium phosphates, dicalcium phosphates, tricalcium phosphates, whitlockite, tetracalcium phosphates, amorphous calcium phosphates and combinations thereof.

The particles may comprise degradable polymer (e.g. PU, PLA, PGA, PCL, co-polymers thereof, etc.) or the particles may comprise degradable polymer containing one or more ceramic fillers. The first filler particles may be provided in varying sizes.

In one refinement, the first filler particles have mean diameters ranging from about 1 μm to about 15 μm. For example, in one disclosed putty, the first filler has a mean particle size of about 10 μm.

In a refinement, the porosity and compressive properties of the disclosed putties may be manipulated using additional fillers materials that may be HA or another suitable biocompatible material. Such refinements include the addition of particles having mean diameters ranging from about 400 to about 4000 μm. In certain disclosed putties, the additional filler materials may be provided in one or more size distributions. For example, additional filler material is provided in size distributions ranging from about 400 to about 4200 μm, from about 400 to about 3200 μm, from about 600 to about 3000 μm, from about 800 to about 2800 μm, from about 400 to about 2200 μm, from about 800 to about 1800 μm, from about 1400 to about 3200 μm, from about 1800 to about 2800 μm, etc. The ratio of the particle size distributions can be manipulated depending upon the compression strength required or the porosity required. For example, large segmental defect injuries to load bearing bones will necessitate higher compression strength and possibly reduced porosity. In contrast, large segmental defect injuries to non-load bearing bones require less compression strength thereby enabling the surgeon to use the putty with a higher porosity for shorter healing times.

In one example, a second filler is added that may have a mean particle diameter ranging from about 400 to about 1800 μm and a third filler that may have a mean particle size greater than the mean particle size of the second filler and ranging from about 1800 to about 4000 μm.

In a refinement, the resin may be present in an amount ranging from about 15 to about 40 wt %, the first filler may be present in an amount ranging from about 10 to about 25 wt %, the second filler may be present in an amount ranging from about 20 to about 40 wt %, and the third filler may be present in an amount ranging from about 15 to about 35 wt %.

In another refinement, the first filler may have a mean particle diameter ranging from about 8 to about 12 μm, the second filler may have a mean particle diameter ranging from about 800 to about 1800 μm and the third filler may have a mean particle diameter ranging from greater than 1800 to about 2800 μm. In a further refinement of this concept, the resin may be present in an amount ranging from about 20 to about 30 wt %, the first filler in an amount ranging from about 10 to about 20 wt %, the second filler in an amount ranging from about 25 to about 35 wt %, the third filler in an amount ranging from about 20 to about 30 wt %.

In another refinement, the first filler is present in a first amount, the second filler is present in a second amount and the third filler is present in a third amount. A ratio of the second to third amounts may range from about 1:1 to about 1.5:1. In another refinement, a ratio of the second and third amounts combined to the first amount may range from about 3.5:1 to about 4.5:1

The disclosed putties may also include an additional porogen. In one refinement, the porogen is mannitol but other biocompatible porogens will be apparent to those skilled in the art such as crystalline materials in the form of salts, sugars, etc.

Another disclosed moldable material for orthopedic implantation and reconstruction comprises a resorbable polymer resin present an amount ranging from about 20 to about 60 wt %, a first filler having a first mean particle diameter ranging from about 1 to about 15 μm and present in an amount ranging from about 10 to about 30 wt %, and mannitol as a porogen and present in an amount ranging from about 30 to about 50 wt %.

The disclosed putties may also include a blowing agent. In one refinement, the blowing agent is water but other biocompatible blowing agents will be apparent to those skilled in the art.

Fixation devices for contacting an endosteal wall of an intramedullary (IM) canal of a fractured bone are also disclosed. One such fixation device comprises a woven elongated structure fabricated from a resorbable polymer filaments. The woven elongated structure may have a relaxed cross-sectional width and a compressed cross-sectional width. The relaxed cross-sectional width may be at least about 50% larger than the compressed cross-sectional width. This resilient property allows the woven structure to be radially compressed, placed in an insertion tube and delivered to the IM canal using the insertion tube. When the insertion tube is removed, the woven structure expands towards its relaxed cross-sectional width to engage the endosteal wall. The woven elongated structure may have a closed distal end. The woven elongated structure is coated with a resorbable polymer resin that cures in situ, or in the IM canal. The combination of the woven elongated structure and the cured resin provides a strong internal fixation device.

In a refinement, the woven elongated structure is selected from the group consisting of a braided elongated structure, a triaxial braided elongated structure, a pair of braided elongated structures with one smaller inner braided elongated structure disposed axially within a larger outer braided elongated structure, a bundle of braided elongated structures, a bundle of braided elongated structures disposed axially within an outer braided elongated structure, a braided elongated structure with a plurality of cavities extending along a length of the braided elongated structure, and an elongated structure fabricated from the spacer fabric that may be rolled or folded.

For embodiments that employee a triaxial braided elongated structure, the longitudinal fibers may be single or individual fibers, longitudinal fiber bundles or yarns, or the longitudinal fibers may be crimped.

In a refinement, the device may include a retention structure that substantially encloses the woven elongated structure for inhibiting the migration of injected resin out through the woven elongated structure and possibly of the IM canal. The retention structure may be selected from the group consisting of a balloon, a bag, a sheath or other suitable enclosure. The retention element may be fabricated from a resorbable material, such as a resorbable polymer. In such a refinement, the woven elongated structure may be filled with resin.

In another refinement, the resin may include particulate filler material as described above. In another refinement, the resin further comprises reinforcing resorbable fibers. In another refinement, the woven elongated structure accommodates an elongated structural reinforcing element.

In a refinement, the woven elongated structure may comprise filaments selected from the group consisting of polyurethanes, poly-alpha-hydroxy acids, polylactides, polyglycolides, poly-(D,L-lactide-co-glycolide), polyglycolide-co-trimethylenecarbonate, poly-(L-lactide), poly-(L-CO-D,L-lactide), poly-(D,L-lactide), polyglactin acid, a combination, poly-(D-lactide), combinations thereof and copolymers thereof.

In another refinement, the woven elongated structure accommodates a plurality of loose resorbable fibers for mixing with resin injected into the woven elongated structure.

An assembly for placing a fixation device in contact with an endosteal wall of an intramedullary (IM) canal of a fractured bone is also disclosed. One disclosed assembly comprises an insertion tube that accommodates a woven elongated structure as described above. The woven elongated structure may have a closed distal end and is in compressible to a cross-section smaller than an inner diameter of the injection tube but expandable to relaxed cross-section greater than an inner diameter of the injection tube for engaging the endosteal wall of the IM canal. The woven elongated structure accommodates a distal end of an injection tube for delivering resin to the woven elongated structure.

The woven elongated structure may take the form of any of the alternatives described above, may include a retention element, one or more reinforcing elements and/or a plurality of loose reinforcing fibers. Further, the use of an insertion tube enables the option of providing a woven elongated structure that is pre-wetted with uncured resin which cures in situ using the assembly described above. In another refinement, the resin is light-curable and can be cured in situ by passing a light emitting device axially through the woven elongated structure after it is placed in the IM canal.

Use of any of the internal fixation devices or systems disclosed herein may be combined with one or more external fixation systems, as will be apparent to those skilled in the art.

The disclosed fixation systems and methods may yield one or more of the following benefits: (1) the patient may be more rapidly restored to ambulatory function while healing naturally occurs; (2) a single procedure may be employed that significantly simplifies orthopedic surgery; (3) fewer secondary fractures may result from use of the disclosed systems and methods thereby promoting normal healing and fewer infections; (4) reduction in recovery/rehabilitation time; (5) potential treatment for severe bone loss; (6) potential treatment for joint fractures; (7) reduction in the number of amputations; (8) the fixation systems are wholly or at least partly resorbable thereby avoiding the need for a secondary procedure to remove the fixation device after the bone has healed.

There is provided a hardenable and moldable material for orthopedic implantation and reconstruction, the material comprising: a resorbable polymer resin; optionally, a first filler having a first mean particle diameter ranging from about 5 to about 15 μm; at least one additional filler selected from the group consisting of a second filler having a mean particle diameter ranging from about 400 to about 1800 μm and a third filler having a mean particle size greater than the mean particle size of the second filler and ranging from about 1800 to about 4000 μm, the at least one additional filler increasing a porosity of the material after hardening and being present in an amount greater than the first filler.

In some embodiments, the resin is present in an amount ranging from about 15 to about 40 wt %; the first filler is present in an amount ranging from about 10 to about 25 wt %; the additional filler is present in an amount greater than the first filler and ranging from about 20 to about 75 wt %.

In some embodiments, the additional filler comprises both second and third fillers.

In some embodiments, the resin is present in an amount ranging from about 15 to about 40 wt %; the first filler is present in an amount ranging from about 10 to about 25 wt %; the second filler is present in an amount ranging from about 20 to about 40 wt %; the third filler is present in an amount ranging from about 15 to about 35 wt %.

In some embodiments, the first filler is present in a first amount, the second filler is present and a second amount and the third filler is present in a third amount, and a ratio of the second to third amounts ranges from about 1:1 to about 1.5:1.

In some embodiments, a ratio of the second and third amounts combined to the first amount ranges from about 3.5:1 to about 4.5:1

In some embodiments, the material further includes a porogen comprising water soluble crystals.

In some embodiments, the porogen comprises mannitol.

In some embodiments, the material further includes water as a blowing agent.

In some embodiments, the first filler has a mean particle diameter ranging from about 8 to about 12 μm, the second filler has a mean particle diameter ranging from about 800 to about 1800 μm and the third filler has a mean particle diameter ranging from greater than 1800 to about 2800 μm.

In some embodiments, the resin is present in an amount ranging from about 20 to about 30 wt %; the first filler is present in an amount ranging from about 10 to about 20 wt %; the second filler is present in an amount ranging from about 25 to about 35 wt %; the third filler is present in an amount ranging from about 20 to about 30 wt %.

In some embodiments, the first filler is present in a first amount, the second filler is present and a second amount and the third filler is present in a third amount, and a ratio of the second to third amounts ranges from greater than 1:1 to about 1.5:1.

In some embodiments, a ratio of the second and third amounts to the first amount ranges from about 3.5:1 to about 4.5:1

In some embodiments, the material further includes a porogen comprising water soluble crystals.

In some embodiments, the first, second and third fillers are selected from the group consisting of hydroxyapatite (HA), calcium phosphates, orthophosphates, monocalcium phosphates, dicalcium phosphates, tricalcium phosphates, whitlockite, tetracalcium phosphates and amorphous calcium phosphates.

In some embodiments, the material further includes water as a blowing agent.

There is provided a moldable, hardenable and porous material for orthopedic implantation and reconstruction, the material comprising: a resorbable polymer resin present in an amount ranging from about 20 to about 60 wt %; a first filler having a first mean particle diameter ranging from about 5 to about 15 μm and present in an amount ranging from about 10 to about 30 wt %; and mannitol as a porogen and present in an amount ranging from about 30 to about 50 wt %.

In some embodiments, a second filler having a mean particle diameter ranging from about 400 to about 1800 μm; and a third filler having a mean particle size greater than the mean particle size of the second filler and ranging from about 1800 to about 4000 μm.

In some embodiments, the first filler is selected from the group consisting of hydroxyapatite (HA), calcium phosphates, orthophosphates, monocalcium phosphates, dicalcium phosphates, tricalcium phosphates, whitlockite, tetracalcium phosphates and amorphous calcium phosphates.

There is provided a moldable material for orthopedic implantation and reconstruction, the material comprising: a resorbable polymer resin present in an amount ranging from about 15 to about 40 wt %; a first filler having a first mean particle diameter ranging from about 8 to about 12 μm and present in an amount ranging from about 10 to about 25 wt %; a second filler having a mean particle diameter ranging from about 600 to about 1800 μm and present in an amount ranging from about 20 to about 40 wt %; a third filler having a mean particle size ranging from greater than 1800 to about 2800 μm and present in an amount ranging from about 15 to about 35 wt %; the second and third fillers increasing a porosity of the material after hardening when present in cumulative amounts greater than the first filler.

In some embodiments, the first filler is present in a first amount, the second filler is present and a second amount and the third filler is present in a third amount, and a ratio of the second to third amounts ranges from about 1:1 to about 1.5:1.

In some embodiments, a ratio of the second and third amounts combined to the first amount ranges from about 3.5:1 to about 4.5:1

Other advantages and features will be apparent from the following detailed description when read in conjunction with the attached drawings.

BRIEF DESCRIPTION OF THE DRAWINGS

For a more complete understanding of the disclosed systems and methods, reference should be made to the embodiments illustrated in greater detail in the accompanying drawings, wherein:

FIG. 9 is a cross-sectional view of a fracture with another disclosed internal fixation system.

FIG. 10 is a cross-sectional view of a fracture with another disclosed internal fixation system.

FIG. 10A is a cross-sectional view of a fracture with another disclosed internal fixation system.

Figure 1:
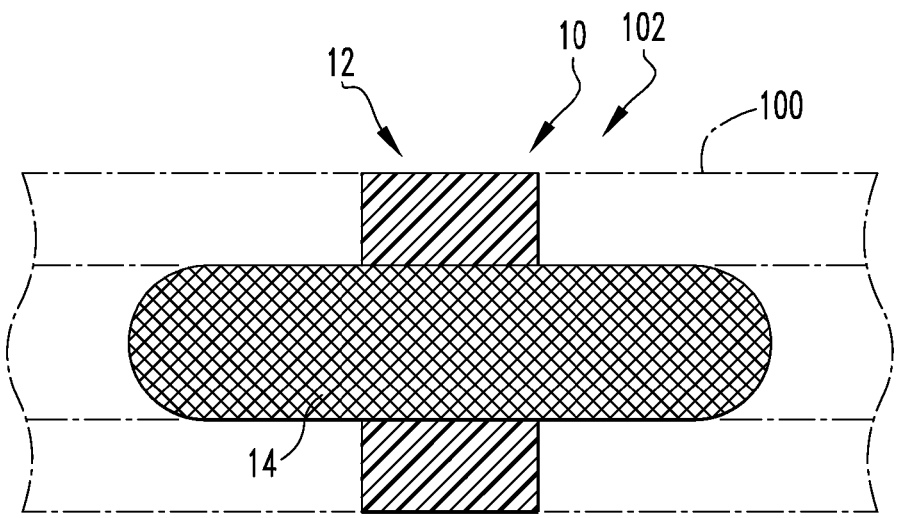
FIG. 1 is a cross-sectional view of a fracture with a disclosed internal fixation system for fracture repair.

It should be understood that the drawings are not necessarily to scale and that the disclosed embodiments are sometimes illustrated diagrammatically and in partial views. In certain instances, details which are not necessary for an understanding of the disclosed systems and methods or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

The disclosed systems and methods are also advantageously used in treatment of bone fractures associated with disease, pathological conditions or injury.

Treatment of Bone Fractures

Healing of bone fractures generally occurs, at least to some degree, naturally in humans or animals as a result of formation of new bone tissue in a fractured bone. New bone formation, which is sometimes termed "ossification" or bone "ingrowth," naturally occurs due to the activity of bone cells, such as osteoblasts and osteoclasts and eventually results in closing of a fracture site with newly formed tissue. In order for the bone tissue to grow such that a fractured bone heals into its pre-fracture form and restores its function, the bone pieces or fragments have to be located in their appropriate natural physical position and orientation, a process referred to as "reduction." Further, the bone fragments must be maintained in said position and orientation for the duration of the healing, referred to as "fixation." Treatment of fractures is generally aimed at providing the best conditions for a bone to heal and preventing movement of a bone or its fragments in order to prevent or lessen damage to bone, cartilage or soft tissues. Systems disclosed herein are designed to assist in both reduction and fixation and enhance bone in-growth across a fracture site by providing biocompatible materials that form a scaffold across a fracture site.

Resorbable Materials

Disclosed methods or devices may comprise or utilize one or more resorbable, bioerodible, or degradable material for fixation devices. Upon installation of a fixation device comprising such material, gradual resorption of the material takes place, thereby making space available for bone ingrowth, which can be advantageous over the use of non-resorbable metal materials for fixation devices. The term "biodegradable" may be used interchangeably with the terms "bioabsorbable", "bioresorbable", "resorbable", "degradable", "erodible", or "bioerodible", and these terms are used to characterize materials that gradually disintegrate after implantation into a human or an animal.

Biodegradable materials used may be beneficial for promotion of tissue formation, with properties such as porosity and degradation chosen to encourage tissue growth and vascularization, if appropriate, within the material. Degradation rate may be coupled to the rate of bone tissue formation so that neither the load-bearing capabilities of the tissue, nor tissue regeneration are compromised. Accordingly, degradation rate of biodegradable materials may be timed to ensure adequate time for growth of bone tissue into a void, space, or cavity between a bone and a joint implant. The resorbable material may be at least partially resorbed over a predetermined period of time. The degradation time may be chosen depending on a particular application and can range from a few weeks to a few years or more. As with all implanted materials, biodegradable materials may be sterilizable to prevent infection. Sterilization may or may not substantially interfere with the bioactivity of the material, alter its chemical composition or affect its biocompatibility or degradation properties.

The resorbable materials may include, but are not limited to, polymeric materials, such as polyurethane, poly-alpha-hydroxy acids, polylactide and polyglycolide, including their copolymers, poly-(D,L-lactide-co-glycolide) and polyglycolide-co-trimethylenecarbonate; stereopolymers, such as poly-(L-lactide) or poly-Lactic acid (PLA), poly-(L-CO-D,L-lactide) and poly-(D,L-lactide), polyglactin acid (PGA), a combination thereof (PLA/PGA) or any derivative, combination, composite, or variation thereof, poly-(D,L-lactide-co-glycolide) (PDLLA-co-PGA), poly-(L-lactide) (PLLA), poly-(D-lactide) (PDLA), polyglycolide-co-trimethylenecarbonate, (PGA-co-TMC), poly-(L-CO-D,L-lactide), poly-(D,L-lactide), (PDLLA). The use of slow degrading and highly crystalline polymers, such as poly-(L-lactide) and poly(L-CO-D,L-lactide) stereocopolymers with a low D,L amount, amorphous polymers, such as poly-(L-CO-D,L-lactide) stereocopolymers with a high D,L amount of poly-(D,L-lactide), or fast-degrading copolymers, such as poly-(D,L-lactide-co-glycolide) or polyglycolide-co-trimethylenecarbonate, is envisioned and falls within the scope of this disclosure. The use of injectable or crosslinkable polymers, including, but not limited to, photopolymerizable and chemically polymerizable polymers and polymers that harden in situ, is also encompassed by this disclosure, including but not limited to the use of polymers of sebacic acid (SA), alone, or copolymers of SA and 1,3-bis(p-carboxyphenoxy) propane (CPP), or 1,6-bis(p-carboxyphenoxy)hexane (CPH), or poly(propylene fumarate) (PPF). Resorbable materials are not limited to the foregoing and may also include any fully or partially degradable or erodible in a body chemical composition, including but not limited to carbohydrates and derivatives thereof, such as such as cellulose or hyaluronic acid. A modification of polymeric materials to adjust their structural, mechanical or chemical properties, or facilitate biological responses in tissues is envisioned and falls within the scope of this disclosure. The resorbable material may include a two phase polymer system wherein one phase degrades faster than another to allow for adequate strength and bone in-growth. The system may be a non-miscible blend. An example of the two phase polymer system is PDLA in combination with polyurethane.

Hardenable Void Fillers—Putties and Resins

Disclosed methods or devices may comprise or utilize one or more of hardenable resins that are biocompatible and at least partially resorbable. A term "hardenable" as used herein means that the material is able to change consistency, harden, stiffen, crosslink, cure and become firm, stable, or settled. Both putties and resins may be injectable before they cure. The disclosed putties generally include resin, with additional filler materials to make the putty more viscous and moldable. The disclosed putties are used alone or in combination with additional fixation devices for the repair of segmental defects. In contrast, disclosed resins are primarily used in the IM canal in combination with one or more reinforcing and/or containment devices.

Certain disclosed polyurethane resins are two component material available from PolyNovo Biomaterials Pty. Ltd. of Australia (http://www.polynovo.com/). One particularly suitable polyurethane resin is made from a hydroxyl functional material (R—OH) that is reacted with a polyisocyanate (R—NCO). The setting time of the resin is controlled through the addition of one or more catalysts to the reaction mixture. The isocyanate may be ethyl-lysine diisocyanate (ELDI) and the hydroxyl may be pentaerythritol. The polyurethane may include an ester bond, which allows for hydrolyzed degradation to take place.

The PolyNovo polyurethane resins and alternative resins are described in the following U.S. Patent Application Publications and PCT Application: (1) 2005/0197422; (2) 2005/0238683; (3) 2006/0051394; and WO 2009/043099, each of which is herein incorporated by reference.

With the addition of fillers, the polyurethane resin can form a putty which is moldable by hand. Other additives such as porogens and blowing agents are used to create porosity.

In addition to polyurethanes, the disclosed putties and resins, the disclosed putties may be made from resorbable polymers which can harden or cure in situ, for example polyurethane, polypropylene fumarate, polycapralactone, etc.

Alternatively, the resin, or putty made therefrom, may be an injectable and/or moldable, biocompatible calcium phosphate material that sets in situ, such as NORIAN® (Norian Corporation of 1302 Wrights Lane East, West Chester, Pa., USA).

The resin may also comprise a biocompatible epoxy resin. The most common commercially available epoxy resin is Diglycidyl Ether of Bisphenol-A (DGEBA) which is the reaction product of Bisphenol A and Epichlorohydrin.

The resins and putties made from the resins may be customized. In particular, properties of a putty or resin are designed, selected or modified so that the material possesses properties suitable or desirable for stabilization of a fracture when injected into the bone cavity. Examples of some of the material's properties that can be customized include, but are not limited to: porosity, pore connectivity, permeability, compression strength, Young's modulus, bending modulus, shear modulus, torsional modulus, yield strength, ultimate strength, or Poisson's ratio. A putty or resin may be further stabilized to contain a radio opaque material for x-ray visualization in order to assess or improve positioning intra-operatively, and monitor an implant during follow up visits.

The resin may comprise a suitable degradable ceramic cement such comprising any one or more of, brushite, calcium sulphate and calcium phosphate.

The resins may comprise degradable glass ionomers. These resins can be produced by combining acid functionalized polymers with ion leaching glasses such as a degradable polyacrylic acid-co-caprolatone copolymers or a polyamino acid combined with degradable glasses which liberate divalent and trivalent ionic species such as calcium, magnium, zinc, aluminium, iron, copper etc.

Degradable polymeric based cements may also comprise unsaturated low molecular weight polymers, such as fumerates or branched or telechelic macromers based on degradable polyester, polyamide, polyurethane, polycarbonate, etc. One example is low molecular weight polylactide-glycolide containing unsaturated acrylate groups which can be activated in situ by the addition of a chemical activating agent (e.g., a peroxide or azo compound) and/or the addition of energy (e.g., electromagnetic (light), heat, ultrasound, etc.).

Exemplary Putties

Hydroxyapatite (HA) is an ideal filler for use with a polymer resin to form a moldable putty because of its low cost, radiopaque properties and osteoconductive properties. Although the examples below include HA (hydroxyapatite) as the fillers, those having ordinary skill in the art would understand that other forms of calcium phosphate may be used. As examples, other apatites, calcium phosphates, orthophosphates, monocalcium phosphates, dicalcium phosphates, tricalcium phosphates, whitlockite, tetracalcium phosphates, amorphous calcium phosphates may be substituted for HA. The filler particles may also be composites, e.g., particles of polymer and calcium phosphate materials such as HA.

In the examples that follow, a porous and hand moldable putty is provided from a polyurethane resin and an HA filler. However, resins other than polyurethane may be employed as discussed above. The putties form a porous scaffold across a fracture site that cures in situ at body temperatures. By varying the amount of filler and optionally utilizing one or more porogens and/or blowing agents, the properties of the putty can be customized to a particular application or injury.

The particle size range of HA can range from about 5 μm to about 4000 μm. However, in the examples that follow, the HA was sieved to particle sizes from about 10 μm to about 2800 μm. The HA content of the resulting putties ranged from about 15 wt % to about 80 wt %. Using different particle sizes and amounts of HA, or various size distributions of HA, it was found that the porosity and compressive properties of the putties can be manipulated for the injury being treated.

For example, increasing the amount of the 10 μm particle size HA (i.e., the "first" filler) will increase the compressive strength of the putty and will eventually lower the porosity of the putty. To provide a balance between compressive strength and porosity, a combination of small particle or 10 μm particle HA and large particle or 800- and 2800 μm HA (i.e., as "second" and possibly "third" fillers) may be utilized.

Other samples use a blowing agent as well as HA filler in the formulation. A blowing agent will aid in the creation of open cell porosity by rapidly off gassing in the resin to form bubbles. The blowing agent used was $H_2O$, which off gasses carbon dioxide. However, other blowing agents will be apparent to those skilled in the art. This and the combination of adhesive particles also yield hand moldable putty that is porous.

Lastly, 10 μm size HA was used as filler with a porogen in the form of mannitol, from SPI Pharma Inc. of Wilmington Del. (http://www.spipharma.com/). The mannitol not only acts as a porogen but also appears to reinforce the compressive strength of the putty until it degrades leaving void spaces in the putty. The mannitol porogen used has a sieve size ranging from about 170 μm to 1900 μm. These voids are connected resulting in open celled porosity because of the contact between the mannitol particles.

The addition of porogens and the employment of particle size manipulation can provide homogenous porosity values.

Fast dissolving porogens include, but are not limited to mannitol, calcium sulfate and other salts and sugars. In contrast, a discrete amount of putty or resin may be mixed with loose particles of a solid material, such as calcium phosphates, in order to stick the loose particles together but not fill all the spaces between them, which results in a porous putty. The solid particles may be of the same material, such as fast or slow resorbing materials or may include biologically active or non-active materials.

Once the resin is mixed, the HA particles, optional mannitol and optional water are added and blended with the resin mixture at room temperature. The resin will typically cure or set at body temperature.

TABLE 1

Weight Percent Formulation of Samples

| Sample No. | Resin (wt %) | 10 μm HA particles (wt %) | 0.8 mm-2.8 mm HA particles (wt %) | Ratio of 0.8-1.8/1.8-2.8 mm HA particles | 170 μm-1.9 mm mannitol particles (porogen) (wt %) | $H_2O$ (blowing agent) (wt %) |
|---|---|---|---|---|---|---|
| I | 29.4 | 0 | 70.6 | 13:11 | 0 | 0 |
| II | 25.0 | 15 | 60.0 | 13:11 | 0 | 0 |
| III | 23.3 | 14 | 62.8 | 16:11 | 0 | 0 |
| IV | 45.5 | 54.5 | 0 | n/a | 0 | 0 |
| V | 24.7 | 14.8 | 59.3 | 13:11 | 0 | 1.2 |
| VI | 43.5 | 17.4 | 0 | n/a | 39.1 | 0 |

TABLE 2

Mechanical Results

| Sample No. | Compression (MPa; Mean) | Porosity (%) | Connectivity (%) |
|---|---|---|---|
| I | 12 | 34.3 | 99 |
| II | 12 | 15 | 95 |
| III | 6 | 31 | 99 |
| IV | 20 | 24 | 97 |
| V | 3 | 33 | 99 |
| VI | 19 | n/a | n/a |

As shown above, Samples I-VI provided various values for compressive strength, which were generated using an aqueous compression test method. The method includes conditioning the sample for 24 hours in a phosphate buffered saline (PBS) solution at 37° C. (body temperature) before compression testing. The samples were dimensioned by casting the samples in a PTFE split mold (a right cylinder with the length at twice the diameter (24 mm×12 mm)) for 15 minutes at room temperature, in accordance with ASTM D695. Next, the samples were removed from the mold and conditioned at 37° C. for two hours then placed in the PBS solution.

After being conditioned for 24 hours in solution, the samples were tested using the MTS 150 screw machine. The test speed of the screw machine was at 1 mm/min, which is in compliance with ASTM D695. A 5 KN load cell was used to measure stress. Most of the compression test samples were greater than or equal to cancellous bone, which is about 10 MPa according to McCalden et al., *JBJS,* 1997, vol. 79, pp. 421-427. Three repetitive tests were conducted in the results averaged and listed in Table 2.

Samples I-VI were also tested for porosity and pore connectivity using a μCT machine. By using this machine, cross sectional images can be taken to measure cell formation. See Table 2 for porosity results.

Unlike other resorbable resins, the above samples exhibit a porosity that is created by using varying filler particles of varying sizes, porogens and/or blowing agent. Also the samples remained moldable by hand with the properties of being drillable and radiopaque after cure.

The disclosed putties may include one or more antibiotics, one or more antimicrobials for fighting infection. The disclosed putties may also include osteoconductive additive such as one or more bone morphogenetic proteins (BMPs). The resin of the disclosed putties may include components that are not degradable or resorbable such as reinforcing fibers. The disclosed resins may also be ultraviolet (UV) light curable or cross-link curable. In addition to polyurethane, other in situ hardening or curing materials can be used, e.g., polypropylene fumerate.

By using various amounts and particle sizes of filler, e.g., HA, drillable, moldable and osteoconductive putties are disclosed that can be remodeled by bone. The different size filler particles along with varying amounts of filler also result in improved compressive strength. The disclosed putties provide the surgeon more control of the pore size. The disclosed putties may be hand deliverable by the surgeon and do not require special injection devices.

The putty may incorporate a calcium phosphate mixture formed by first soaking conventional hydroxyapatite (HA) powder (such as a commercially available HA powder having an average particle size of about 45 to about 125 μm) in a silver nitrate-containing and/or silver fluoride-containing aqueous or organic solution for a period of time. The aqueous or organic solution may comprise both silver fluoride and silver nitrate. Beta tricalcium phosphate may be substituted for HA or HA may be combined with beta tricalcium phosphate. The calcium phosphate mixture includes about 0.1 percent to about ten percent by weight of silver. The calcium phosphate mixture may include about 0.5 percent to about three percent by weight of silver. One or more of carbonate, fluoride, silicon, magnesium, strontium, vanadium, lithium, copper, and zinc may be added to the calcium phosphate mixture.

The disclosed fracture putties may be curable in vivo and may be designed to closely match the mechanical (stress/strain—in tension, compression, bending, and torsion) and structural properties of natural bone. In general, the disclosed fracture putties provide initial fracture fixation, followed by full load-bearing capability for patient ambulation and create an optimal mechanical environment in the form of a scaffold structure which promotes natural bone regrowth or ingrowth, including within large gaps between bone segments. The disclosed fracture putties may be intrinsically non-toxic and non-antigenic, and may degrade into harmless resorbable by-products, and/or be resorbed by osteoclasts, the body's bone-dissolving cells, as bone regenerates, thereby transferring load-bearing to bone over time. The disclosed fracture putties may be compatible with, and infusible by, existing osteoinductive bone pastes, bone morphogenetic proteins, growth factors, antibiotics, antimicrobials, non-degradable components, ultraviolet (UV) curable cross linkers, etc.

In general, the procedure for fracture treatment using a disclosed putty includes the following steps: (1) reduce fracture; (2) make an entry point, which may be collinear with the axis of the bone or oblique to the axis of the bone; and (3) apply putty in the IM canal across the fracture to achieve adequate fixation on either side of the fracture. The procedure may also include preparing the canal. This may be accomplished with a standard reamer or a reamer with an expandable cutting head. The procedure may include inserting an additional device into the intramedullary canal and/or across the fracture as described in FIGS. 1-3, 5, 7, 9-13, 16, 19-21, 23-24 and 28-30.

The putty or resin may contain a reinforcing element, such as fibers or a particulate. Fibrous reinforcing materials include, but are not limited to, ceramic fibers or whiskers, polymeric fibers and metal fibers, for example, fibers made from magnesium and its alloys are degradable. Polymer materials may include, but are not limited to, homopolymers and co-polymers of PET, PP, PE, Nylon, PEEK, PLA, and PGA. Particulate reinforcing material may be in the shape of plates or rods. Examples include clays, micas, alumina, hydroxyapatite, calcium carbonate, calcium phosphates, and zirconia.

Some of the disclosed putties have a strength of at least 200 MPa, while others have a strength of at least 500 MPa.

It is particularly advantageous if the void filler bonds to the exposed bone within the defect. The void filler may also comprise an allogenic or autologous bone graft material. The void filler may also comprise a particulate or granular bone substitute material such as JAX™ (Smith & Nephew, Inc). Depending on the type of void filler used, additional strength properties may be conferred up the system.

Alternatively, one or more rods, pins or tubes of a stiff material may be placed into the intramedullary canal, which are then anchored in place by injection or insertion of the putty or resin. Examples of the stiff materials include metals, ceramics and polymers. With polymers the stiffness could be enhanced by preparing orientated rods, such as by die drawing. Another example is the use of composite materials for the rods, such as a PEEK/carbon fiber composite or degradable PLLA fiber composites.

Further, as noted below, a braided, woven or knitted sleeve may be placed into the intramedullary canal and impregnated with the putty or resin. The sleeve may be made from a resorbable or non-resorbable material. The sleeve may include a radio-opaque marker. The sleeve may be compressed radially or stretched axially via instrumentation for insertion, such that when inserted and released, it can expand to conform to the dimensions of the intramedullary canal. The sleeve may be made from resorbable fibers, such as PDLA.

Also, as noted below, a bag or balloon may be used to fill the intramedullary canal and filled with the putty or resin. When the device is pressurized and expands it engages into the endosteal wall to fixate the device via friction. An adhesive may be applied to the outer surface of the bag so that it will adhere to the endosteal wall after placement, thereby enhancing fixation. The bag/balloon device may have some porosity to allow the putty or resin to perfuse/leach to enable it to adhere to the endosteal wall. There may be a section in the central region of the bag/balloon that contains no porosity to prevent leakage of the putty or resin into the fracture gap. The bag or balloon may alternatively have reinforcing ribs or rods attached to either its inner or outer surface.

A bag or balloon may also be used to fill the intramedullary canal and filled with a pressurized liquid and then sealed. This has the advantage that the liquid can be removed at a later date to facilitate removal of the device. Alternatively, the liquid may reversibly solidify, such as polycaprolactone or a thermo-reversable gel.

FIGS. 1-29

Referring to the accompanying drawings in which like reference numbers indicate like elements, FIG. 1 illustrates a bone 100 with fracture 102 and a system 10 for fracture repair. The system 10 includes a hardenable putty 12 and a fixator 14 inserted into the intramedullary canal. The putty 12 may be made of a polyurethane material having embedded ceramic particles, chopped fibers and/or HA particles. Further, in FIG. 1, the fixator 14 may be a braided sleeve made from poly-L-lactide (PLLA) fibers and impregnated with polyurethane resin. The sleeve may be impregnated in vivo. The fixator 14 may also include axial channels or a cannulation.

In FIG. 1, the fixator 14 is illustrated as engaging the endosteal or cortical wall of the bone 100. Alternatively, the fixator 14 may be sized to allow for blood flow between the endosteal wall and the fixator 14. The fixator 14 may be pinned or fastened on each side of the fracture 102 to connect the bone segments. For example, resorbable screws may be used to fasten the fixator 14 to the bone 100.

In another embodiment, the putty 12 is replaced by a resorbable metal spacer formed as a monolith with a central axial bore that accommodates the fixator 14. Additional resin or putty may be used to fill any cracks or voids.

Figure 2:
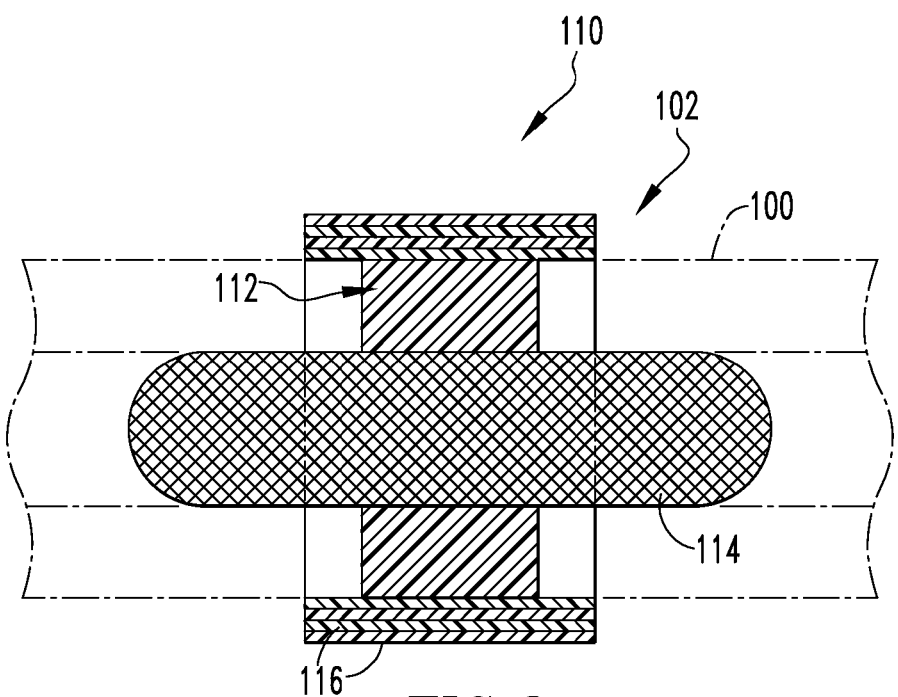
FIG. 2 is a cross-sectional view of a fracture with another disclosed internal fixation system.

FIG. 2 illustrates the bone 100 having the fracture 102 and a system 110 for fracture repair. The system 110 includes a resorbable and hardenable putty 112, a fixator 114, and a hardenable tube 116. In FIG. 2, the fixator 114 may be a braided sleeve (see also FIG. 31) made from PLLA fibers or a spacer fabric (see also FIGS. 32 and 32A) made from PLLA and impregnated with the resorbable and hardenable putty 112, or a hardenable and resorbable polyurethane resin. The sleeve may be impregnated in vivo. The tube 116 may be made from a shape memory material, such as a shape memory polymer. The tube 116 may be constructed and arranged such that the tube 116 has a first size before implantation but changes to achieve a second size after implantation based upon the shape memory effect. Alternatively, the fixator 114 may include axial channels or a cannulation.

Figure 3:
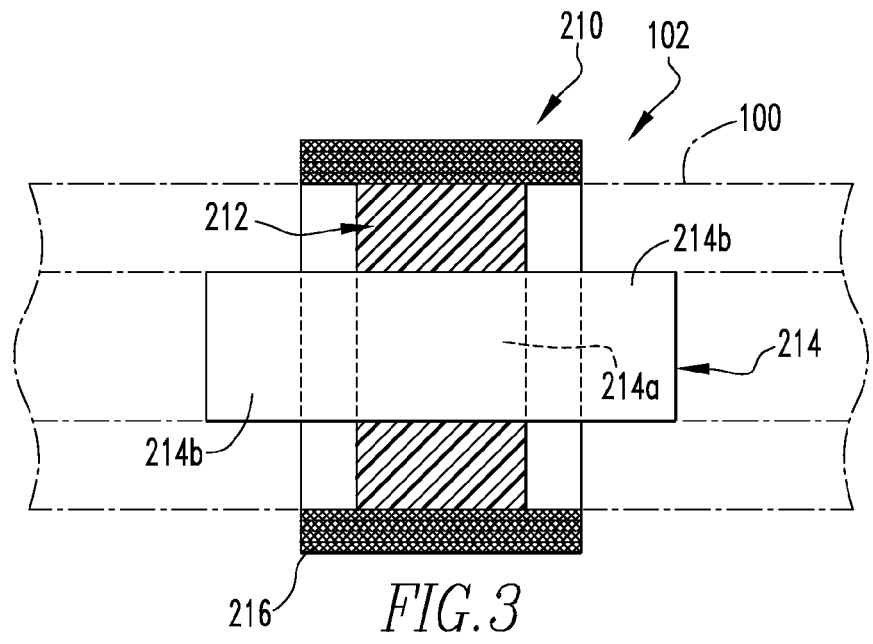
FIG. 3 is a cross-sectional view of a fracture with another disclosed internal fixation system.

FIG. 3 illustrates the bone 100 having the fracture 102 and a system 210 for fracture repair. The system 210 includes a resorbable putty 212, a fixator 214, and a wrapping 216. Wrapping 216 is made from a mesh material impregnated with a putty or resin, such as polyurethane resin. The wrapping 216 may be impregnated in vivo. The fixator 214 is made from a resorbable material, such as a shape memory polymer. The fixator 214 may include axial channels or a cannulation.

In FIG. 3, the fixator 214 may comprise a degradable scaffold section 214a disposed between degradable internal splint sections 214b. The degradable scaffold 214a may be more porous and may be provided in the forms of injectable gels, resins, or preformed structures. The wrapping 216 may be in the form of a degradable tissue guided scaffold and optional incorporation of an active material such as an antibiotic, steroid, etc. The internal splint sections 214b may be made of resorbable fibers impregnated with an in-situ settable resin. The tissue guided (TGS) scaffold 216 may be placed round the defect direct cell growth and to act as a retaining mechanism for soft gels, resins, loose particulates or cements. The TGS 216 may be porous to encourage tissue ingrowth. In one embodiment, the TGS 216 is a body temperature activated shape memory split tube which activates and tightens around the bone 100. The TSG 216 may have pores in the range of about 35 μm to trap macrophages which then cause cells to liberate cell signaling molecules and resulting tissue repair. The gel, putty or paste 212 can be composed of gelling materials such as PLAGA granules, hylaronic acid, light curable materials such as polylactide-based macromers, collogen, gelatin, chitosan sponge, calcium sulphate, in situ setting ceramic cement, etc.

Figure 4:
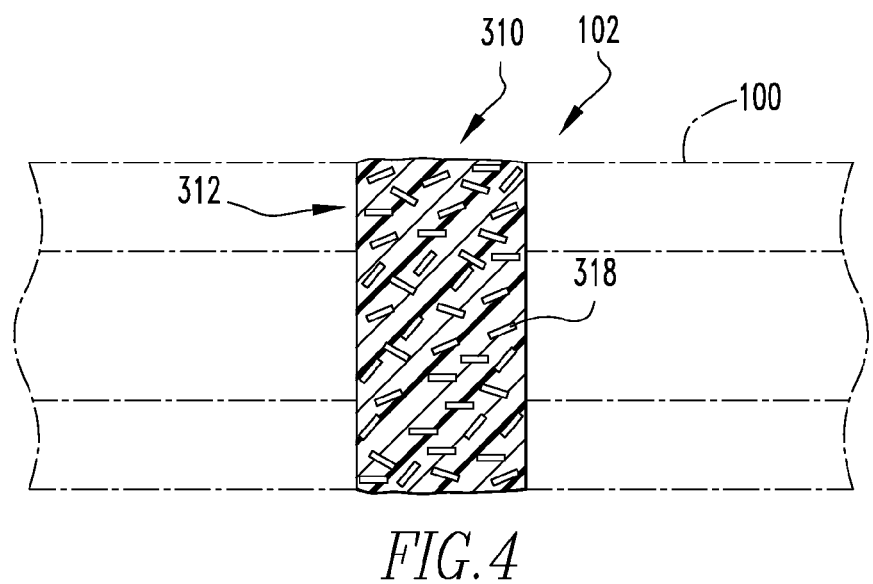
FIG. 4 is a cross-sectional view of a fracture with another disclosed internal fixation system.

FIG. 4 illustrates the bone 100 having the fracture 102 and a system 310. The system 310 includes a hardenable putty 312 and a plurality of ceramic channels or chopped fibers 318. The hardenable putty 312 may be polyurethane resin and HA particles or another suitable filler. If the fracture 102 is sufficiently small, the putty or resin 312 may be merely polyurethane resin. As examples, if channels 318 are employed, the channels 318 may be tubes, plates, or cones. The putty 312 and the ceramic channels or chopped fibers 318 may be mixed together and placed in the fracture 102. For example, the putty 312 and the chopped fibers or ceramic channels 318 may be shaped into a cylinder. Once the putty cylinder 312 is placed in the fracture 102, the fracture 102 and adjacent area may be wrapped to add strength and hold the putty 312 in place. As examples, the fracture 102 may be wrapped with a resorbable material, a putty or resin, a woven resorbable material, or a woven material impregnated with a foam or non-foam putty or resin.

Figure 5:
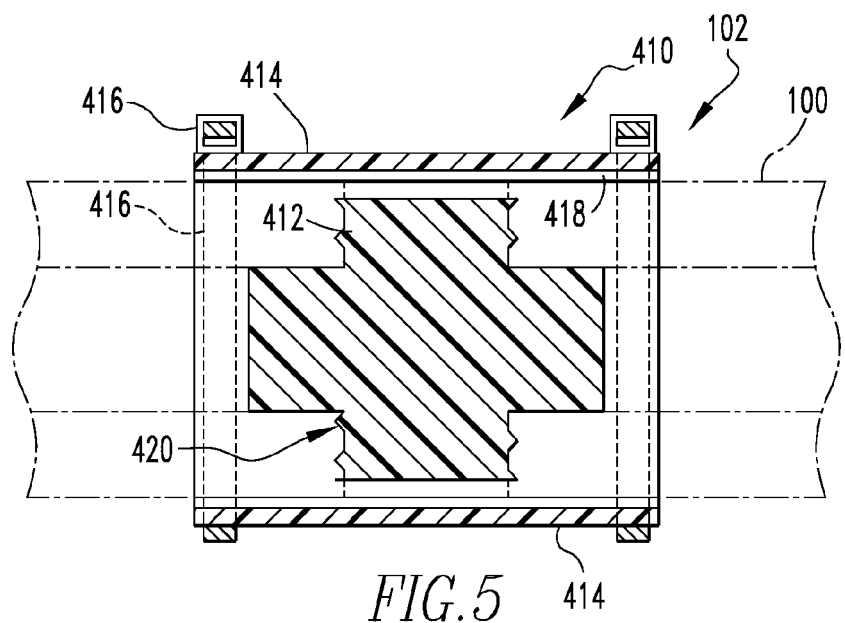
FIG. 5 is a cross-sectional view of a fracture with another disclosed internal fixation system.
Figure 6:
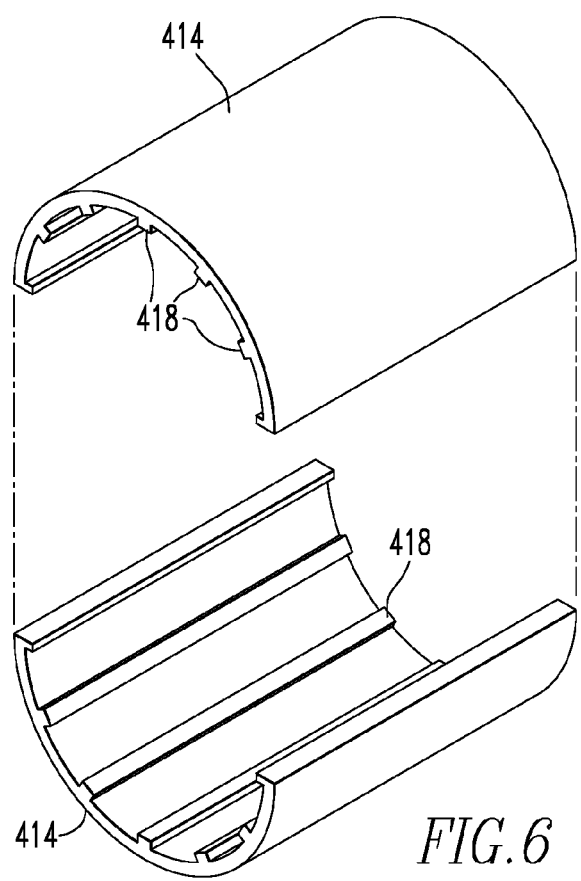
FIG. 6 is a perspective view of the collar used in the system of FIG. 5.

FIGS. 5-6 illustrate the bone 100 having the fracture 102 and a system 410. The system 410 may include a balloon 412, a collar pair 414, and at least one band 416. The balloon 412, the collar pair 414, and at least one band 416 all may be made from a resorbable material. The balloon 412 expands in multiple directions. Thus, in FIG. 5, the balloon 412 expands into the intramedullary canal and into the segmental defect. Portions of the balloon 412 may include a gripper 420 for gripping the endosteal wall or other portions of bone. The balloon 412 may be filled with a putty or resin, such as a polyurethane resin. As best seen in FIG. 6, the collar pair 414 may include structural ribs 418. The balloon 412 may include axial channels or a cannulation to allow for blood flow.

Alternatively, the balloon 412 may be replaced with putty or resin, and the collars 414 replaced with tubular structures that are held in place by the bands or clamps 416.

Figure 7:
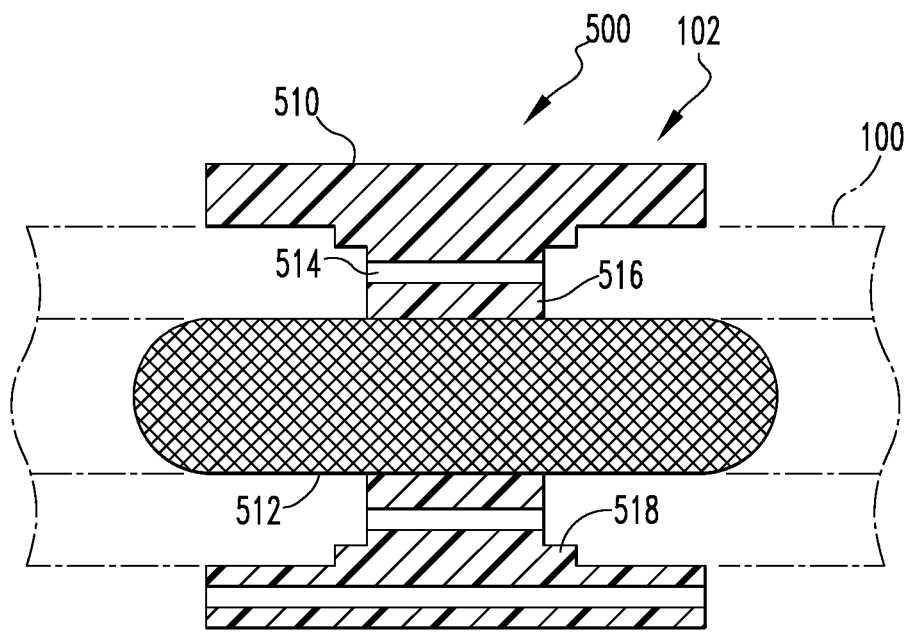
FIG. 7 is a cross-sectional view of a fracture with another disclosed internal fixation system.
Figure 8:
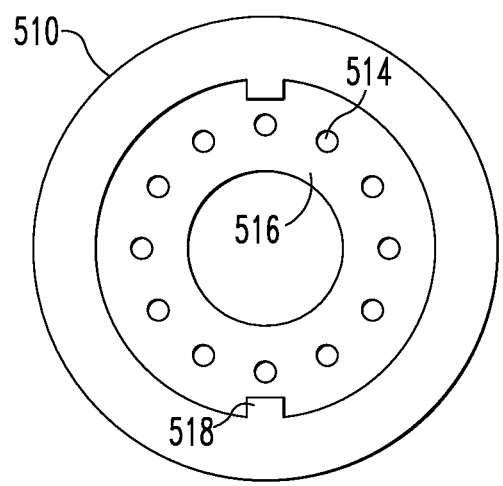
FIG. 8 is an end view of the connector used in the internal fixation system of FIG. 7.

FIG. 7 illustrates the bone 100 having the fracture 102 and a system 500 for fracture repair. The system 500 includes a collar 510 and a fixator 512. The collar 510 is made from a porous shape memory material. The fixator 512 may be a pre-formed part and may be impregnated with a putty or resin such as a polyurethane resin. As best seen in FIG. 8, the collar 510 is generally cylindrical and includes peripheral passages 514, a second face 516, and tabs 518. The passages 514 may be cylindrical and allow for bone in-growth. The tabs 518 engage the bone surface to substantially prevent rotation of the bone segments. The fixator 512 may also include axial channels or a cannulation.

FIG. 9 illustrates the bone 100 having the fracture 102 and a system 600 for fracture repair. The system 600 includes a first putty or resin 610, a second putty 612, and a third putty 614. The first, second and third putties 610, 612, 614 may be hardenable and/or resorbable and the porosity and compressive strength may be varied as disclosed above, depending upon the particular injury and patient condition.

FIG. 10 illustrates the bone 100 having the fracture 102 and a system 700 for fracture repair. The system 700 includes a fitting 710. The fitting 710 may be T-shaped or Y-shaped. The fitting 710 may be formed of a single component or from two members spliced together. The fitting 710 may be filled with a putty or resin. The fitting 710 may be made of a braided material. A resorbable putty 712 may be packed around the fitting 710. The resorbable putty 712 may be porous. After the fitting 710 is placed into the intramedullary canal, a portion of the fitting 710 may be snipped or broken off. The fitting 710 may be made of a resorbable material. FIG. 10A illustrates another fitting 710a with arrow-shaped or barbed ends 710b. The ends 710b may be threaded. The fitting 710a may be made of a resorbable material.

Figure 11:
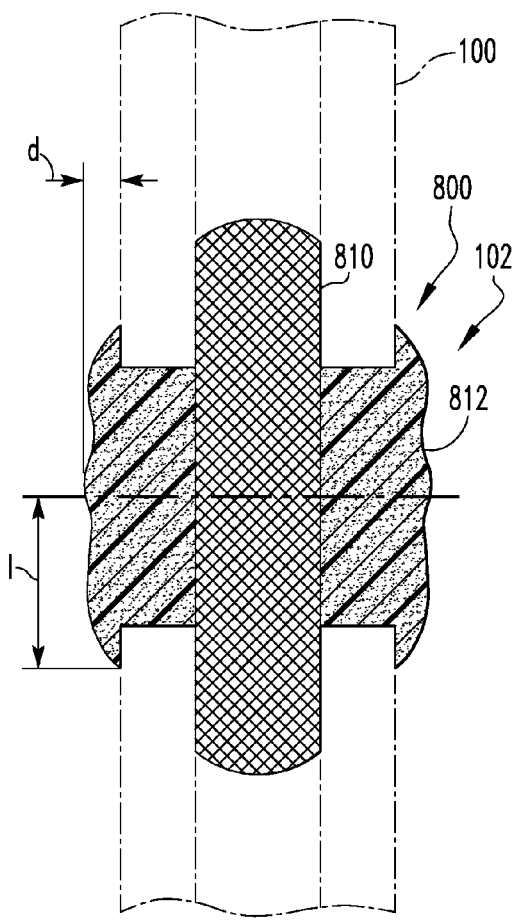
FIG. 11 is a cross-sectional view of a fracture with another disclosed internal fixation system.

FIG. 11 illustrates the bone 100 having the fracture 102 and a system 800 for fracture repair. The system 800 includes a reinforced resin or putty 810 for mechanical strength and a hardenable and resorbable putty 812. The putty 812 may be porous for bone ingrowth. The dimensions "d" and "l" may be controlled depending upon the size of the fracture site. The reinforced putty or resin 810 may include axial channels or a cannulation.

Figure 12:
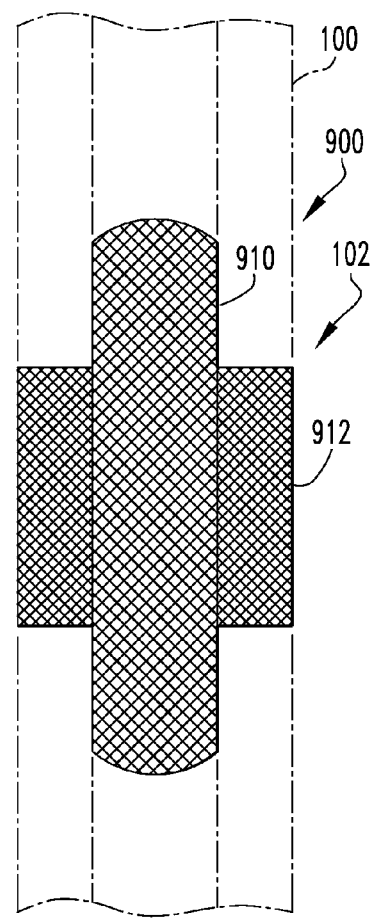
FIG. 12 is a cross-sectional view of a fracture with another disclosed system.

FIG. 12 illustrates the bone 100 having the fracture 102 and a system 900 for fracture repair. The system 900 includes a fixator 910 made of a resin and a braided mesh wrap 912 impregnated with the resin. The resin may be applied as a foam. The braided mesh may provide a porous scaffold. The fixator 910 may include axial channels or a cannulation.

In any of the above-examples, the endosteal surface of the intramedullary canal may be rifled or spirally cut to improve torsional strength. In any of the above examples, the system may include a guided tissue regeneration membrane. The guided tissue regeneration membrane may be placed between soft tissue and the fracture repair device. As examples, the membrane may be placed between soft tissue and the putty or resin, between the soft tissue and the resorbable material, between the soft tissue and the wrap, between the fixator and the soft tissue, or the membrane may be used in place of the wrap. The membrane prevents soft tissue from growing into the fracture repair device but does allow for bone in-growth. As an example, guided tissue regeneration membrane may be BIO-GIDE® Resorbable Bilayer Membrane. BIO-GIDE is a registered trademark of Osteomedical Ltd. of Parliament Street 14-16, Dublin, Ireland. The guided tissue regeneration membrane may be coated with silver or silver salt for antimicrobial purposes.

Figure 13:
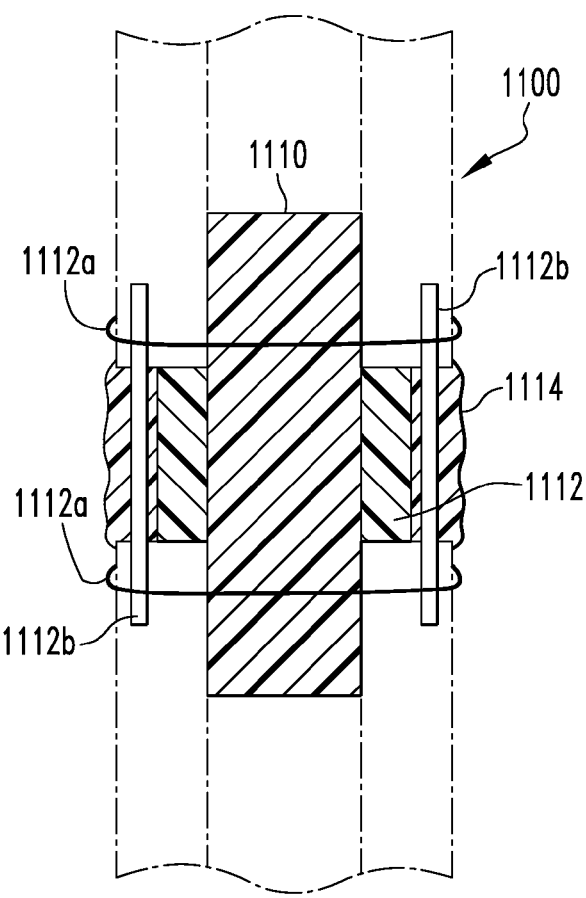
FIG. 13 is a cross-sectional view of a fracture with another disclosed system.

FIG. 13 illustrates another system 1100 for fracture repair. The system 1100 includes a fixator 1110, an optional support 1112 (see also FIG. 14), optional sutures 1112a and optional rod-like supports 1112b. The fixator 1110 may be made of a solid material, a porous material, a braided material, or some combination thereof. In one embodiment, the fixator 1110 is a press-fit rod made from resilient plastic. The system 1100 may also include a hardenable and resorbable putty 1114. The optional support 1112 may be generally cylindrical, oval, C-shaped or U-shaped. The support 1112 may be made from a porous material, a high strength resorbable material, or magnesium. The support 1112 may be made from a shape memory foam. The support 1112 may be placed within the fracture gap or segmental defect to provide structural support between the bone ends. Several supports 1112 of different sizes and/or length may be contained within a kit, and a health care provider may select the appropriate size and/or length for the particular fracture gap or segmental defect from the kit. Another option is to use rod-like supports 1112b.

Still referring to FIG. 13, the fixator 1110 is typically placed in the intramedullary canal as shown. The fixator 1110 may be impregnated with a resin, such as a polyurethane resin or one of the alternatives described above. The support 1112 then may be placed between the bone segments and around the fixator 1110. In some embodiments, the putty or resin 1114 may be packed around the support 1112. In other embodiments, no supports 1112, 1112b are utilized and the putty or resin is packed around fixator 1110. In still other embodiments, resorbable sutures 1112*a* may be wrapped around the exterior of the bone to minimize rotation of the bone segments. The sutures 1112*a* may be employed with or without supports 1112, 1112*b*.

Figure 14:
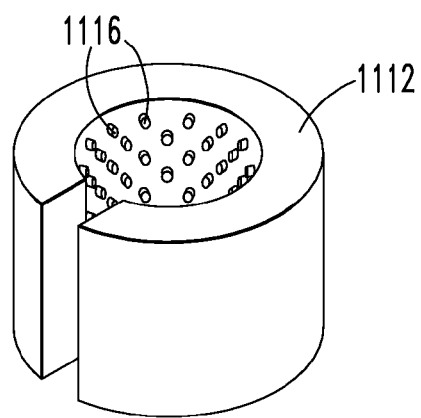
FIG. 14 is a perspective view of an inner ring of the system illustrated in FIG. 13.

FIG. 14 illustrates the support 1112 of the system 1100 of FIG. 13. Typically, the support 1112 is C-shaped and includes protrusions 1116 along its inner wall. The protrusions 1116 may be used to frictionally or mechanically engage the fixator 1110. Alternatively, the protrusions may be used to provide a space between the support 1112 and the fixator 1110. The protrusions 1116 may be randomly placed or placed in a pattern and may be omitted entirely. If used, the protrusions 1116 may have any shape. As examples, the protrusions 1116 may be cylindrical, square, triangular, or conical. In FIG. 14, the protrusions 1116 are cylindrical. The protrusions 1116 may have any length. For example, each protrusion 1116 may have a length in the range from about 0.1 mm to about 5 mm, and more preferably from about 0.5 mm to about 3 mm. In the depicted embodiment, each protrusion has a length of about 1.5 mm.

Figure 15:
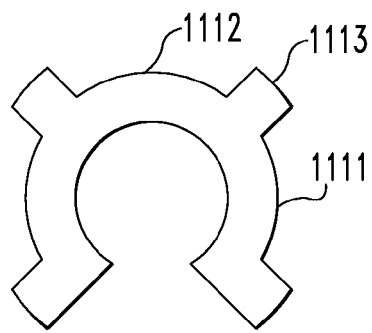
FIG. 15 is a top view of an alternative ring for the system of FIG. 13.

FIG. 15 illustrates an alternative to the support 1112 of FIGS. 13-14. In FIG. 15, the support 1112 has exterior spaces or gaps 1111 and radial protrusions 1113. The spaces 1111 may receive the putty or resin 1114.

Figure 16:
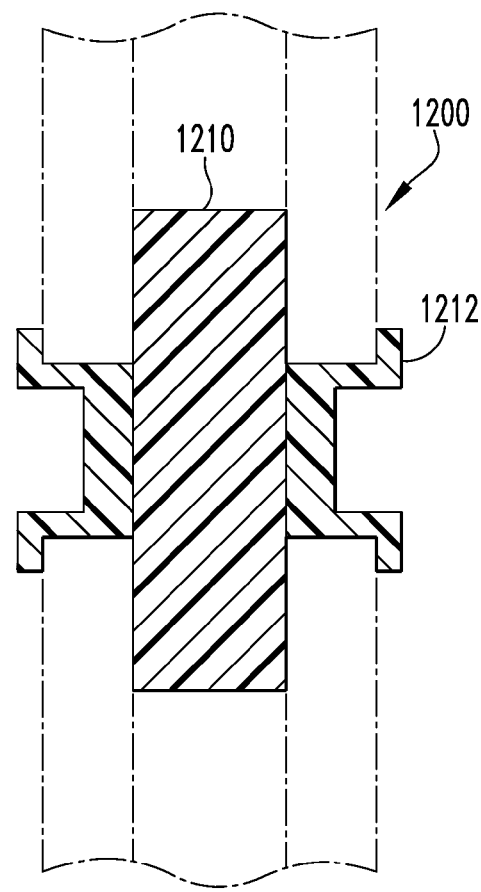
FIG. 16 is a cross-sectional view of a fracture with yet another disclosed system.

FIG. 16 illustrates another system for fracture repair 1200. The system 1200 includes a fixator 1210 and a plurality of supports 1212. The fixator 1210 may be made of a solid material, a porous material, a braided material, or some combination thereof. The supports 1212 may be spaced about the fracture gap or segmental defect. Any number of supports 1212 may be used. As an example, from about two to about eight supports 1212 may be used within the fracture gap or segmental defect. In FIG. 16, three supports 1212 are used (one of the supports is hidden by the fixator), each being about 120 degrees apart. The supports 1212 may be made from a porous material, a high strength resorbable material, such as a magnesium alloy. The supports 1212 may be made from a shape memory foam. The supports 1212 may be placed within the fracture gap or segmental defect to provide structural support between the bone ends. Several supports 1212 of different thickness and/or length may be contained within a kit, and a health care provider may select the appropriate thickness and/or length for the particular fracture gap or segmental defect from the kit. The system 1200 of FIG. 16 may also include a putty or resin (not shown) placed in-between and around the supports 1212.

In one method, the fixator 1210 is placed in the IM canal. The fixator 1210 may then be impregnated resin. The supports 1212 then may be placed between the bone segments and around the fixator 1210. One of the disclosed putties may be packed around the support 1212.

Figure 17:
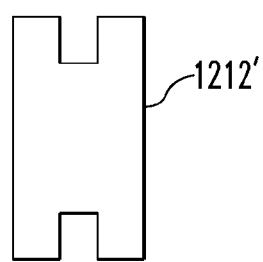
FIG. 17 is a plan of view an alternative support for the system shown in FIG. 16.
Figure 18:
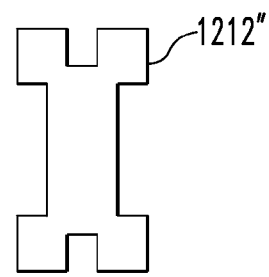
FIG. 18 is a plan view of other alternative support for the system of FIG. 16.

FIGS. 17 and 18 illustrate alternatives to the supports 1212 illustrated in FIG. 16. In FIG. 17, the support 1212' is H-shaped. In FIG. 18, the support 1212" is I-shaped.

Figure 19:
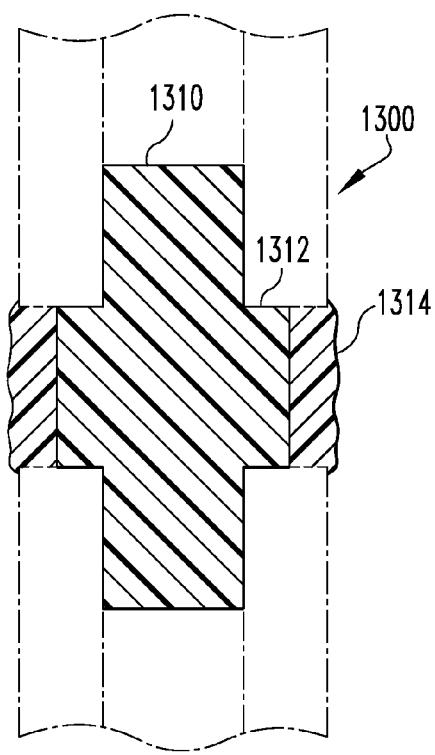
FIG. 19 is a cross-sectional view of a fracture with another disclosed system.

FIG. 19 illustrates another system 1300 for fracture repair. The system 1300 includes a fixator 1310. The fixator 1310 may be made of a solid material, a porous material, a braided material, or some combination thereof. As shown in FIG. 19, the fixator 1310 has intramedullary canal portion and a support portion 1312. The fixator 1310 may be unitary or integrally formed. The system 1300 may also include a disclosed putty 1314. The support portion 1312 may be generally cylindrical, oval, square, hexagonal, or some other shape. As also shown in FIG. 19, the support portion 1312 extends radially beyond the intramedullary canal to provide support to the bone segments. The support portion 1312 may be made from the same material as the fixator 1310 or a different material. As examples, the support portion 1312 may be made from a porous material, a high strength resorbable material, magnesium, or a shape memory material. Several fixators 1310 with support portions 1312 of different sizes and/or length may be contained within a kit, and a health care provider may select the appropriate size and/or length for the particular fracture gap or segmental defect from the kit.

Still referring to FIG. 19, in one disclosed method, the fixator 1310 is placed in the intramedullary canal and fixator 1310 is impregnated with resin. The putty 1314 may then be packed around the support portion 1312.

Figure 20:
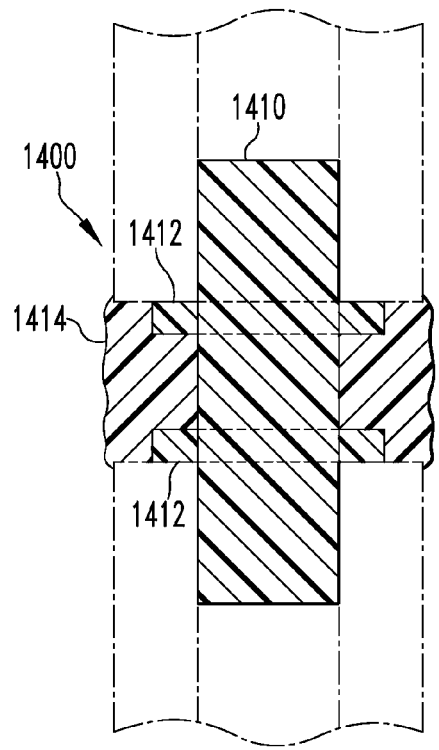
FIG. 20 is a cross-sectional view of a fracture with another disclosed system.

FIG. 20 illustrates yet another system 1400 for fracture repair. The system 1400 includes a fixator 1410 and at least two supports 1412. The fixator 1410 may be made of a solid material, a porous material, a braided material, or some combination thereof. In the depicted embodiment, there are two supports 1412, each one placed adjacent a bone segment. The system 1400 may also include a putty or resin 1414. The supports 1412 may be generally cylindrical, oval, C-shaped or U-shaped. As examples, the supports 1412 may be made from a metal, a non-resorbable material, a porous material, a high strength resorbable material, magnesium, or a shape memory material. The support 1412 may be placed within the fracture gap or segmental defect to provide structural support between the bone ends. The supports 1412 may be adapted to frictionally or mechanically engage the fixator 1410. The supports 1412 may be fastened to the fixator 1410 through the use of a fastener (not shown).

The supports 1412 may also include protrusions (not shown) along the fixator contacting surface, similar to the support 1112 of the FIG. 14. The supports 1412 of FIG. 20 may be arranged with a space in-between or stacked upon one another to substantially fill the fracture gap or segmental defect. While in FIG. 20 the supports 1412 appear parallel to one another, those having ordinary skill in the art would understand that the supports 1412 are more likely to be angled relative to one another with the particular angle dependent upon the size and shape of the particular fracture gap or segmental defect. Several supports 1412 of different size and/or thickness may be contained within a kit, and a health care provider may select the appropriate size and/or thickness for the particular fracture gap or segmental defect from the kit.

Still referring to FIG. 20, in one disclosed method, the fixator 1410 is placed in the IM canal. The fixator 1410 is impregnated with the putty or resin. The supports 1412 then may be placed between the bone segments and around the fixator 1410. The putty 1414 may be packed around the support 1412.

Figure 21:
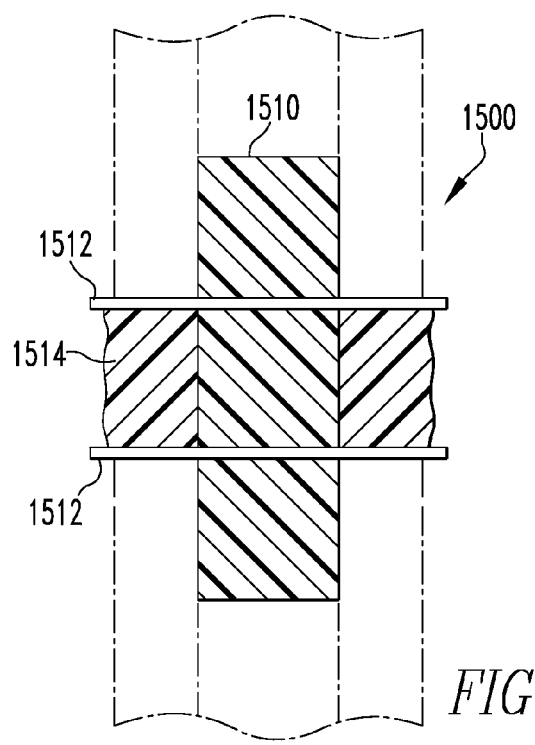
FIG. 21 is a cross-sectional view of a fracture with another disclosed system.

FIG. 21 illustrates another system 1500 for fracture repair. The system 1500 includes a fixator 1510 and at least two pin supports 1512. The fixator 1510 may be made of a solid material, a porous material, a braided material, or some combination thereof. As shown in FIG. 21, two pin supports 1512 are employed, each one placed adjacent a bone segment. However, those having ordinary skill in the art would understand that any number of pin supports 1512 may be used. The system 1500 may also include a putty or resin 1514. The pin supports 1512 may be generally cylindrical, square, hexagonal, or triangular. The pin supports 1512 may be provided in the shape of a fastener, such as a screw. As examples, the supports 1512 may be made from a metal, a non-resorbable material, a porous material, a high strength resorbable material, magnesium, or a shape memory material. The supports 1512 may be placed partially into or entirely through the fixator 1510. In one embodiment, four pin supports 1512 are employed in the form of two substantially diametrically opposed pairs, each pin support 1512 extending only partially into the fixator. While in FIG. 21, the pin supports 1512 appear parallel to one another, those having ordinary skill in the art would understand that the pin supports 1512 are more likely to be angled relative to one another with the particular angle dependent upon the size and shape of the particular fracture gap or segmental defect. Several supports 1512 of different thickness and/or length may be contained within a kit, and a health care provider may select the appropriate thickness and/or length for the particular fracture gap or segmental defect from the kit.

In one disclosed method, the fixator 1510 is placed in the intramedullary canal. The fixator 1510 may then impregnated with a resin. The supports 1512 may then be placed between the bone segments and through the fixator 1510. The putty 1514 may then be packed around the supports 1512.

Figure 22:
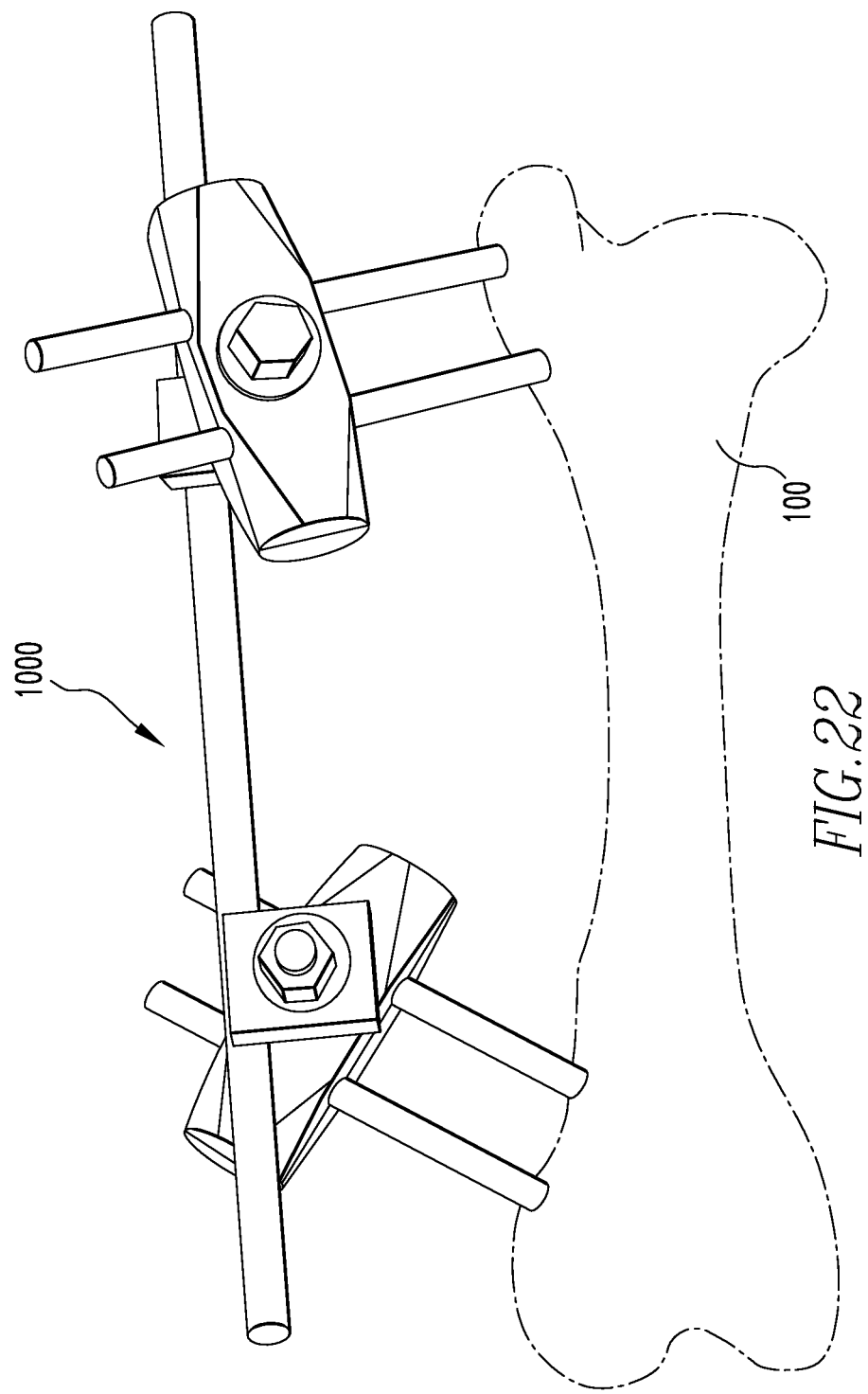
FIG. 22 schematically illustrates an external fixator attached to a bone.
Figure 23:
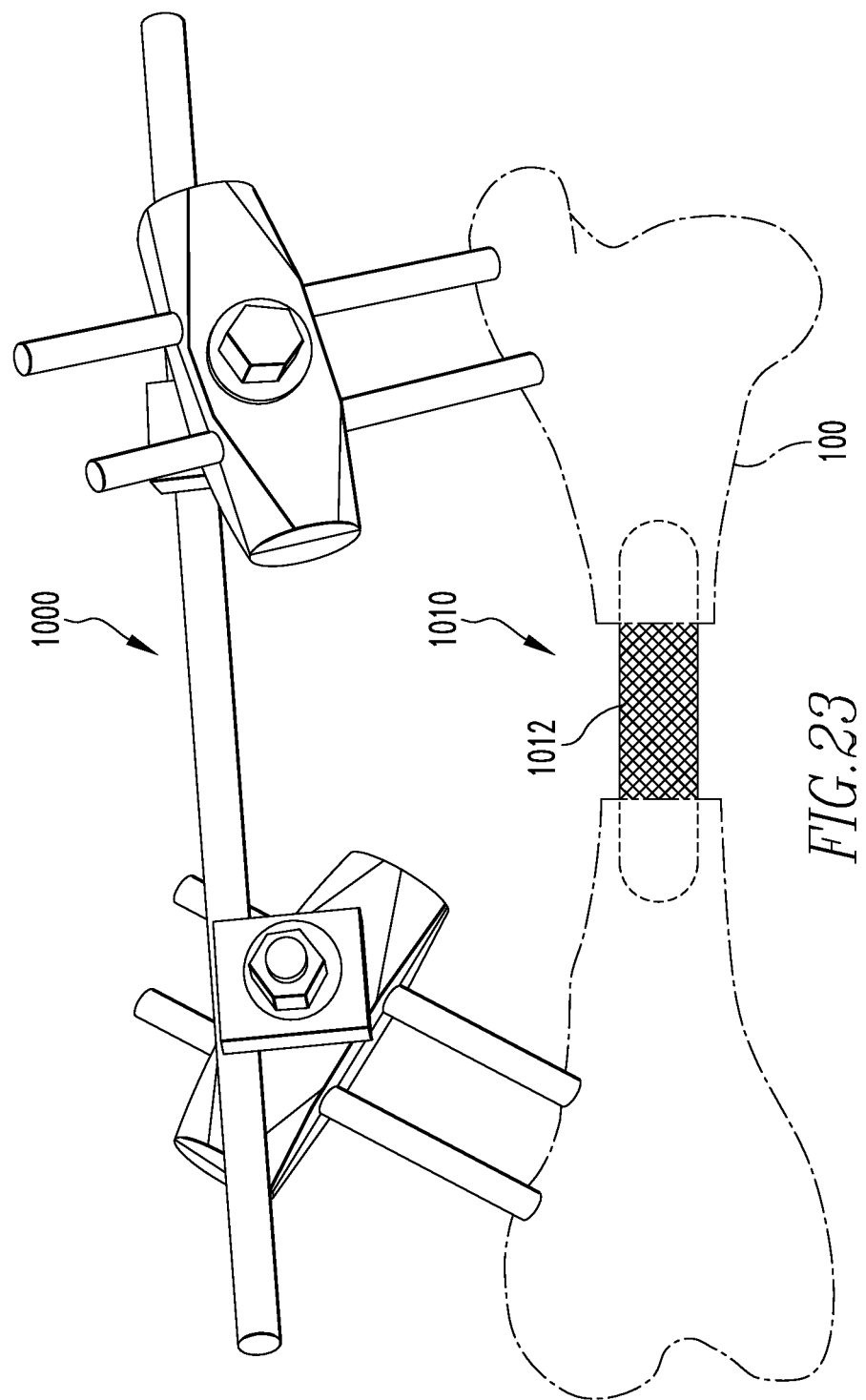
FIG. 23 schematically illustrates the external fixator of FIG. 22 attached to a bone with a segmental defect and a disclosed internal fixation system for fracture repair.

FIGS. 22-27 illustrate the use of the system for fracture repair. Although the system is illustrated in use on a sheep femur, the system is applicable to any mammalian bone. Referring now to FIG. 22, the bone 100 is first reamed. The intramedullary canal is reamed up to about 11.5 mm using a reaming tool. As best seen in FIG. 23, an external fixation device 1000 is then used to fixate the bone (to preserve bone alignment) while a segmental defect 1010 of about 25 mm is made in generally the mid-diaphyseal region using a hack saw. The segmental section 1010 of bone 100 is then removed and all remaining marrow and fat is removed from the intramedullary canal using cotton swabs (not shown). A braided sleeve or tube of space or material 1012 is then inserted into the intramedullary canal until the canal is completely filled and the segmental defect 1010 is bridged.

The sleeve 1012 may be a braid of PLLA fibers having an outside diameter of about 7 mm, and the sleeve 1012 may be previously heat-set to expand the sleeve to about 12 mm when deployed. The term "heat-set" refers to a process that sets the braid to a new diameter via a thermal treatment. What is significant is that the braid has a first diameter (in this case 12 mm) and recovers to the first diameter after stretching to achieve a second diameter (in this case 7 mm).

Figure 24:
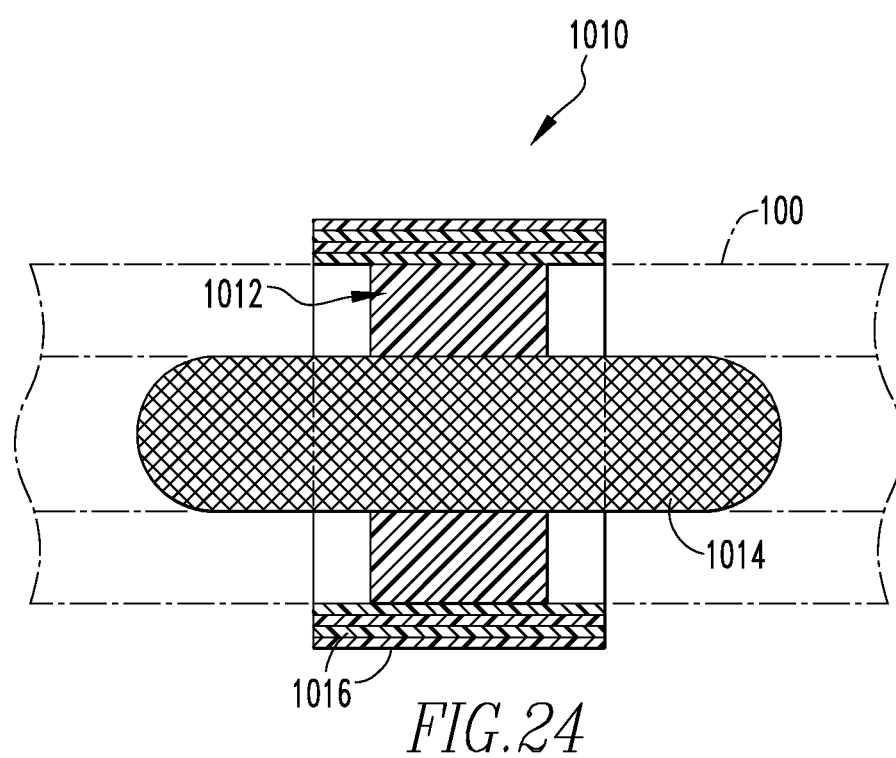
FIG. 24 is a schematic cross-section of a fractured bone with another disclosed internal fixation system.

Referring now to FIG. 24, a small section of resorbable mesh 1016 is then impregnated with a foaming formulation of polyurethane material and wrapped around the segmental defect section 1010 of the bone 100. The bone 100 is then placed in an oven at 37 degrees C. for approximately two hours to allow the polyurethane foam to fully set. The bone 100 is then removed from the oven and allowed to sit for about 8 to about 16 hours.

In about twenty-four hours, an injectable, non-foaming formulation of polyurethane material is injected into the braided sleeve 1012 in the bone's intramedullary canal. The braided sleeve 1012 may include axial channels or a cannulation to allow for blood flow. The polyurethane resin is filled to the top of the bone 100, and small leaks at the segmental defect section 1010 may be closed off to prevent loss of resin material. The bone 100 may be allowed to set for about 1 to about 4 days, e.g., for about two days, to allow full curing prior to potting for subsequent mechanical testing. Potting involves using a two-part PMMA dental bone cement mixed in a ratio of two-parts powder to one-part liquid. After potting, the bone 100 is allowed to sit for about 8 to about 16 hours.

Figure 25:
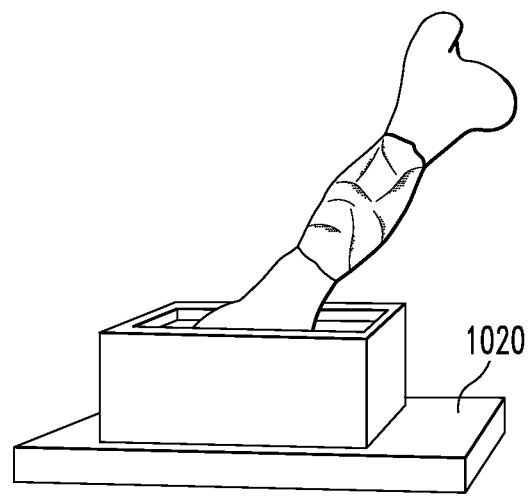
FIG. 25 is a perspective view of a bone used for mechanical testing.
Figure 26:
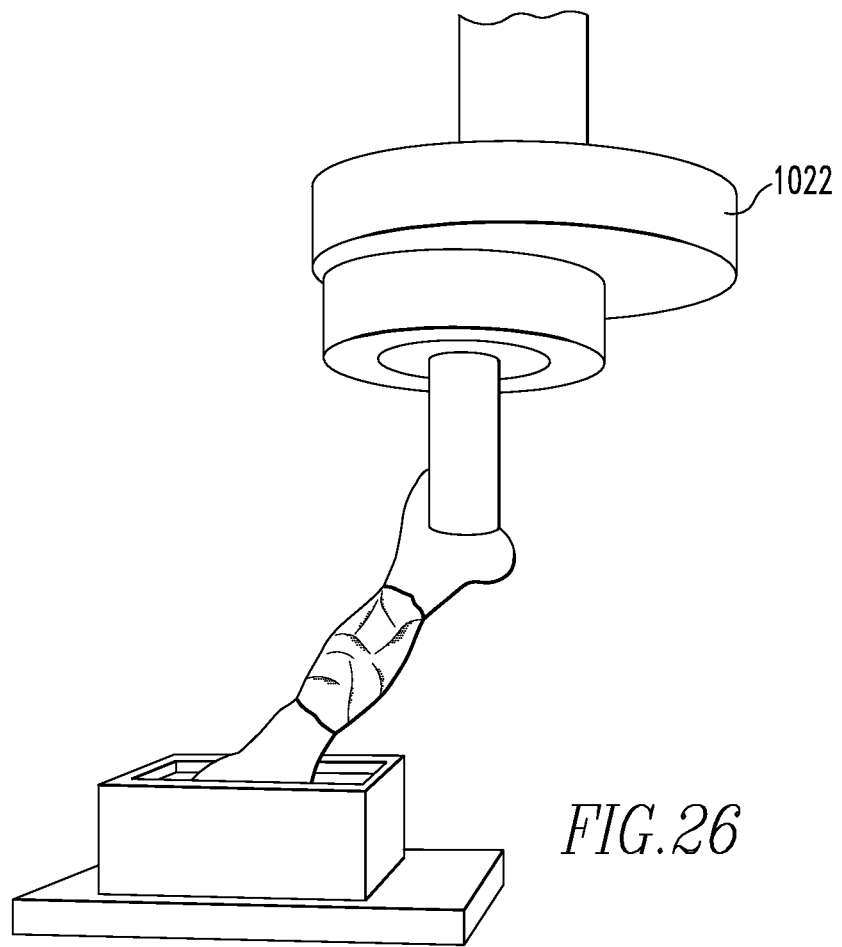
FIG. 26 is a perspective view of a mechanical testing device with the bone of FIG. 26.

As best seen in FIGS. 25-26, mechanical testing employs a bearing roller plate fixture 1020 that allows loading of a femoral head of the bone 100. The fixture is set up such that only the femoral head is in contact with the fixture during displacement of a crosshead 1022. A simple compression method is used with a strain endpoint of 100%. Load is applied at a speed of about 5 mm/min. until failure of the construct.

Figure 27:
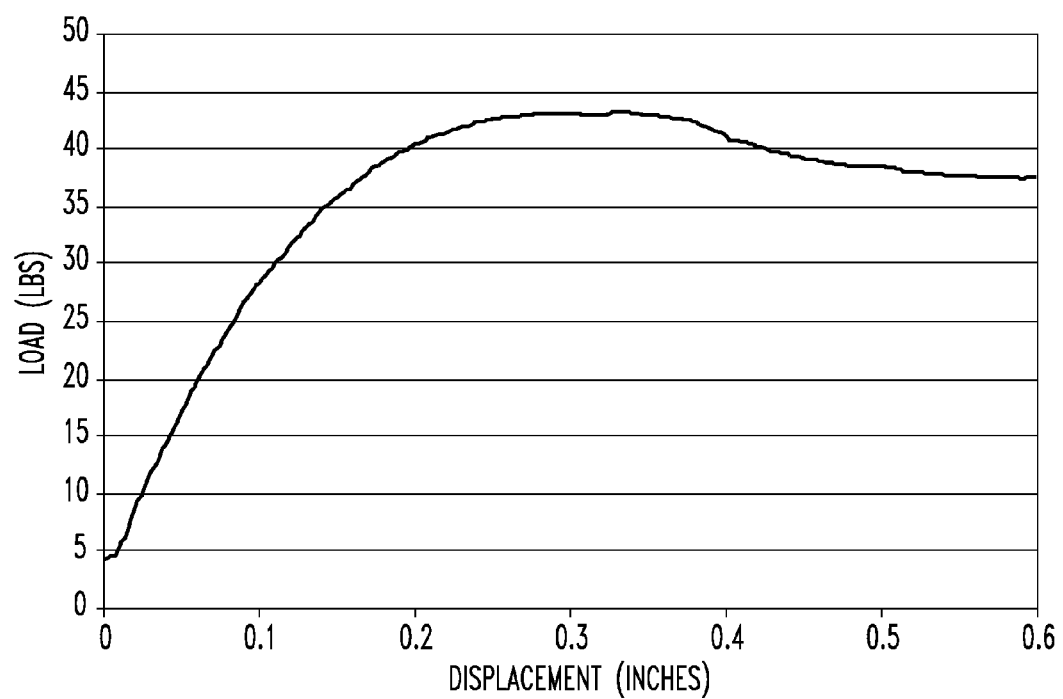
FIG. 27 graphically illustrates exemplary results of a mechanical test.

FIG. 27 illustrates one example of the results of mechanical testing. In the graph shown in FIG. 27, the maximum load achieved is approximately 30-50% of normal weight bearing. During testing, failure appears to be in bending only and not achieved by torque failure. The shape of the intramedullary canal when filled with the polyurethane-impregnated braided sleeve 1012 may prevent rotation of the relative bone segments. The failure appears to be ductile, which is significant as it avoids a catastrophic failure. Ductile failure is preferred because if a device is overloaded, it will bend rather than shatter.

Figure 28:
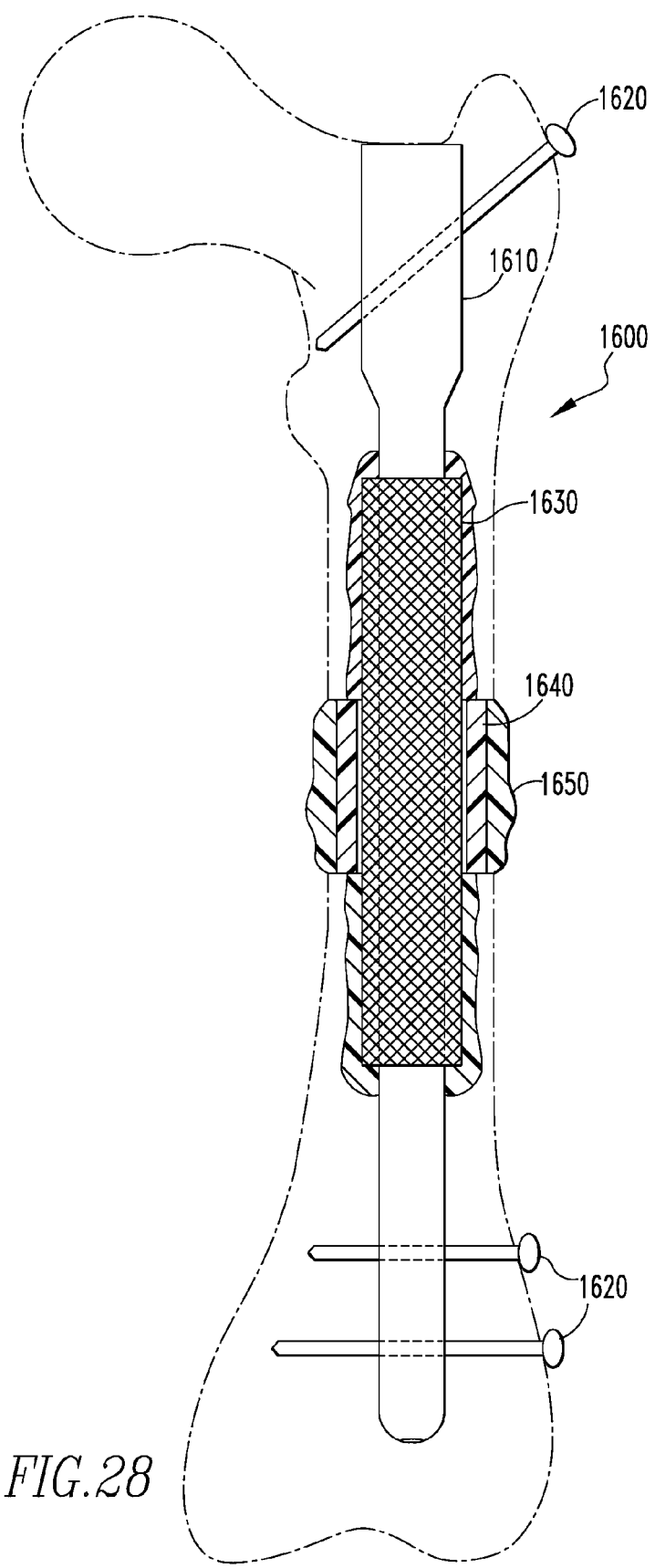
FIG. 28 schematically illustrates an internal fixation or system for use with an intramedullary nail.
Figure 29:
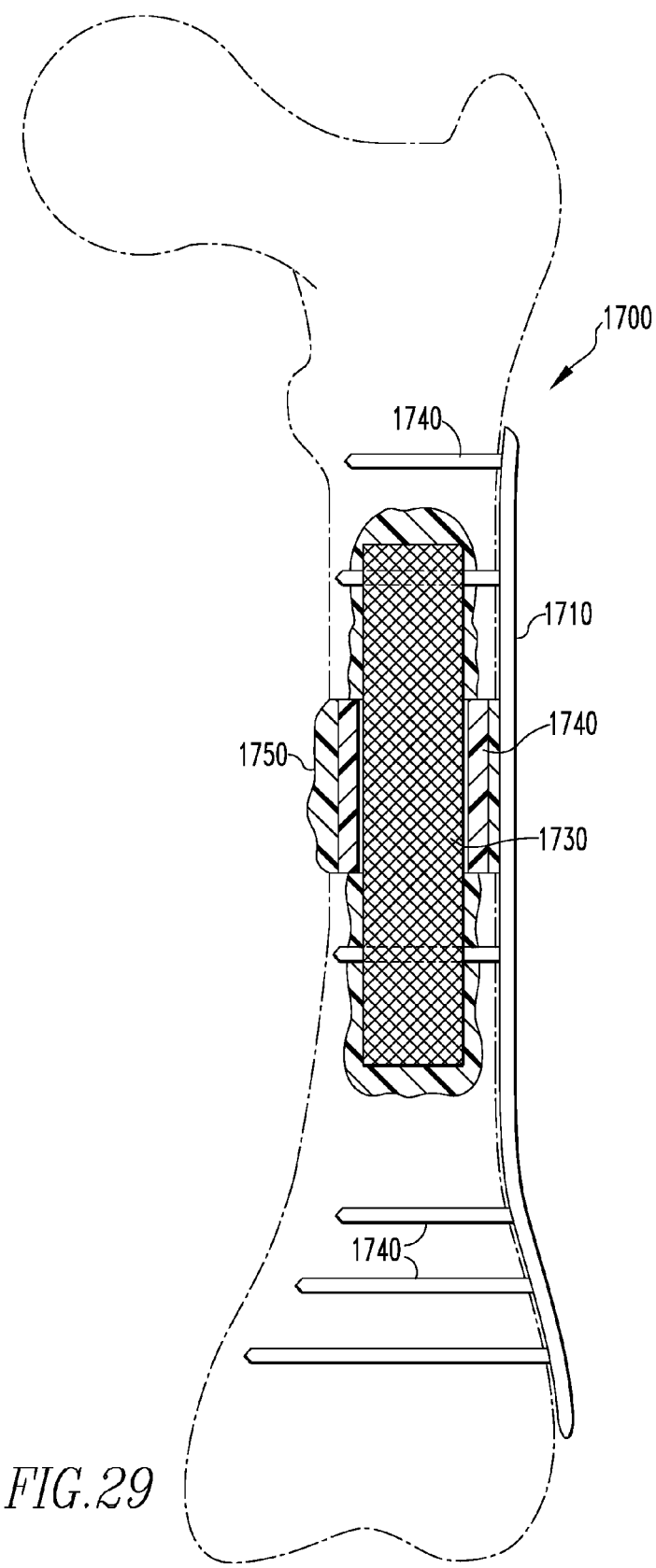
FIG. 29 schematically illustrates an internal fixation system for use with a bone plate.

Any of embodiments disclosed herein may be used to augment external or other internal fixation devices. FIG. 23 illustrates an external fixator augmented with the system 1010; FIGS. 28 and 29 illustrate two more examples of augmentation.

FIG. 28 schematically illustrates a fracture repair system for use with an intramedullary nail 1610. The system 1600 may includes an optional fixator 1630 or simply be packed with void filler 1650 in the form of resin or putty. If used, the fixator 1630 may be fabricated from a braided sleeve but other materials could equally be used. The system 1600 may also include a support 1640 and/or a putty or resin 1650. The intramedullary nail 1610 may be placed in the intramedullary canal and held in place with one or more fasteners 1620, which may be screws. The intramedullary nail 1610 may be made of any biocompatible material, including, but not limited to, stainless steel, titanium, and carbon-reinforced PEEK. The system 1600 may be used with the intramedullary nail 1610 to augment fixation.

FIG. 29 schematically illustrates a fracture repair system for use with an external fixator such as a bone plate 1710. See also the external fixator 1000 of FIG. 23. The system 1700 includes may include an internal fixator 1730. The system 1700 may also include a support 1740 and/or a putty or resin 1750. The bone plate 1710 may be placed on the bone and held in place with one or more fasteners 1740. The bone plate 1710 may be made of any biocompatible material, including, but not limited to, stainless steel, titanium, and carbon-reinforced PEEK. The system 1700 may be used with the bone plate 1710 to augment fixation.

In other embodiments, the fracture repair system may use an external fixator to augment the internal support and putty/resin combination. Typical external fixators include Ilizarov frames, hexapod frames, and bar frames.

FIGS. 30-54

Additional embodiments that make use of the polyurethane resins and polyurethane-based putties disclosed above in combination with braided sleeves, spacer fabrics, balloons, bags, sleeves, chopped fibers and additional structural reinforcing elements, will be discussed below in connection with FIGS. 30-48.

Figure 30:
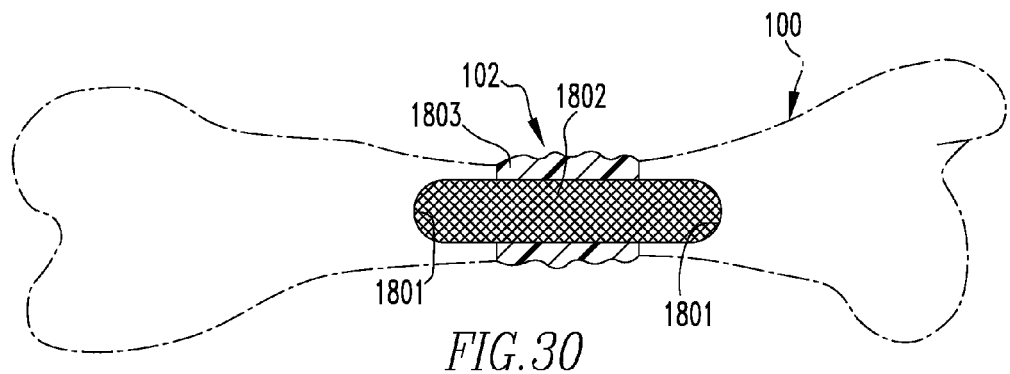
FIG. 30 schematically illustrates an internal fixation system utilizing one or more putties disclosed herein.

Turning to FIG. 30, a bone 100 is shown with a fracture 102. It will be assumed that the fracture 102 is greater than 2 cm wide and is therefore considered to be a large segmental defect. After cavities 1801 are formed in the two bone segments, the cavities 1801 and IM canal may be packed with a putty 1802 with a high degree of strength upon curing. Because bone ingrowth in the IM canal is not important and structural integrity during the healing process is paramount, the putty 1802 may comprise a polyurethane resin with a relatively high 10 μm HA particle content and relatively low porosity such as sample IV of Tables 1 and 2 above.

After the first putty 1802 is in place, a second putty 1803 may be molded in the annular area of cortical bone loss. Because cortical bone ingrowth is paramount for the annular area in which the second putty 1803 is placed, the second putty 1803 should be porous upon curing like samples II, III or VI. Obviously, the exact formulas for the putties 1802, 1803 may be varied as will be apparent to those skilled in the art. Further, the putties 1802 and 1803 may be combined with any one or more of the supporting structural elements described above in connection with FIGS. 1-29 or below in connection with FIGS. 31-45.

Figure 31:
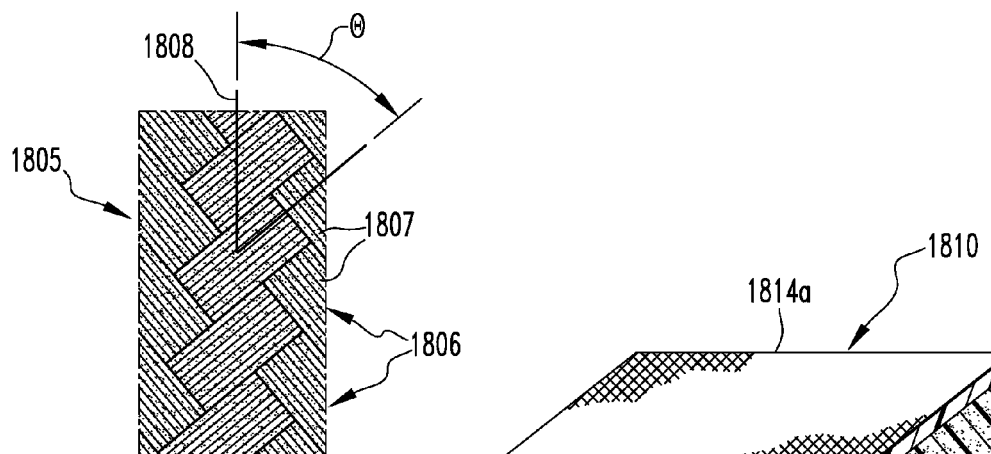
FIG. 31 is a partial and enlarged view of a disclosed elongated and reinforcing braid structure used with a biocompatible resin and, optionally, one or more of a balloon, a bag, a sleeve, chopped fibers, additional braid structures and/or an additional reinforcing pin or tube as illustrated below.

Turning to FIG. 31, an exemplary braided structure 1805 is disclosed. The braided structure 1805 includes a plurality of bundles 1806 with each bundle including a plurality of filaments 1807. The braided structure 1805 is also characterized by the braid angle θ, which is the angle between the bundles 1806 and the long axis 1808 of the braided structure 1805. The braid diameter, or the diameter of the finished braided elongated structure 1805 after heat setting and in a relaxed state, is also a relevant physical property. The "locked-out" diameter of a braided elongated structure 1805 is also a relevant physical property. The locked-out diameter of a braided elongated structure 1805 is defined as the diameter of the braided structure 1805 when the structure 1805 is fully stretched along its long axis 1808. The locked-out diameter of a braided structure 1805 is related to the number of braiding heads used to weave the elongated braided structure 1805, the number of filaments 1807 in each bundle 1806 and the braiding angle θ. If the number of braiding heads and the number of filaments 1807 in each bundle 1806 is constant, the diameter of the locked-out braid 1805 will decrease as the braiding angle θ decreases. As the ratio of the braid diameter (after heat setting, relaxed state) to the locked-out diameter increases, the braid becomes more open in the relaxed state, i.e. the openings between the bundles increase in size and the elongated braided structure 1805 filled with resin is more prone to leakage between the bundles 1806.

Effect of Braiding Parameters on Braid Performance in Fracture Fixation Device

A range of biaxial braids were produced from PLLA monofilaments, 100 μm in diameter. Properties of the elongated braided structures are summarized in Table 3 below.

TABLE 3

Braid Properties

| Braid ref no. | Braiding heads | Filaments per bundle | Locked-out braid diameter (mm) | Diameter of mandrel braid manufactured on (mm) | Diameter of mandrel used for heat setting (mm) | Braid length (mm) (locked-out state) | Braid angle θ (°) |
|---|---|---|---|---|---|---|---|
| 66/01 | 16 | 32 | 4.43 | 6.25 | 6.25 | 22.8 | 11 |
| 66/02 | 16 | 32 | 4.36 | 6.25 | 6.25 | 31.2 | 8 |
| 66/03 | 16 | 32 | 4.51 | 6.25 | 6.25 | 26.0 | 9.8 |
| 67/01 | 16 | 19 | 3.60 | 6.25 | 6.25 | 9.6 | 20.6 |
| 67/02 | 16 | 19 | 3.43 | 6.25 | 6.25 | 20.0 | 9.7 |
| 67/03 | 16 | 19 | 3.54 | 6.25 | 6.25 | 34.8 | 5.8 |
| 68/01 | 16 | 27 | 4.41 | 6.25 | 6.25 | 11.2 | 21.5 |
| 68/02 | 16 | 27 | 4.35 | 6.25 | 6.25 | 22.5 | 10.9 |
| 68/03 | 16 | 27 | 4.18 | 6.25 | 6.25 | 31.5 | 7.6 |

The elongated braided structures were produced in sleeve format on a 16-head machine (Pickmaster, JB Hyde & Co). Each head was threaded up with 100 μm PLLA filament ends. The fiber bundles (or yarns) were twisted at a rate of 20 turns per meter to help maintain their integrity. The bundles were then braided over a fixed diameter mandrel using a bias weave. In this configuration, the continuous yarns crossed over and under each other to form a continuous spiral pattern with eight bundles traveling in one direction and the remaining eight bundles in an opposite direction.

A series of braids were produced with varying braid length, defined as the length of braid per 360 degrees revolution of each yarn around the braid. The braid length was measured in a locked-out state (i.e., fully stretched in the axial directions) as the braid came off the machine. The woven sleeves were heat-set over the same diameter mandrel by immersion in hot water at 90 degrees C. for about 10 seconds.

The elongated braided structures were then tested for bending strength by placing the elongated braided structures in a PTFE oven with a cylindrical cavity 7 mm in diameter and 100 mm long. The 100 mm length of braid was inserted into the cavity, which was then filled with a degradable polyurethane resin (PolyNovo Pty. Ltd.) and allowed to cure at 37 degrees C. for 72 hours. The samples were removed from the oven and left to cure at 37 degrees C. for another 24 hours. The samples were then removed from the oven and tested in 3 point bend with a support span of 70 mm and a cross head speed of 3.4 mm/min. The flexural modulus from the test for the different braids is shown in the table below.

TABLE 4

Effect of Braid Length and Angle on Flexural Modulus

| Braid ref. no. | Braid length (mm) | Braid angle θ (°) | Flexural modulus/ (GPa) |
|---|---|---|---|
| 66/01 | 22.8 | 11 | 2.63 |
| 66/02 | 31.2 | 8 | 2.81 |
| 66/03 | 26.0 | 9.8 | 2.97 |
| 67/01 | 9.6 | 20.6 | 2.19 |
| 67/02 | 20.0 | 9.7 | 2.24 |
| 67/03 | 34.8 | 5.8 | 2.49 |
| 68/01 | 11.2 | 21.5 | 2.26 |
| 68/02 | 22.5 | 10.9 | 2.37 |
| 68/03 | 31.5 | 7.6 | 2.72 |

From Table 4, it can be observed that as the braid length increases, the flexural modulus increases. This behavior was attributed to higher braid lengths resulting in reduced braid angles θ, i.e., the angle between the direction of the fibers in a bundle and the longitudinal axis of the braid. The resulting improved alignment between the fibers and the braid results in a greater proportion of the fibers' properties contributing to the overall strength of the composite material. However, it is also observed that, as the braid length increases, the springiness or recovery force of the elongated braided structures decreases, which is undesirable. Further, the elongated braided structures with longer braid lengths were also observed to larger interstices in the relaxed state and were therefore more prone to allowing leakage of the resin through the walls of the elongated braided structures. Both of these observations appear to indicate that (1) elongated braid structures with high braid lengths have lower recovery forces and are therefore less likely to self expand and conform to the endosteal wall that (2) such elongated braid structures will allow significant leakage of resin past the braid and may therefore may need a retention means for inhibiting migration of resin such as a balloon, bag or sleeve as discussed below in connection with FIGS. 36-48.

Braids with increased numbers of filaments in each bundle were found to be harder to compress and would require a larger entry hole into the bone. Alternatively, as the braid length increases, the braid becomes easier to compress. As a result, elongated braid structures with braid angles θ greater than about 8 degrees are suitable for most fracture fixation applications. Ideally the braid angle θ ranges from about 8 degrees to about 20 degrees, more preferably from about 8 degrees to about 12 degrees.

Surface Treatment of Braids of Braid/Polyurethane Resin Composite Structures

Surface treatments of braids were conducted to determine the effect on the properties of the composite structure (i.e., braid and resin). Sections of the braid number 66/03 were treated as follows with the results being tabulated in Table 5. A control braid washed in isoproponal for a minimum of 2 hrs and air dried. For the air plasma treatment, the braid treated with air plasma for 5 minutes at a pressure of $1.2 \times 10^{-1}$ bar, at a reflected power of 5 W. For the extended argon plasma treatment, the braid was exposed for 20 minutes in a 60 degrees C. chamber temperature, $2 \times 10^{-1}$ pressure and a reflected power of 20 W. For the NaOH etch, the braid was immersed in 4 M NaOH solution for 2 hours and then air dried. For the allyl alcohol plasma, the braid was treated at a pressure of 200 mtorr allyl alcohol and a reflected power of 20 W with a treatment cycle comprising 2 minutes of continuous wave plasma followed by 15 minutes of pulsed plasma with a duty cycle of 1 ms (on)/5 ms (on & off). The flexural properties of the composites made from the above surface-treated braids are given in the Table 5 below. The polyurethane resin contained 20 wt % HA with an average particle size below 10 μm (Plasma Biotal, UK) as a filler.

TABLE 5

Effects of Surface Treatment on Elongated Braid Structures

| Braid treatment | Flexural strength/ (MPa) | Flexural modulus/ (GPa) |
|---|---|---|
| Control-no treatment | 97.8 | 2.97 |
| Air Plasma | 105.3 | 2.93 |
| Argon Plasma | 116.4 | 3.13 |
| NaOH etch (4M solution) | 104.0 | 2.89 |
| Allyl Alcohol plasma | 118.7 | 3.20 |

Figure 33:
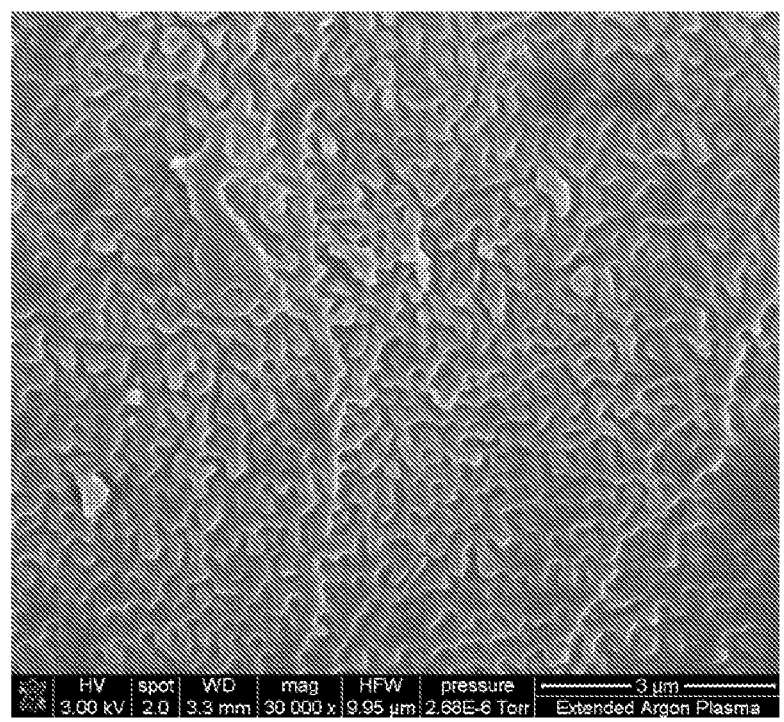
FIG. 33 is a photograph illustrating a topological texture induced in a braid surface as a result of argon etching.

As shown in SEM image of FIG. 33, the argon plasma treatment creates a micro-texture on the surface of the PLLA fibers. Without being bound to any particular theory, it is believed that the microtexture shown in FIG. 33 will improve the mechanical interlocking between the fibers in the braid and the cured polyurethane resin and hence improve the mechanical properties of the final composite structure which comprises an elongated braid saturated with polyurethane or another suitable resin, which has been cured.

Braids with Longitudinal Fibers

Figure 34:
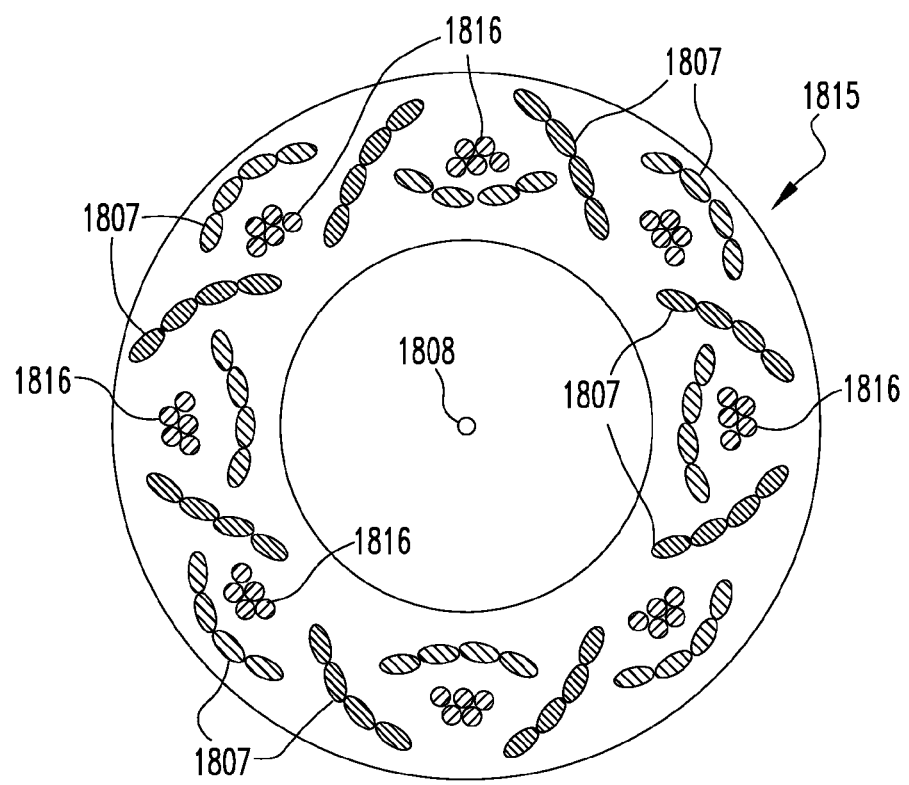
FIG. 34 is an end view of an elongated braided structure with a plurality of longitudinal reinforcing fiber bundles.

The mechanical performance of the elongated braided structures can be further improved by the incorporation of longitudinal fibers. Specifically, the cross-sectional view of FIG. 34 shows an elongated braid 1815 with braid bundles 1807 and the longitudinal fiber bundles 1816. The additional longitudinal fibers 1816 are aligned with the axis 1808 of the braid 1815 and significantly improve the bending strength of the final composite material, which is the primary loading condition imposed on fracture fixation devices. Such braids 1815 are also referred to as triaxial braids.

For example, triaxial braids 1815 were made which had an approximate relaxed external diameter of 3 mm. The elongated braided structures 1815 were manufactured to a nominal external diameter of 3 mm with eight bundles 1816 of longitudinal fibers per braid. Triaxial braids 1850 with bundles 1860 of longitudinal fibers of two, five and eight fibers were made and tested.

Testing was done by inserting the elongated braided structures into a plastic rod of 70 mm length, with a cut half way to simulate a fracture. As an example, the plastic rod could be made of Delrin®. Delrin® is a registered trademark of E.I. Du Pont De Nemours and Company of Wilmington, Del. The rod has an internal channel through the section with a 3 mm diameter. After placement of the braid, a polyurethane resin was used to fill the canal and left to cure at 37 degrees C. The samples were then tested using a cantilever test method. One side of the plastic rod was firmly clamped, and the plastic rod on the opposite side of the simulated fracture was loaded at a distance of 25 mm from the fracture at a rate of 10 mm/min. A chamfer at an angle of 45 degrees C. was cut on the lower side of the plastic rod each side of the fracture to prevent the two pieces of plastic impinging on each other during the test.

Figure 35:
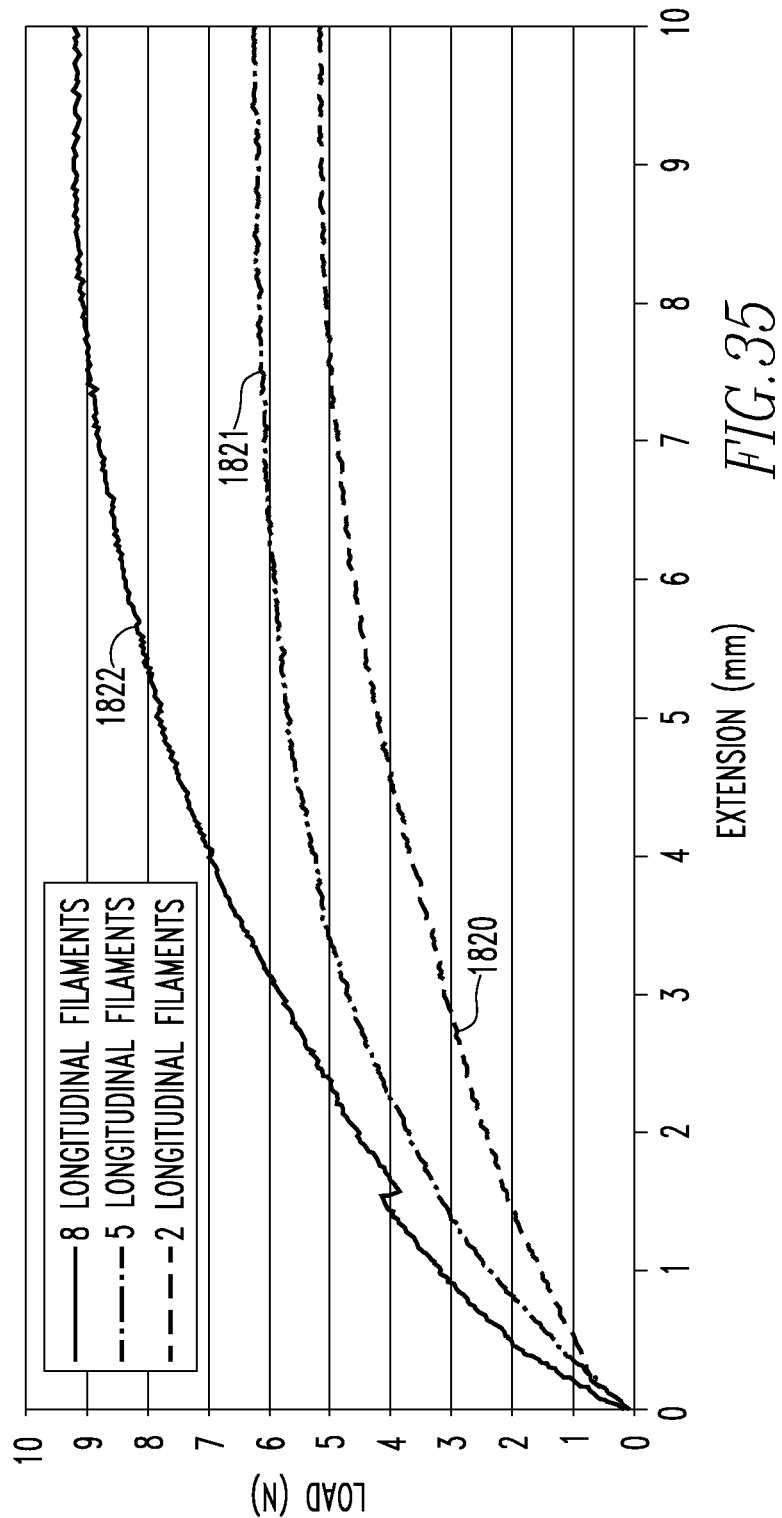
FIG. 35 graphically illustrates the effect of a number of longitudinal fibers filaments in longitudinal fiber bundles on loadbearing properties of elongated braid structures equipped with longitudinal fiber bundles.

The corresponding moment v. extension curves 1820, 1821, 1822 for the two longitudinal filaments per bundle 1816 sample, five longitudinal filaments per bundle 1816 sample and eight longitudinal filaments per bundle 1816 sample respectively are graphically presented in FIG. 35. It can be seen that as the number of longitudinal fibers increases from two longitudinal filaments per longitudinal bundle 1816 (see the plot line 1820) to eight longitudinal filaments per longitudinal filament bundle 1816 (see the plot line 1822), the load required (y-axis) to deform the sample to a given extension (x-axis) increases.

Alternatively, the ability of triaxial braids 1815 to be compressed and return to the heat-set diameter can be improved by using crimped fibers as the longitudinal reinforcement. Crimped longitudinal fibers can be used individually, i.e., as a single fiber, or can be combined into bundles like those shown at 1816 in FIG. 34.

Further, the braids for the fracture fixation devices may be made from braids or cords. For example, PLLA filaments (~100 μm diameter) could be braided into a cord to produce a cord with a 2 mm diameter. These cords could then be braided into a biaxial or triaxial braided sleeve suitable for bones with large IM canals. The advantage braided cord or braided braid designs is excellent recovery properties. In contrast, large braids made from PLLA filaments alone may not have sufficient recovery properties.

Shaped Tip to Facilitate Insertion of the Elongated Braid or Spacer Fabric

Figure 36:
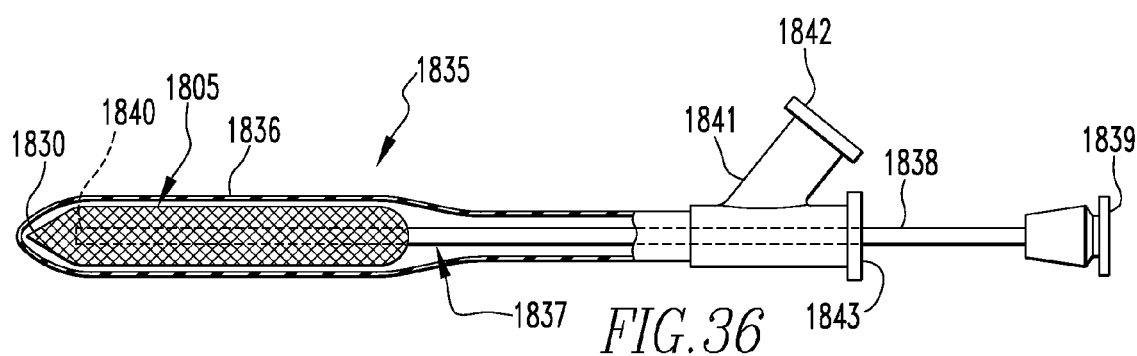
FIG. 36 is a side to sectional view of an insertion assembly for placing a disclosed reinforcing device in an IM canal amount wherein the reinforcing device comprises a braid or spacer fabric as illustrated in FIGS. 31-32A respectively.
Figure 38:
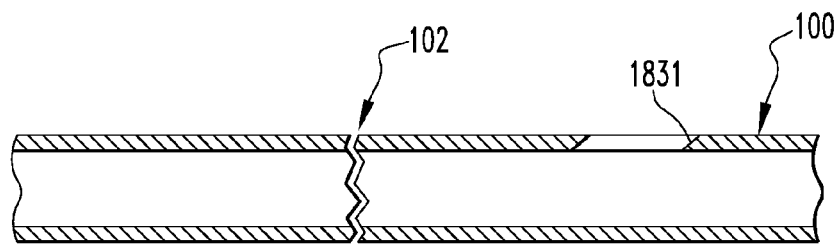
FIG. 38 is a schematic sectional view of a fractured bone, IM canal and insertion port that has been previously drilled through the outer cortical and endosteal wall structures of the fractured bone.

Turning to FIGS. 36 and 38, a shaped, tapered or pointed distal end 1830 of the elongated braided structure 1805 improves the ease in which a braid 1805 can be inserted into a bone 100 through a narrow injection opening or port 1831 or the ease in which a braid 1805 and assembly 1835 can be inserted through the opening 1831. The assembly 1835 shown in FIG. 36 may include a balloon 1836 (or alternatively, bag or sleeve), an injection tube 1837, chopped fibers (not shown) and structural reinforcing elements (also not shown). Ideally, the end 1830 of the elongated braided structure 1805 is shaped into a point as shown in FIG. 36. The pointed end 1830 can be formed by melting the end of the elongated braided structure 1805 (or spacer fabric structure 1810) in a conical mold (not shown) to produce a pointed tip 1830. If the elongated braided structure 1805 is to be used in a segmental defect (FIG. 30) then a pointed end 1830 can be formed at both ends of the elongated braided structure 1805 to improve the insertion into the bone IM cavity of each piece of bone. Other shapes for the tip 1830, where the cross-sectional area of the tip 1830 is less than the cross-sectional area of the elongated braided structure 1805 will also improve the insertion ability. Examples include a rounded tip, a flat ribbon like tip with rounded or sharp point, or a curved tip to aid in non-axial entries. Other tip designs are too numerous to mention here as will be apparent to those skilled in the art.

It is also possible to include a radiopaque material or marker into the shaped tip 1830 to allow visualization of the distal end 1830 of the elongated braided structure 1805 during insertion. This would allow the surgeon to ensure the elongated braided structure 1805 is inserted past the fracture site 102 to an optimal position before the resin in inserted and allowed to cure. For example the shaped tip 1830 could be made by melting some PLLA (or other degradable polymer) containing a radiopaque filler (e.g., hydroxyapatite) around the end 1830 of the elongated braided structure 1805 during the shaping operation.

Ideal Filler Level for Resin

To allow the samples to be radiopaque, about 20 wt % hydroxyapatite (HA) was mixed with the polyurethane resin. A range of particle sizes were investigated, particle size analysis data is given in the table below. Particle characterization was carried out using a Beckman Coulter LS 13 320 Series Laser Diffraction Size Analyzer with Tornado Dry Powder System. All HA was oven dried, sintered and milled to form angular shaped particles (no spray dried) and supplied by Plasma Biotal, UK.

TABLE 6

Effect of HA Mean Particle Variation on Braid/Resin Composite Structures

| HA | Mean (μm) | $d_{10}$ | $d_{50}$ | $d_{90}$ |
|---|---|---|---|---|
| Powder 1 | 9.982 | 6.128 | 11.55 | 16.74 |
| Powder 2 | 107.5 | 68.78 | 135.5 | 192.5 |
| Powder 3 | 281.3 | 167.3 | 316.1 | 524.8 |

Mean is the volume mean diameter, $d_{10}$ is the diameter size wherein 10% of the sample has a smaller diameter; $d_{50}$ is the diameter size wherein 50% of the sample has a smaller diameter; and $d_{90}$ is the diameter size wherein 90% of the sample has a smaller diameter.

It was found that if the HA particles were too large then they settled under gravity in the resin before it cured. To best accommodate the viscosity of the polyurethane resin, a powder with an average size of around 10 μm was found to be ideal. To determine the ideal filler level, a series of samples were made with Powder 1 (Table 6) at different filler levels as shown in Table 7. Braid ref. no. 67/02 (Table 4) was used for each sample. The samples were made by placing the elongated braided structures in a PTFE mold with a cylindrical cavity 7 mm in diameter and 100 mm long. The 100 mm length of braid was inserted into the cavity, which was then filled with a degradable polyurethane resin (PolyNovo Pty Ltd) containing the fillers and allowed to cure in an oven at 37 degrees C. for 72 hours. The samples were then removed from the mold and left in the oven to cure at 37 degrees C. for a further 24 hours. The samples were then removed from the oven and tested for mechanical strength in three-point bend with a support span of 70 mm and a cross head speed of 3.4 mm/min. The flexural modulus from the test for the different braids is shown in the Table 7.

TABLE 7

Effect of HA Content on Braid/Resin Composite Structures

| Filler Level (% w/w) | Peak Flex Strength (MPa) | Flex Modulus (GPa) | Strain to Failure (%) |
|---|---|---|---|
| 20 | 65.6 | 2.3 | No failure observed to 21% strain |
| 25 | 57.5 | 2.2 | No failure observed to 21% strain |
| 30 | 64.9 | 2.6 | 12.6 |
| 35 | 69.4 | 3.1 | 9.5 |
| 40 | 63.8 | 3.5 | 5.5 |

It can be seen that, as the wt % of fillers increases, in general, the flexural modulus of the samples increases and that the strain to failure decreases. Based on the results obtained for mechanical properties and radiopacity, a HA filler with a particle size of around 10 μm and at a level between 20 and 35 wt % is satisfactory, with a level of 30 wt % being more satisfactory. Higher or lower HA levels would be acceptable, depending on the application.

As illustrated in connection with FIGS. 36-48, the elongated braided structures 1805 or spacer fabric could also be contained in a balloon 1836, bag or sleeve. Balloons 1836, bags or sleeves may eliminate or reduce resin leakage past the elongated braided structure 1805 or spacer fabric and into the fracture site, also known as extravasation. Use of crimped fibers as longitudinal components in a triaxial braid 1815 (FIG. 34) may also provide improved performance. Use of braids 1805 made more bundles and fibers produce braids 1805 with a tighter weave thereby reducing leakage of resin through the elongated braided structure 1805.

As shown below, a braided elongated structure 1805 may be used to provide reinforcement for an in situ curable intramedullary fixation device. The elongated braided structure 1805 may be inserted into the IM canal of the bone 100, followed by an in situ curable resin, e.g. polyurethane resin, which will penetrate the elongated braided structure 1805 and harden. After the resin has cured, the combination of the resin and braid 1805 forms a fiber reinforced composite structure.

Figure 32:
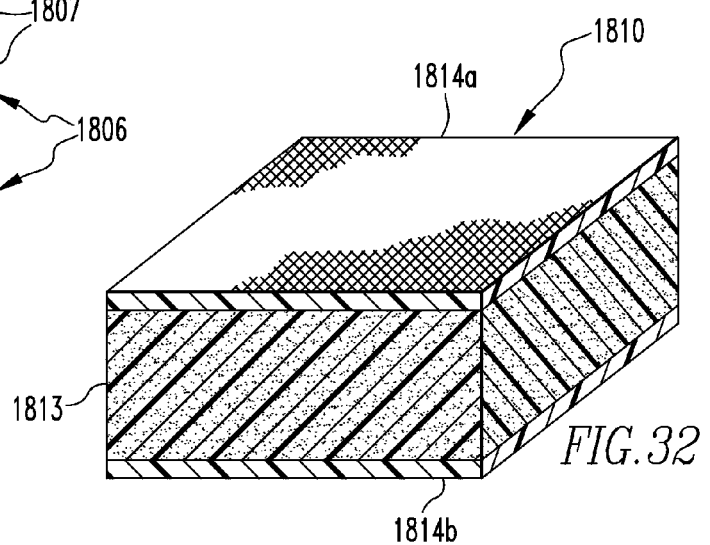
FIG. 32 is a partial and enlarged view of a disclosed reinforcing spacer fabric that may be used with a biocompatible resin and, optionally, one or more of a balloon, a bag, a sleeve, chopped fibers, additional woven elongated structures and an additional reinforcing pin or tube as illustrated below.
Figure 32A:
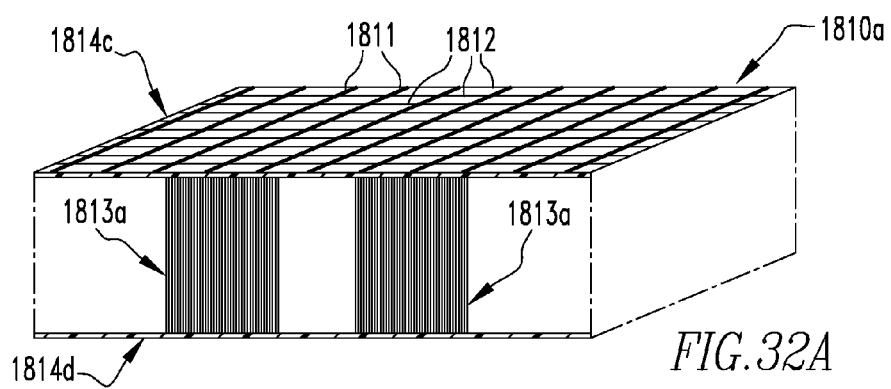
FIG. 32A is a partial and enlarged view of another disclosed reinforcing spacer fabric similar to FIG. 32, with thicker longitudinal fibers or fiber bundles and spacings between groups of vertical fibers.

Similar to a braided elongated structure 1805, a structure made from spacer fabric structures 1810, 1810a as shown in FIGS. 32-32A may be employed. The spacer fabric structures 1810, 1810a also readily absorb resin and form a fiber reinforced composite material similar to the braided structure 1805 of FIG. 31. Once formed as an elongated roll, fold or elongated structure, the spacer fabric structures 1810, 1810a can be compressed and subsequently expand to the generally cylindrical, but irregular shape of an IM canal. For example, the spacer fabric structures 1810, 1810a that have a relaxed cross-sectional width of about 8 mm can be compressed to fit inside an insertion tube with an inner diameter of about 3.9 mm, leaving room for an axial injection tube having an OD of about 2 mm.

In FIGS. 32-32A, the spacer fabrics 1810, 1810a include top and bottom panels 1814a-1814b and 1814c-1814d respectively. In FIG. 32 the middle section 1813 includes an essentially uniform distribution of fibers extending between the top and bottom panels 1814a, 1814b. In FIG. 32A, groups of vertical fibers 1813a are spaced apart. As one example, for a piece of spacer fabric 1810a that is about 14 mm wide and about 8 mm thick, the groups of fibers 1813a may have widths of about 3 mm with spacings of about 2 mm between groups 1813a. Of course, these dimensions can vary greatly and will depend on the width, thickness and desired compressibility and expandability properties of the spacer fabric.

In FIG. 32A, the spacer fabric 1810a includes longitudinal fibers 1811 or longitudinal fiber bundles having diameters greater than the transverse fibers 1812. For a spacer fabric 1810a that is about 14 mm wide, 8 mm thick, the longitudinal fibers 1811 may have diameters of about 100 µm while the transverse fibers 1812 may have smaller diameters, for example about 20 µm. Multiple longitudinal fiber bundles or yarns may be used instead of single longitudinal fibers 1811. The vertical fibers 1813a may also have larger diameters of about 100 µm. One disclosed spacer fabric is fabricated from PLLA but other resorbable polymer fibers discussed above may be used as will be apparent to those skilled in the art.

Figure 37:
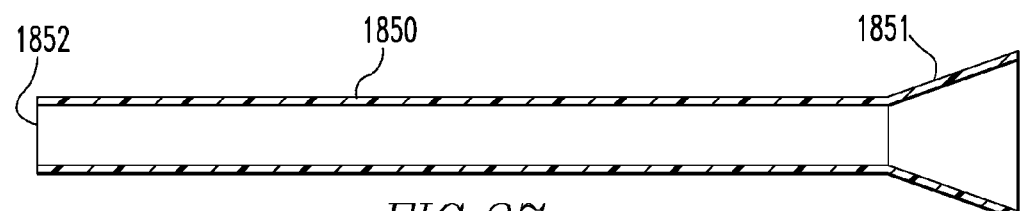
FIG. 37 is an insertion tube for use with the insertion assembly of FIG. 36.

Methods and instruments for introducing fixation devices in the IM canal of a fractured bone are illustrated in FIGS. 36-48. Turning first to FIG. 36, an insertion assembly 1835 comprises an injection tube 1837 with a proximal end 1838 connected to an injection port 1839. The injection tube 1837 also includes a distal end 1840 disposed axially within the elongated braided structure 1805 (or spacer fabric structure 1810). In the embodiment shown in FIG. 36, the elongated braided structure 1805 is contained within a balloon 1836 which may also be a bag, sleeve or other suitable retention element. The injection tube 1837 passes through a hemostasis valve 1841 that includes a filter side port 1842 which contains fluid but allows air or gases to release, and a port 1843 through which the injection tube 1837 passes. An insertion tube or catheter 1850 is shown in FIG. 37 with a flared proximal end 1851 and a narrow distal or insertion end 1852.

Figure 39:
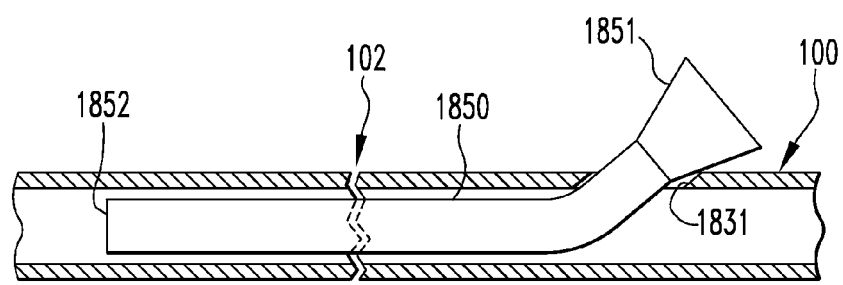
FIG. 39 is a schematic sectional view of the bone illustrated in FIG. 38 with the insertion tube of FIG. 37 disposed therein.
Figure 40:
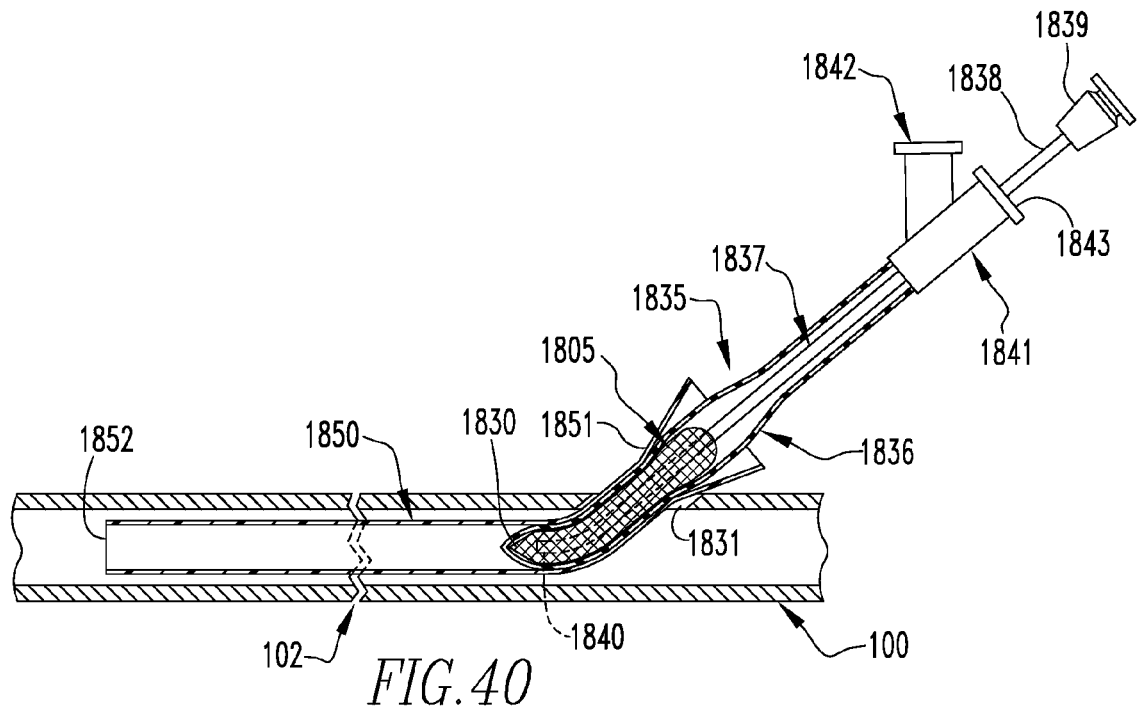
FIG. 40 is a schematic sectional view of the assembly, insertion tube and bone of FIGS. 36-39, particularly illustrating the insertion of the assembly through the insertion tube.
Figure 41:
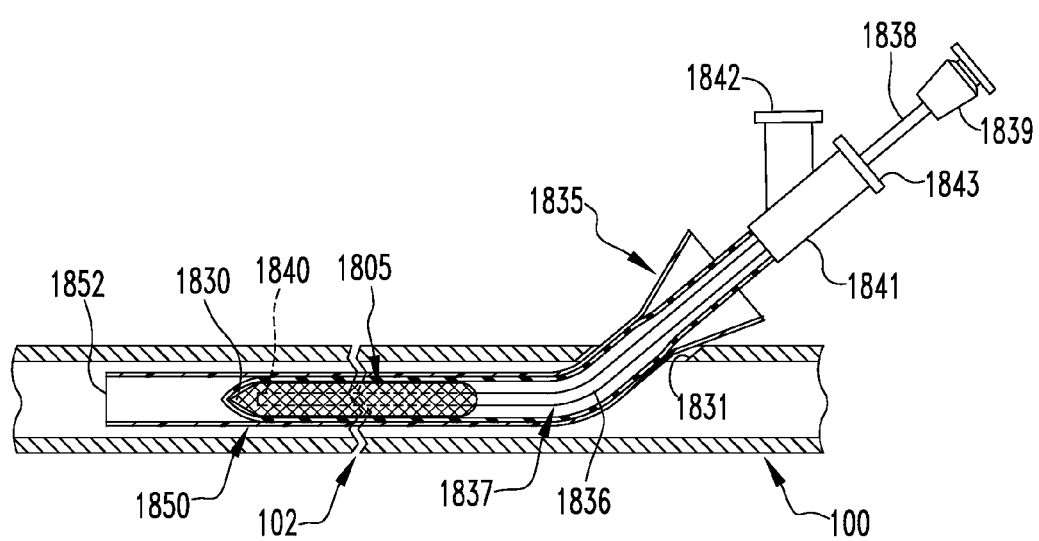
FIG. 41 is a schematic sectional view of the assembly, insertion tube and bone of FIGS. 36-40, particularly illustrating the placement of the assembly across the fracture site.

Turning to FIG. 38, an injection port 1831 is formed in the cortical wall of the fractured bone 100 by drilling or other means and the IM canal is reamed or otherwise prepared using methods known to those skilled in the art. In FIG. 39, the insertion tube 1850 is inserted through the port 1831 so that its distal end 1852 extends past the fracture 102. As shown in FIG. 40, the assembly 1835 is inserted through the proximal end 1851 of the insertion tube 1850. As shown in FIG. 41, the assembly 1835 is pushed downward through the insertion tube 1850 until the elongated braided structure 1805 straddles either side of the fracture 102.

Figure 42:
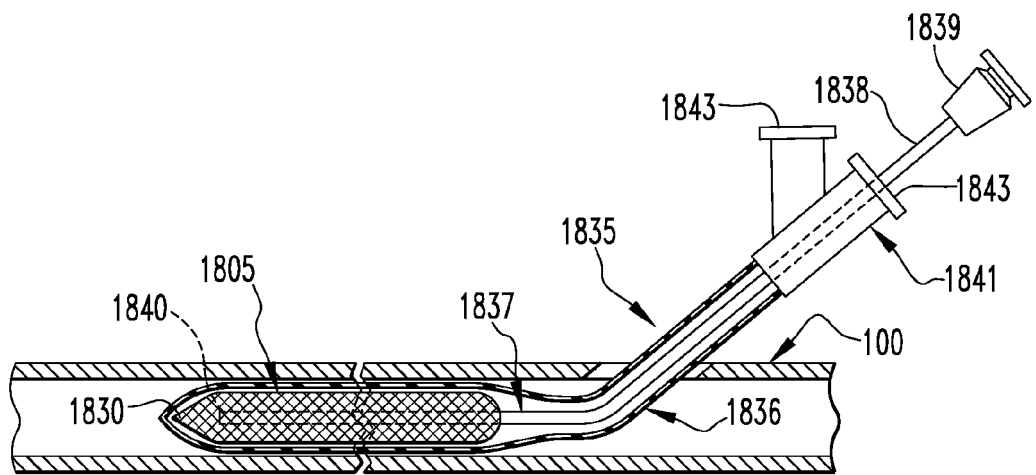
FIG. 42 is a schematic sectional view of the assembly and bone of FIGS. 36 and 38-41, after the insertion tube of FIG. 37 has been removed and the braid or spacer fabric has been allowed to expand.
Figure 43:
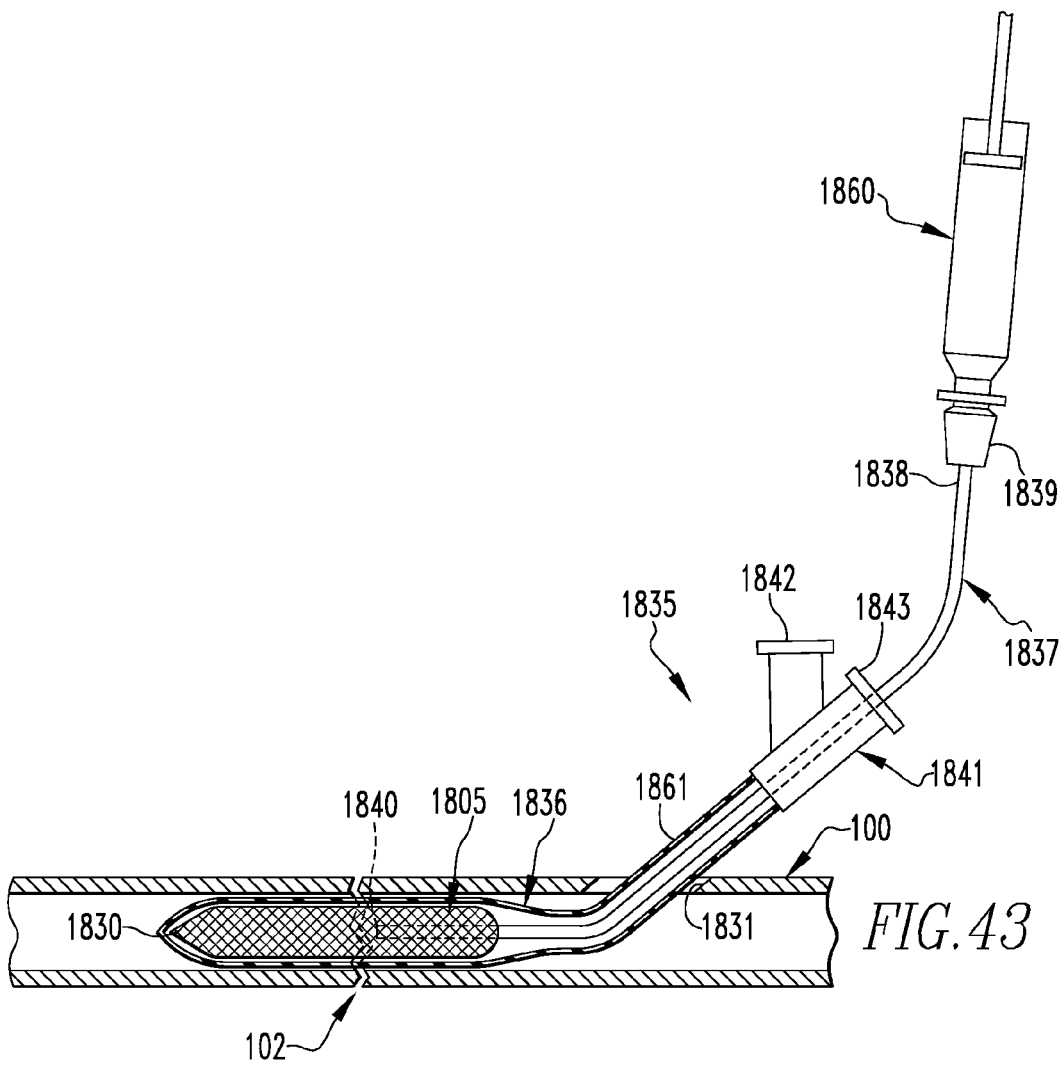
FIG. 43 is a schematic sectional view of the assembly and bone of FIGS. 36 and 38-42, particularly illustrating the injection of resin into the braid or spacer fabric and optional balloon, bag or sleeve.
Figure 44:
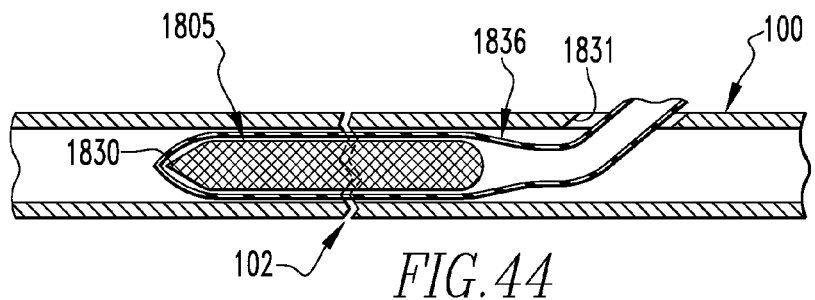
FIG. 44 is a schematic and sectional view of a braid or spacer fabric, optional balloon, bag or sleeve, and resin disposed across a fracture site, whereby if an optional balloon, bag or sleeve is utilized, excess balloon, bag or sleeve material is cut at the insertion port through the cortical wall.

Once the position shown in FIG. 41 is reached, the insertion tube 1850 can be withdrawn through the opening as indicated in FIG. 42. As shown in FIG. 43, the elongated braided structure 1805 and balloon 1836 can be filled with resin using the injector 1860. During the injection process illustrated in FIG. 43, the injection tube 1837 can be retracted proximally from the position shown in FIG. 42 to the position shown in FIG. 43 and further proximally until the tube 1837 is withdrawn entirely from the balloon 1836 and hemostasis valve with side port 1841 as illustrated in FIG. 44. Further, as shown in FIG. 44, the proximal end 1861 of the balloon 1836 may be trimmed at the injection port 1831. The trimming process may be performed before or during the setting of the resin. The balloon 1836 and braid 1805 may be fabricated from resorbable materials.

Figure 46:
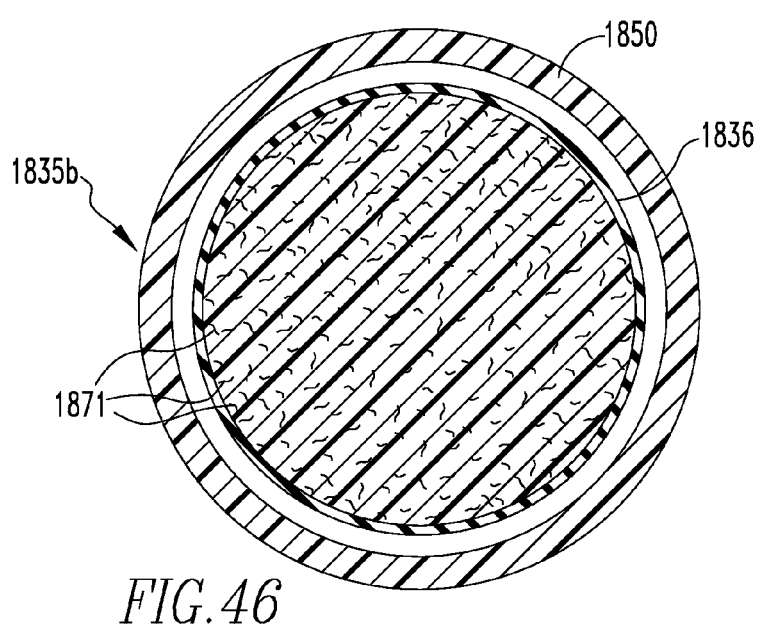
FIG. 46 is a sectional view of another disclosed assembly for use with the procedure illustrated in FIGS. 38-44.
Figure 47:
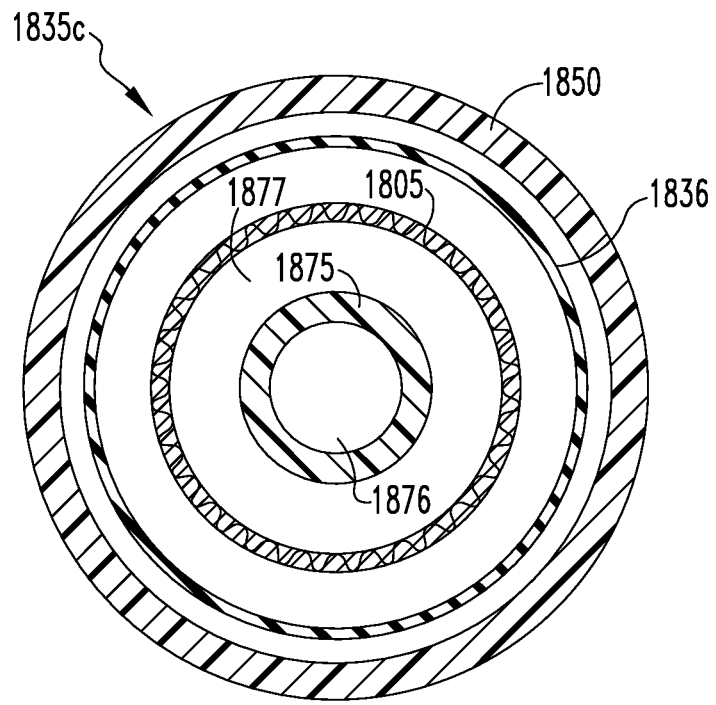
FIG. 47 is a sectional view of yet another disclosed assembly for use with the procedure illustrated in FIGS. 38-44.
Figure 48:
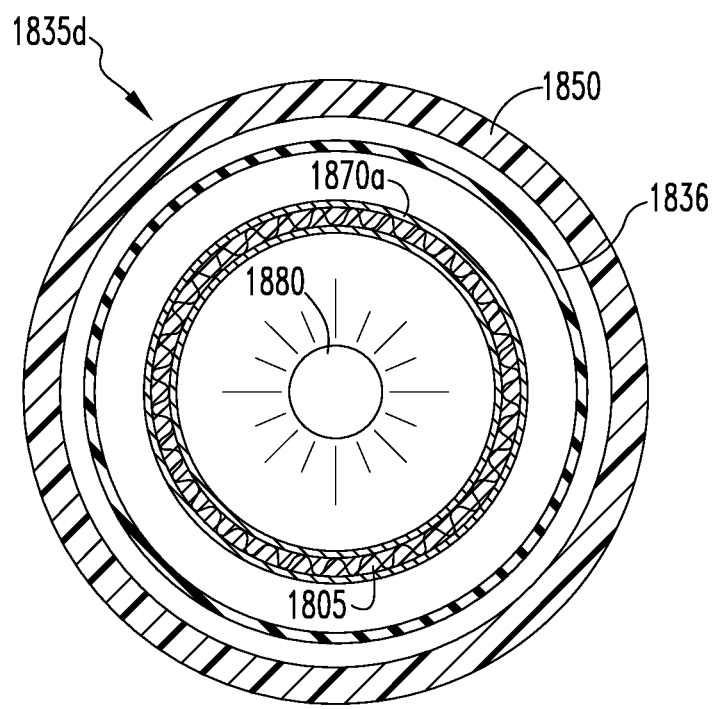
FIG. 48 is a sectional view of another disclosed assembly for use with the procedure illustrated in FIGS. 38-44.

As illustrated in FIGS. 45-54, the components of the assembly 1835 can be varied. For example, the balloon 1836 may be replaced with the bag or sleeve or other suitable enclosure for retaining resin in the IM canal. The elongated braided structure 1805 may be replaced with a triaxial braid 1815, a spacer fabric structure 1810, or one of the structures shown in FIGS. 49-54. The balloon 1836, bag or sleeve may be eliminated entirely if the combination of the braid or spacer fabric and resin provides the desired amount of resin retention. Chopped fibers may also be inserted into either the balloon 1836 (or bag or sleeve), braid 1805 or spacer fabric to strengthen the resin and/or the composite structure. If chopped fibers are utilized, an elongated braid or spacer fabric may not be necessary and a balloon, bag or sleeve structure containing a suitable amount of fibers can be inserted into the IM canal and filled with resin. Reinforcing elements in the form of pins or tubes may also be employed. If a reinforcing element is utilized, a braided sleeve or spacer fabric may be utilized, pre-wetted with resin, the excess resin removed and the braid or spacer fabric inserted into the IM canal using the reinforcing element. In such an embodiment, the resin may be light curable and a light pipe or light device may be inserted downward through the braid or spacer fabric for curing the resin as shown in FIG. 48 and discussed below.

FIGS. 45-48 are cross-sectional views of various insertion assemblies 1835a-1835d. These cross-sectional views are not the scale and are intended to describe the various combination of elements for insertion assemblies that are encompassed by this disclosure.

Figure 45:
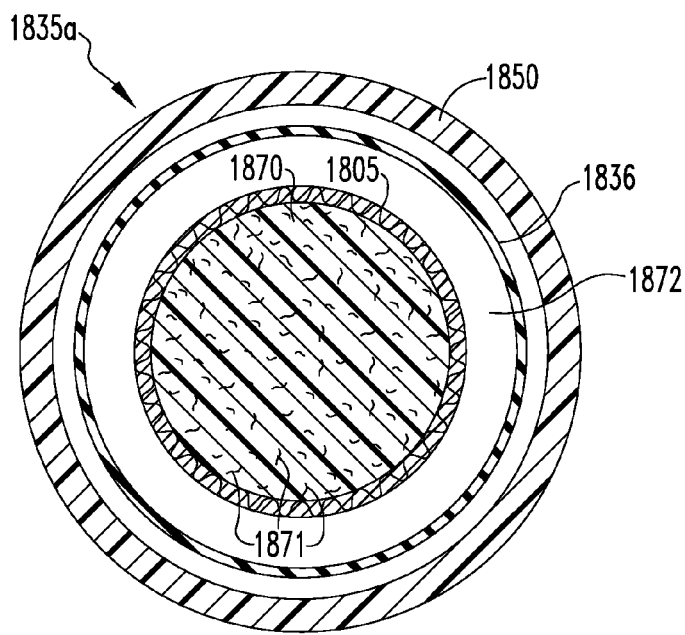
FIG. 45 is a sectional view of one disclosed assembly for use with the procedure illustrated in FIGS. 38-44.

FIG. 45 is a cross-sectional view of an assembly 1835a that comprises an insertion tube 1850, a balloon 1836 (or bag or sleeve) and an elongated braid 1805 (or triaxial braid 1815 or spacer fabric structure 1810). The elongated braided structure 1805 is filled with resin 1870 using an injection tube 1837 (not shown in FIG. 45). Optionally, the elongated braided structure 1805 may have been partially filled or charged with chopped fibers 1871 for added strength to the composite structure once the resin 1870 has cured. It is anticipated that the elongated braided structure 1805 may be chosen so as to prevent migration of resin 1870 to the annular area 1872 between the elongated braided structure 1805 and the balloon 1836. If this is the case, the balloon 1836 (or bag or sleeve) may not be necessary. If substantial migration occurs to the area 1872, a retention means such as a balloon 1836 or bag or sleeve may be desirable to prevent resin migration to other parts of the patient's body. The elongated braid 1805 and balloon 1836 are sized to expand and engage the endosteal wall of the IM canal. The expansion may be natural for the elongated braided structure 1805 as it expands to its relaxed state or the expansion may be prompted or caused by the injection with the resin 1870.

On the other hand, turning to FIG. 46, a braid, bag or sleeve is not utilized. In the assembly 1835b includes an insertion tube 1850 a balloon 1836 (or bag or sleeve) and an injection tube 1837 (not shown). In the assembly 1835b, the balloon 1836 is optionally charged with chopped fibers 1871. The balloon 1836 will then be injected with resin 1870 (not shown in FIG. 46) to form a composite structure of resin 1870, fibers 1871 and the balloon 1836 in the IM canal. The balloon 1836 (or bag or sleeve) is preferably fabricated from resorbable material. As noted above, a braid 1805 can be used that is pre-charged with chopped fibers 1871 prior to injection with resin 1870. Upon injection with resin 1870, the balloon 1836 will engage the endosteal wall of the IM canal.

Turning to FIG. 47, the assembly 1835c includes an insertion tube 1850, a balloon 1836 and braid 1805 and a structural stiffening member 1875. While only a single stiffening member 1875 is shown, a plurality of stiffening members 1875 may be utilized. Further, while a tubular stiffening member 1875 is illustrated, the stiffening member may be a pin or rod as well. Other shapes for stiffening members 1875 will be apparent to those skilled in the art. Resin may be injected through the axial opening 1876 in the stiffening member 1875 or through the annular area 1877 between the elongated braided structure 1805 and stiffening member 1875 using an injection tube 1837 (not shown in FIG. 47). Again, the balloon 1836 (or bag or sleeve) may not be necessary, depending upon the structure of the elongated braided structure 1805 and its ability to retain and prevent migration of resin. Alternatively, the elongated braided structure 1805 (or spacer fabric structure 1810) may be eliminated in favor of the balloon 1836, bag or sleeve. Again, the elongated braid 1805 or spacer fabric structure 1810 and balloon 1836, if utilized, are sized so as to expand engage the endosteal wall of the IM canal.

Turning to FIG. 48, the assembly 1835*d* includes an insertion tube 1850 and a braid 1805 that has been pre-wetted with uncured resin 1870*a*. A light pipe or light emitting device 1880 is shown passing through the axial center of the pre-wetted braid 1805. The elongated braided structure 1805 may be wetted with resin 1870*a* outside of the tube 1850 and the resin 1870*a* may be a light-curable resin. In this embodiment, an outer balloon 1836 or retention means may not be required. Once the insertion tube 1850 is removed, the elongated braided structure 1805 is allowed to expand and engage the endosteal wall of the IM canal before the resin is cured with the light-emitting device 1880.

Figure 49:
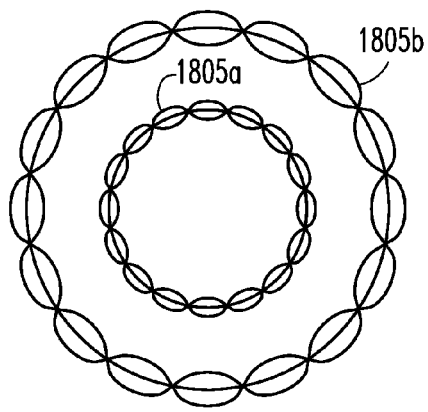
FIG. 49 is an end view of a dual braid system with a smaller elongated braid disposed axially within a larger elongated braid.
Figure 50:
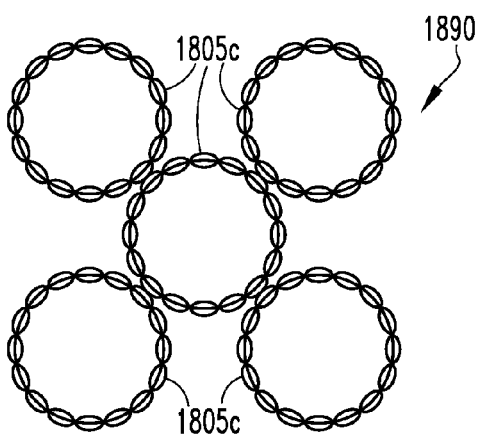
FIG. 50 is an end view illustrating the use of a bundle of elongated braids, in this example, five braids.
Figure 51:
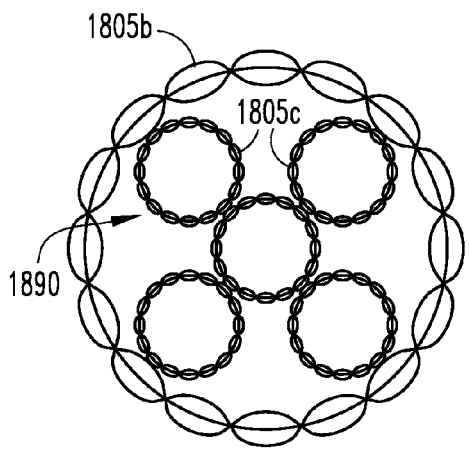
FIG. 51 is an end view illustrating the use of a bundle of elongated braids disposed axially within a larger elongated braid.

In addition to a single elongated braid 1805, for added structural strength, a plurality of braids or braids with multiple cavities that extend along the length of the braid and may be employed as illustrated in FIGS. 49-54. FIG. 49 illustrates the use of a smaller elongated braid 1805*a* disposed axially within a larger braid 1805*b*. FIG. 50 illustrates a plurality of smaller braids 1805*c* used as a bundle 1890. FIG. 51 illustrates the use of a bundle 1890 as shown in FIG. 50 disposed within a larger outer braid 1805*b*. The multiple braid systems of FIGS. 49-50 provide additional braided surface areas that become embedded or filled with resin 1870. When the resin is cured, the structures shown in FIGS. 49-51 will typically be stronger than single braid systems.

Figure 52:
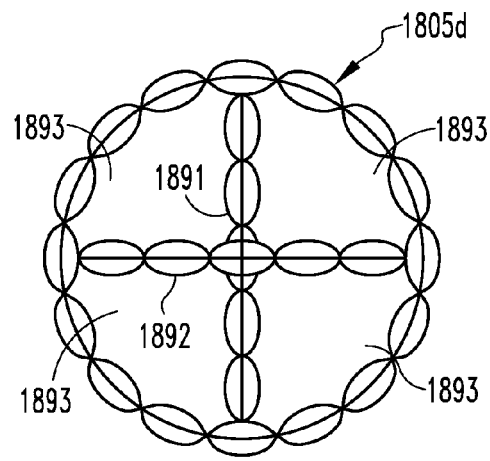
FIG. 52 is an end view of a braid with four separate cavities that extend axially along the braid.
Figure 53:
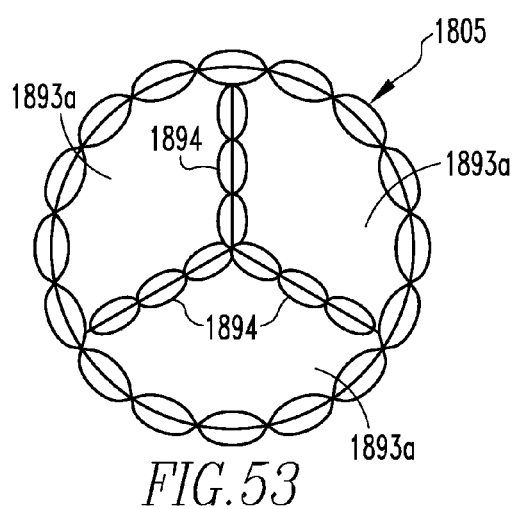
FIG. 53 illustrates the braid with three cavities that extend axially along the braid.
Figure 54:
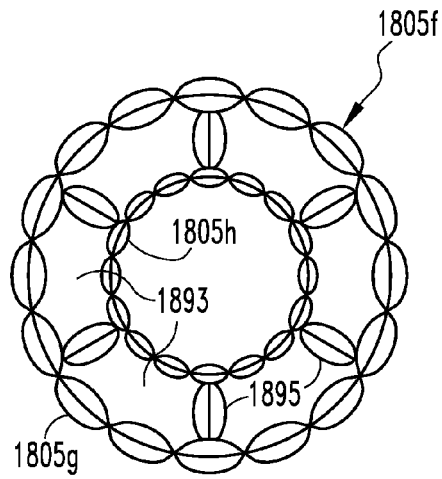
FIG. 54 illustrates a braid with six peripheral cavities and a central axial cavity that extend along the braid.

In contrast, the elongated braided structures may include multiple cavities as illustrated in FIGS. 52-54. In FIG. 52, the elongated braided structure 1805*d* includes a pair of perpendicular wall structures 1891, 1892 to create for cavities 1893 that extend along the length of the elongated braided structure 1805*d*. In FIG. 53, the elongated braided structure 1805*e* includes three walls 1894 to create three cavities 1893. In FIG. 54, the braid structure 1805*f* includes an outer elongated braid 1805*g*, an inner elongated braid 1805*h*, and a plurality of radial wall structures 1895 that define a plurality of peripheral cavities 1893*b* that extend along the length of the braid structure 1805*f*. The wall structures 1891-1895 become filled or embedded with resin 1870 to add strength to the overall braid structures 1805*d*-1805*f*.

In summary, a vast number of possibilities for the insertion assembly 1835, 1835*a*-1835*d* is possible. Elongated braided structures 1805 or triaxial braided elongated structures 1815 may be used alone with resin 1870 or in combination with a retention means such as a balloon 1836, bag or sleeve. Spacer fabric structures 1810 may be used alone with resin or in combination with a retention means such as a balloon 1836, bag or sleeve. Chopped fibers 1871 may be added to the resin in any of the above embodiments or added to the elongated braided structure 1805 or spacer fabric structure 1810 prior to insertion and prior to injection with resin 1870. A balloon 1836, bag or sleeve may be charged with chopped fibers and used with or without an elongated braid 1805, triaxial braid 1815, or spacer fabric structure 1810, 1810*a*. Resorbable reinforcing elements such as pins or tubes 1875 may be combined with any of the above embodiments. Elongated braid structures 1805, elongated triaxial braided structures 1815 and spacer fabric structures 1810 may also be pre-wetted with resin prior to insertion and then cured in situ after radial expansion to the endosteal wall. The reinforcing element may be used to insert the pre-wetted braid 1805, 1815 or the spacer fabric structure 1810. In addition to single braid systems illustrated in FIGS. 36-48, multiple braid systems or braids with multiple cavities may be utilized as illustrated in FIGS. 49-54 to provide additional braided surface areas that can be embedded with cured resin for added strength. Any of the braided structures illustrated in FIGS. 49-54 may be triaxial, or braided structures with longitudinal fibers or longitudinal fiber bundles disposed therein.

An elongated braid 1805, 1815 or spacer fabric structure 1810 is manufactured as described above. The distal end 1830 of the elongated braided structure 1805 may be tapered or shaped as described above. In any event, the ends of the elongated braided structure 1805, 1815 or the spacer fabric structure 1810 should be melted to eliminate fraying. In one example, the flexible insertion tube 1850 has an OD of about 4.2 mm and the elongated braid 1805 has a relaxed OD of about 8 mm. The elongated braided structure 1805 is placed over the flexible injection tube 1837 which, at its distal end, has an OD of about 2 mm. The injection tube 1837 is used to push the elongated braided structure 1805 into the insertion tube 1850 or, if a balloon 1836, bag or sleeve is employed, the injection tube 1837 is used to push the elongated braided structure 1805 into the balloon 1836 and then the injection tube 1837, braid 1805, and balloon 1836 are then inserted into the flexible insertion tube 1850. The distal end of the balloon 1836 is closed and the proximal end of the balloon 1836 may include a valve such as a hemostatic valve to provide a seal around the injection tube 1837.

Surgical kits of various forms may also be provided for use by physicians. For example, a surgical kit may include a woven elongated structure 1805, which accommodates a distal end of an injection tube 1837, and which is disposed within a balloon 1836. The balloon 1836, elongated woven structure 1805 and injection tube 1837 may be disposed within an insertion tube or catheter 1850. A valve 1841 may are may not be connected to the balloon 1836 and injection tube 1837. A syringe or other resin 1870 delivery device may also be included for delivering resin 1870 to the woven elongated structure 1805 and to the interior of the balloon 1836. The resin 1870 may also be provided in a kit form which includes an appropriate catalyst and filler, if necessary. Reinforcing elements 1875 or fibers 1871 may also be included and may be positioned inside the woven elongated structure 1805.

Surgical Procedures

Various surgical procedures may be employed to utilize the assemblies 1835-1835*d*. First, an incision is made in an entry portal 1831 is drilled into the fractured bone at an appropriate spacing from the fracture 102. The two-part polyurethane resin is mixed. The selected assembly 1835-1835*d* is then inserted into the IM canal. The insertion tube 1850 is withdrawn. The resin is injected through the injection tube 1837 thereby filling the elongated braided structure 1805 (or braid 1815 or spacer fabric structure 1810) and balloon 1836 (or bag or sleeve) with resin 1870. The injection tube 1837 is withdrawn and the proximal end of the balloon 1836 is trimmed at the portal site 1831. The incision is then closed. The elongated braided structure 1805 and/or balloon 1836 may be pre-charged with chopped fibers 1871 as described above. A balloon 1836 (or bag or sleeve) may be utilized without a braid 1805 and vice versa as discussed above.

If a pre-wetted braid 1805 is utilized, an incision and entry portal 1831 is made. The resin 1870 is mixed and injected into a container. The elongated braid 1805, triaxial elongated braid 1815 or spacer fabric structure 1810 is soaked in the resin and then inserted into the IM canal using an insertion tube 1850 and injection tube 1837 as a pusher. The insertion tube 1850 is withdrawn. If the resin is to be cured by body temperature, the injection tube 1837 can be withdrawn. If light is needed to cure the resin 1870, a light pipe or other light emitting device is inserted down through the wetted braid 1805, 1815 or spacer fabric structure 1810. The light is passed through the wetted fabric and then withdrawn. The wound is then closed. A pre-wetted braid 1805, 1815 or spacer fabric structure 1810 can also be practiced with a balloon 1836, bag or sleeve, with or without light-curable resin.

The structures and methods disclosed herein may be used independently for bone treatment or fracture repair. Alternatively, the structures and methods disclosed herein may be used in conjunction with external or internal devices. The structures and methods disclosed herein also may be used in an osteotomy.

While only certain embodiments have been set forth, alternatives and modifications will be apparent from the above description to those skilled in the art. These and other alternatives are considered equivalents and within the spirit and scope of this disclosure and the appended claims.

The invention claimed is:

1. A hardenable and moldable material for orthopedic implantation and reconstruction, the material comprising:
    a resorbable polymer resin;
    a first filler having a first mean particle diameter ranging from about 5 to about 15 µm; and
    at least one additional filler selected from the group consisting of a second filler having a mean particle diameter ranging from about 400 to about 1800 µm and a third filler having a mean particle size ranging from about 1800 to about 4000 µm, wherein the at least one additional filler provides porosity within the material after hardening and is present in an amount greater than the first filler.

2. The material of claim 1 wherein:
    the resin is present in an amount ranging from about 15 to about 40 wt %;
    the first filler is present in an amount ranging from about 10 to about 25 wt %;
    the additional filler is present in an amount greater than the first filler and ranging from about 20 to about 75 wt %.

3. The material of claim 2 wherein the additional filler comprises both second and third fillers.

4. The material of claim 3 wherein the first filler has a mean particle diameter ranging from about 8 to about 12 µm, the second filler has a mean particle diameter ranging from about 800 to about 1800 µm and the third filler has a mean particle diameter ranging from greater than 1800 to about 2800 µm.

5. The material of claim 4 wherein:
    the resin is present in an amount ranging from about 20 to about 30 wt %;
    the first filler is present in an amount ranging from about 10 to about 20 wt %;
    the second filler is present in an amount ranging from about 25 to about 35 wt %;
    the third filler is present in an amount ranging from about 20 to about 30 wt %.

6. The material of claim 4 wherein
    the resin is present in an amount ranging from about 15 to about 40 wt %;
    the first filler is present in an amount ranging from about 10 to about 25 wt %;
    the second filler is present in an amount ranging from about 20 to about 40 wt %;
    the third filler is present in an amount ranging from about 15 to about 35 wt %.

7. The material of claim 6 wherein the first filler is present in a first amount, the second filler is present and a second amount and the third filler is present in a third amount, and a ratio of the second to third amounts ranges from about 1:1 to about 1.5:1.

8. The material of claim 7 wherein a ratio of the second and third amounts combined to the first amount ranges from about 3.5:1 to about 4.5:1.

9. The material of claim 1 further comprising a porogen comprising water soluble crystals.

10. The material of claim 9 wherein the porogen comprises mannitol.

11. The material of claim 1 further comprising water as a blowing agent.

12. The material of claim 1 wherein the first, and additional fillers are selected from the group consisting of degradable polymer PU, PLA, PGA, PCL, or co-polymers thereof, hydroxyapatite (HA), calcium phosphates, orthophosphates, monocalcium phosphates, dicalcium phosphates, tricalcium phsosphates, whitlockite, tetracalcium phosphates, amorphous calcium phosphates, magnesium and magnesium alloys.

13. The material of claim 12 comprising at least two different fillers from the group.

14. The material of claim 12 wherein the first filler is hydroxyapatite (HA) having a mean particle diameter of 10 µm.

15. The material of claim 1 comprising at least two different materials selected from the group consisting of degradable polymers PU, PLA, PGA, PCL, or co-polymers thereof, hydroxyapatite (HA), calcium phosphates, orthophosphates, monocalcium phosphates, dicalcium phosphates, tricalcium phosphates, whitlockite, tetracalcium phosphates and amorphous calcium phosphates, magnesium, magnesium alloys and calcium sulfate.

16. The material of claim 1, wherein upon combination with the resorbable polymer resin, the at least one additional filler creates voids that increase the porosity of the material.

17. A kit for an orthopedic implant comprising:
    a resorbable polymer resin;
    a first filler having a mean particle diameter ranging from about 5 to about 15 µm; and
    at least one additional filler selected from a second filler having a mean particle diameter ranging from about 400 to about 1800 µm and a third filler having a mean particle size ranging from about 1800 to about 4000 µm;
    wherein mixing the fillers with the resorbable polymer resin forms a hardenable and moldable putty.

18. The kit of claim 17 wherein:
    the resin is present in an amount ranging from about 15 to about 40 wt %;
    the first filler is present in an amount ranging from about 10 to about 25 wt %;
    the additional filler is present in an amount greater than the first filler and ranging from about 20 to about 75 wt %.

19. The kit of claim 17 wherein the additional filler comprises both second and third fillers.

20. The kit of claim 17 wherein the first filler is present in a first amount, the second filler is present and a second amount and the third filler is present in a third amount, and a ratio of the second to third amounts ranges from about 1:1 to about 1.5:1.

21. A hardenable and moldable material for orthopedic implantation and reconstruction, the material comprising:
   a resorbable polymer resin;
   at least one filler selected from the group consisting of first filler particles having a mean particle diameter ranging from about 400 to about 1800 μm and second filler particles having a mean particle size ranging from about 1800 to about 4000 μm, wherein the filler provides porosity within the material after hardening; and
   an additional filler comprising particles having a mean particle diameter of about 5 μm to about 15 μm.

22. The material of claim 21 wherein the first filler particles are present in a first amount and the second filler particles are present in a second amount, and a ratio of the first to second amounts ranges from about 1:1 to about 1.5:1.

23. The material of claim 21 wherein the at least one filler comprises the second filler particles having a mean particle diameter of about 1800 μm to about 4000 μm.

\* \* \* \* \*